(12) United States Patent
Ho et al.

(10) Patent No.: US 11,180,570 B2
(45) Date of Patent: Nov. 23, 2021

(54) J591 MINIBODIES AND CYS-DIABODIES FOR TARGETING HUMAN PROSTATE SPECIFIC MEMBRANE ANTIGEN (PSMA) AND METHODS FOR THEIR USE

(71) Applicant: ImaginAb, Inc., Inglewood, CA (US)

(72) Inventors: David T. Ho, Long Beach, CA (US); Tove Olafsen, Reseda, CA (US); Arye Lipman, El Segundo, CA (US)

(73) Assignee: ImaginAb, Inc., Inglewood, CA (US)

( * ) Notice: Subject to any disclaimer, the term of this patent is extended or adjusted under 35 U.S.C. 154(b) by 238 days.

(21) Appl. No.: 16/273,948

(22) Filed: Feb. 12, 2019

(65) Prior Publication Data
US 2019/0300622 A1    Oct. 3, 2019

Related U.S. Application Data

(62) Division of application No. 14/266,391, filed on Apr. 30, 2014, now abandoned, which is a division of application No. 12/959,340, filed on Dec. 2, 2010, now Pat. No. 8,772,459.

(60) Provisional application No. 61/266,134, filed on Dec. 2, 2009.

(51) Int. Cl.
| *A61K 39/00* | (2006.01) |
| *C07K 16/30* | (2006.01) |
| *A61P 35/00* | (2006.01) |
| *A61K 51/10* | (2006.01) |

(52) U.S. Cl.
CPC ...... *C07K 16/3069* (2013.01); *A61K 51/1072* (2013.01); *A61P 35/00* (2018.01); *A61K 2039/505* (2013.01); *C07K 2317/24* (2013.01); *C07K 2317/526* (2013.01); *C07K 2317/56* (2013.01); *C07K 2317/622* (2013.01); *C07K 2317/64* (2013.01); *C07K 2317/77* (2013.01); *C07K 2317/90* (2013.01)

(58) Field of Classification Search
CPC .............................................. A61K 2039/505
See application file for complete search history.

(56) References Cited

U.S. PATENT DOCUMENTS

| 4,892,824 A | 1/1990 | Skaletsky |
| 4,943,525 A | 7/1990 | Dawson |
| 5,256,395 A | 10/1993 | Barbet et al. |
| 5,332,567 A | 7/1994 | Goldenberg |
| 5,376,249 A | 12/1994 | Afeyan et al. |
| 5,518,889 A | 5/1996 | Lander et al. |
| 5,523,210 A | 6/1996 | Paulus |
| 5,534,254 A | 7/1996 | Huston et al. |
| 5,538,866 A | 7/1996 | Israeli et al. |
| 5,582,996 A | 12/1996 | Curtis |
| 5,591,828 A | 1/1997 | Bosslet et al. |
| 5,627,078 A | 5/1997 | Karl et al. |
| 5,637,481 A | 6/1997 | Ledbetter et al. |
| 5,688,690 A | 11/1997 | Valiante et al. |
| 5,693,477 A | 12/1997 | Cornell et al. |
| 5,705,614 A | 1/1998 | Ring |
| 5,712,136 A | 1/1998 | Wickham et al. |
| 5,747,035 A | 5/1998 | Presta et al. |
| 5,762,930 A | 6/1998 | Fanger et al. |
| 5,821,333 A | 10/1998 | Carter et al. |
| 5,830,473 A | 11/1998 | Thierfelder |
| 5,830,478 A | 11/1998 | Raso et al. |
| 5,837,242 A | 11/1998 | Holliger et al. |
| 5,837,821 A | 11/1998 | Wu |
| 5,840,854 A | 11/1998 | Hellstrom et al. |
| 5,844,094 A | 12/1998 | Hudson et al. |
| 5,851,527 A | 12/1998 | Hudson et al. |
| 5,852,186 A | 12/1998 | Sodroski et al. |
| 5,861,156 A | 1/1999 | George et al. |
| 5,863,765 A | 1/1999 | Berry et al. |
| 5,869,049 A | 2/1999 | Noelle et al. |
| 5,869,053 A | 2/1999 | Stern et al. |
| 5,869,620 A | 2/1999 | Whitlow et al. |
| 5,876,691 A | 3/1999 | Chester et al. |
| 5,877,291 A | 3/1999 | Mezes et al. |
| 5,932,448 A | 8/1999 | Tso et al. |
| 5,935,818 A | 8/1999 | Israeli et al. |
| 5,942,229 A | 8/1999 | Noelle et al. |
| 5,951,982 A | 9/1999 | Zöller et al. |
| 5,959,083 A | 9/1999 | Bosslet et al. |

(Continued)

FOREIGN PATENT DOCUMENTS

| CN | 1356341 | 7/2002 |
| CN | 1854295 | 11/2006 |

(Continued)

OTHER PUBLICATIONS

US 8,748,586 B2, 06/2014, Ho et al. (withdrawn)

(Continued)

*Primary Examiner* — Stephen L Rawlings
(74) *Attorney, Agent, or Firm* — Knobbe. Martens. Olson & Bear, LLP

(57) ABSTRACT

In one embodiment, a minibody monomer that binds PSMA is provided. The minibody monomer is encoded by a nucleotide sequence comprising, from N-terminus to C-terminus, an scFv sequence that can bind PSMA, an artificial hinge sequence, and a human IgG CH3 sequence. In another embodiment, a CysDB monomer that binds PSMA is provided. The CysDB monomer may be encoded by a nucleotide sequence comprising, from N-terminus to C-terminus, an scFv sequence that can bind PSMA and a cysteine tail. In other embodiments, methods for diagnosing or treating a cancer associated with PSMA expression in a subject are provided.

18 Claims, 29 Drawing Sheets

Specification includes a Sequence Listing.

(56) References Cited

U.S. PATENT DOCUMENTS

| | | |
|---|---|---|
| 5,980,896 A | 11/1999 | Hellstrom et al. |
| 5,989,830 A | 11/1999 | Davis et al. |
| 5,990,275 A | 11/1999 | Whitlow et al. |
| 6,010,902 A | 1/2000 | Ledbetter et al. |
| 6,030,792 A | 2/2000 | Otterness et al. |
| 6,071,490 A | 6/2000 | Griffiths et al. |
| 6,083,763 A | 7/2000 | Balch |
| 6,096,871 A | 8/2000 | Presta et al. |
| 6,099,841 A | 8/2000 | Hillan et al. |
| 6,107,090 A | 8/2000 | Bander |
| 6,121,022 A | 9/2000 | Presta et al. |
| 6,136,311 A | 10/2000 | Bander |
| 6,150,508 A | 11/2000 | Murphy et al. |
| 6,193,966 B1 | 2/2001 | Deo et al. |
| 6,197,298 B1 | 3/2001 | Chang |
| 6,200,765 B1 | 3/2001 | Murphy et al. |
| 6,201,167 B1 | 3/2001 | Pothier |
| 6,241,961 B1 | 6/2001 | Benes et al. |
| 6,248,516 B1 | 6/2001 | Winter et al. |
| 6,284,742 B1 | 9/2001 | Curiel et al. |
| 6,294,391 B1 | 9/2001 | Badley et al. |
| 6,312,694 B1 | 11/2001 | Thorpe et al. |
| 6,329,503 B1 | 12/2001 | Afar et al. |
| 6,342,587 B1 | 1/2002 | Barbas, III et al. |
| 6,361,774 B1 | 3/2002 | Griffiths et al. |
| 6,368,596 B1 | 4/2002 | Ghetie et al. |
| 6,383,759 B1 | 5/2002 | Murphy et al. |
| 6,387,350 B2 | 5/2002 | Goldenberg |
| 6,399,068 B1 | 6/2002 | Goldenberg |
| 6,458,933 B1 | 10/2002 | Hansen |
| 6,491,916 B1 | 12/2002 | Bluestone et al. |
| 6,492,123 B1 | 12/2002 | Hollinger et al. |
| 6,569,432 B1 | 5/2003 | Israeli et al. |
| 6,602,684 B1 | 8/2003 | Umana et al. |
| 6,649,163 B1 | 11/2003 | Bander |
| 6,709,844 B1 | 3/2004 | Levy |
| 6,767,711 B2 | 7/2004 | Bander |
| 6,770,450 B1 | 8/2004 | Bander |
| 6,824,780 B1 | 11/2004 | Devaux et al. |
| 6,833,438 B1 | 12/2004 | Afar et al. |
| 6,835,866 B1 | 12/2004 | Mangelsdorf et al. |
| 6,861,234 B1 | 3/2005 | Simard et al. |
| 6,869,620 B2 | 3/2005 | Moore |
| 6,870,034 B2 | 3/2005 | Breece et al. |
| 6,887,975 B2 | 5/2005 | Afar et al. |
| 6,953,668 B1 | 10/2005 | Israeli et al. |
| 6,977,074 B2 | 12/2005 | Kundig et al. |
| 6,994,851 B1 | 2/2006 | Kundig et al. |
| 7,037,647 B1 | 5/2006 | Israeli et al. |
| 7,045,605 B2 | 5/2006 | Bander et al. |
| 7,053,186 B2 | 5/2006 | Afar et al. |
| 7,070,782 B1 | 7/2006 | Israeli et al. |
| 7,105,159 B1 | 9/2006 | Israeli et al. |
| 7,112,412 B1 | 9/2006 | Bander |
| 7,163,680 B2 | 1/2007 | Bander |
| 7,166,714 B2 | 1/2007 | Afar et al. |
| 7,192,586 B2 | 3/2007 | Bander |
| 7,232,682 B2 | 6/2007 | Simard et al. |
| 7,235,641 B2 | 6/2007 | Kufer et al. |
| 7,319,006 B2 | 1/2008 | Afar et al. |
| 7,323,553 B2 | 1/2008 | Fahrner et al. |
| 7,364,729 B2 | 4/2008 | Kundig et al. |
| 7,375,078 B2 | 5/2008 | Feng |
| 7,390,654 B2 | 6/2008 | Levy |
| 7,399,461 B2 | 7/2008 | Heston et al. |
| 7,435,416 B2 | 10/2008 | Devaux et al. |
| 7,452,539 B2 | 11/2008 | Emery et al. |
| 7,455,991 B2 | 11/2008 | Afar et al. |
| 7,485,299 B2 | 2/2009 | Afar et al. |
| 7,485,704 B2 | 2/2009 | Fahrner et al. |
| 7,494,646 B2 | 2/2009 | Jakobovits et al. |
| 7,498,298 B2 | 3/2009 | Doronina et al. |
| 7,514,078 B2 | 4/2009 | Bander et al. |
| 7,517,670 B2 | 4/2009 | Umana et al. |
| 7,521,541 B2 | 4/2009 | Eigenbrot et al. |
| 7,524,813 B2 | 4/2009 | Zundel et al. |
| 7,541,441 B2 | 6/2009 | Rosen et al. |
| 7,575,749 B2 | 8/2009 | Afar et al. |
| 7,595,379 B2 | 9/2009 | Gudas et al. |
| 7,611,904 B2 | 11/2009 | Afar et al. |
| 7,612,181 B2 | 11/2009 | Wu et al. |
| 7,622,569 B2 | 11/2009 | Raitano et al. |
| 7,642,054 B2 | 1/2010 | Afar et al. |
| 7,662,936 B2 | 2/2010 | Kadkhodayan et al. |
| 7,666,414 B2 | 2/2010 | Bander |
| 7,666,425 B1 | 2/2010 | Bander |
| 7,678,371 B2 | 3/2010 | Lugovskoy et al. |
| 7,727,533 B2 | 6/2010 | Afar et al. |
| 7,745,394 B2 | 6/2010 | Doronina et al. |
| 7,754,681 B2 | 7/2010 | Feng |
| 7,807,799 B2 | 10/2010 | Fahrner et al. |
| 7,820,166 B2 | 10/2010 | Lanzavecchia |
| 7,838,637 B2 | 11/2010 | Kontermann et al. |
| 7,855,275 B2 | 12/2010 | Eigenbrot et al. |
| 7,867,483 B2 | 1/2011 | Delcayre et al. |
| 7,884,179 B2 | 2/2011 | Faris et al. |
| 7,888,035 B2 | 2/2011 | Klass et al. |
| 7,897,356 B2 | 3/2011 | Klass et al. |
| 7,906,329 B2 | 3/2011 | Umana et al. |
| 7,928,201 B2 | 4/2011 | Afar et al. |
| 7,939,503 B2 | 5/2011 | Jakobovits et al. |
| 7,947,276 B2 | 5/2011 | Jakobovits et al. |
| 7,947,459 B2 | 5/2011 | Hubert et al. |
| 7,947,839 B2 | 5/2011 | Gazzard et al. |
| 7,960,109 B2 | 6/2011 | Hessels et al. |
| 7,964,566 B2 | 6/2011 | Doronina et al. |
| 7,964,567 B2 | 6/2011 | Doronina et al. |
| 7,968,307 B2 | 6/2011 | Afar et al. |
| 7,989,434 B2 | 8/2011 | Feng |
| 7,994,135 B2 | 8/2011 | Doronina et al. |
| 7,998,701 B2 | 8/2011 | Chua et al. |
| 8,007,994 B2 | 8/2011 | Mangelsdorf et al. |
| 8,008,442 B2 | 8/2011 | Jakobovits et al. |
| 8,012,937 B2 | 9/2011 | Raitano et al. |
| 8,013,128 B2 | 9/2011 | Gudas et al. |
| 8,013,135 B2 | 9/2011 | Jakobovits et al. |
| 8,043,830 B2 | 10/2011 | Barat et al. |
| 8,206,932 B2 | 6/2012 | Gudas et al. |
| 8,278,424 B2 | 10/2012 | Gudas et al. |
| 8,772,459 B2 | 7/2014 | Ho et al. |
| 2002/0004215 A1 | 1/2002 | Osbourn et al. |
| 2002/0018749 A1 | 2/2002 | Hudson et al. |
| 2002/0037289 A1 | 3/2002 | Thorpe et al. |
| 2002/0119096 A1 | 8/2002 | Griffiths |
| 2002/0119153 A1 | 8/2002 | Thorpe et al. |
| 2002/0132979 A1 | 9/2002 | Chen |
| 2002/0136689 A1 | 9/2002 | Reiter et al. |
| 2003/0118583 A1 | 6/2003 | Emery et al. |
| 2003/0170228 A1 | 9/2003 | Ashkenazi et al. |
| 2003/0175900 A1 | 9/2003 | Ashkenazi et al. |
| 2003/0211096 A1 | 11/2003 | Ashkenazi et al. |
| 2004/0018519 A1 | 1/2004 | Wright |
| 2004/0033511 A1 | 2/2004 | Pfizenmaier et al. |
| 2004/0038339 A1 | 2/2004 | Kufer et al. |
| 2004/0071690 A1 | 4/2004 | Hudson et al. |
| 2004/0162411 A1 | 8/2004 | Lanzavecchia |
| 2004/0241817 A1 | 12/2004 | Umana et al. |
| 2005/0026178 A1 | 2/2005 | Nilsen-Hamilton |
| 2005/0136050 A1 | 6/2005 | Kufer et al. |
| 2005/0175618 A1 | 8/2005 | Carroll et al. |
| 2005/0215769 A1 | 9/2005 | Breece et al. |
| 2005/0232929 A1 | 10/2005 | Kadkhodayan et al. |
| 2005/0272128 A1 | 12/2005 | Umana et al. |
| 2006/0062793 A1 | 3/2006 | Webb et al. |
| 2006/0159689 A1 | 7/2006 | Chiang et al. |
| 2006/0234226 A1 | 10/2006 | Fahrner et al. |
| 2006/0234271 A1 | 10/2006 | Su |
| 2006/0269540 A1 | 11/2006 | Robert et al. |
| 2006/0275312 A1 | 12/2006 | Chua et al. |
| 2007/0059306 A1 | 3/2007 | Grosmaire |
| 2007/0134243 A1 | 6/2007 | Gazzard et al. |
| 2007/0212331 A1 | 9/2007 | Baldassare et al. |
| 2007/0243950 A1 | 10/2007 | Billings |
| 2007/0253950 A1 | 11/2007 | Jacobsen |

(56) References Cited

U.S. PATENT DOCUMENTS

| | | |
|---|---|---|
| 2007/0286858 A1 | 12/2007 | Clancy |
| 2008/0152586 A1 | 6/2008 | Hudson et al. |
| 2008/0171040 A1 | 7/2008 | Ebens et al. |
| 2008/0206192 A1 | 8/2008 | Moller et al. |
| 2008/0213256 A1 | 9/2008 | Kufer et al. |
| 2008/0213921 A1 | 9/2008 | Robertson et al. |
| 2008/0227736 A1 | 9/2008 | Chen et al. |
| 2008/0267872 A1 | 10/2008 | Raitano et al. |
| 2008/0279850 A1 | 11/2008 | Brady et al. |
| 2008/0305105 A1 | 12/2008 | Kufer et al. |
| 2008/0305476 A1 | 12/2008 | Robertson et al. |
| 2009/0004109 A1 | 1/2009 | Jacobovits et al. |
| 2009/0022738 A1 | 1/2009 | Hofmeister et al. |
| 2009/0041758 A1 | 2/2009 | Glaser |
| 2009/0041791 A1 | 2/2009 | Feng |
| 2009/0053223 A1 | 2/2009 | Hoffmann et al. |
| 2009/0099344 A1 | 4/2009 | Fahrner et al. |
| 2009/0136475 A1 | 5/2009 | Barth |
| 2009/0155290 A1 | 6/2009 | Carroll et al. |
| 2009/0202548 A1 | 8/2009 | Gudas et al. |
| 2009/0214539 A1 | 8/2009 | Grosmaire |
| 2009/0226465 A1 | 9/2009 | Jackson |
| 2009/0238755 A1 | 9/2009 | Bander |
| 2009/0252729 A1 | 10/2009 | Farrington et al. |
| 2009/0272169 A1 | 11/2009 | Pan |
| 2009/0275081 A1 | 11/2009 | Barat et al. |
| 2009/0280120 A1 | 11/2009 | Bander et al. |
| 2009/0286258 A1 | 11/2009 | Kaur et al. |
| 2009/0311181 A1 | 12/2009 | Wu et al. |
| 2010/0003766 A1 | 1/2010 | Eigenbrot et al. |
| 2010/0034837 A1 | 2/2010 | Beria et al. |
| 2010/0047239 A1 | 2/2010 | Wu et al. |
| 2010/0058803 A1 | 3/2010 | Ransbarger |
| 2010/0069616 A1 | 3/2010 | Wu et al. |
| 2010/0111856 A1 | 5/2010 | Gill et al. |
| 2010/0135900 A1 | 6/2010 | Cerveny |
| 2010/0184046 A1 | 7/2010 | Klass et al. |
| 2010/0189651 A1 | 7/2010 | Stagliano |
| 2010/0209343 A1 | 8/2010 | Bander et al. |
| 2010/0215581 A1 | 8/2010 | Hoffmann |
| 2010/0255479 A1 | 10/2010 | Mikolajczyk et al. |
| 2010/0266491 A1 | 10/2010 | Farokhzad et al. |
| 2010/0267933 A1 | 10/2010 | Wilson |
| 2010/0278919 A1 | 11/2010 | Denes et al. |
| 2010/0297004 A1 | 11/2010 | Wu et al. |
| 2010/0303715 A1 | 12/2010 | Israeli |
| 2010/0303814 A1 | 12/2010 | Cizeau et al. |
| 2010/0303821 A1 | 12/2010 | Ashman |
| 2010/0310452 A1 | 12/2010 | Israeli |
| 2010/0310584 A1 | 12/2010 | Carroll et al. |
| 2011/0006466 A1 | 1/2011 | Ichikawa |
| 2011/0009001 A1 | 1/2011 | Chen |
| 2011/0020327 A1 | 1/2011 | Moya et al. |
| 2011/0069019 A1 | 3/2011 | Carpendale et al. |
| 2011/0076287 A1 | 3/2011 | Cohen et al. |
| 2011/0081345 A1 | 4/2011 | Moore |
| 2011/0086050 A1 | 4/2011 | Presta |
| 2011/0104059 A1 | 5/2011 | St. Croix et al. |
| 2011/0110852 A1 | 5/2011 | Miller et al. |
| 2011/0117023 A1 | 5/2011 | Yamauchi |
| 2011/0123532 A1 | 5/2011 | Gurney et al. |
| 2011/0137017 A1 | 6/2011 | Eigenbrot et al. |
| 2011/0207155 A1 | 8/2011 | Pengo et al. |
| 2011/0227023 A1 | 9/2011 | Bethune et al. |
| 2011/0262968 A1 | 10/2011 | Gudas et al. |
| 2011/0268656 A1 | 11/2011 | Ho et al. |
| 2012/0076728 A1 | 3/2012 | Wu et al. |
| 2012/0144110 A1 | 6/2012 | Smith |
| 2012/0283418 A1 | 11/2012 | Wu et al. |

FOREIGN PATENT DOCUMENTS

| | | |
|---|---|---|
| EP | 0 668 777 | 8/1995 |
| EP | 0 956 506 | 7/1996 |
| EP | 1 005 494 | 3/1997 |
| EP | 1 550 729 | 7/2005 |
| EP | 1 629 011 | 3/2006 |
| EP | 1 997 514 | 12/2008 |
| EP | 2 226 394 | 9/2010 |
| EP | 2 260 858 | 12/2010 |
| JP | H06-506362 | 7/1994 |
| JP | 2003-504414 | 2/2003 |
| JP | 2003-530092 | 10/2003 |
| JP | 2007-14267 | 1/2007 |
| JP | 2008-528668 | 7/2008 |
| WO | WO 93/11794 | 6/1993 |
| WO | WO 1993/015199 | 8/1993 |
| WO | WO 1994/009820 | 5/1994 |
| WO | WO 96/008570 | 3/1996 |
| WO | WO 1996/008570 | 3/1996 |
| WO | WO 1996/026272 | 8/1996 |
| WO | WO 1997/035616 | 10/1997 |
| WO | WO 1999/056779 | 11/1999 |
| WO | WO 2000/014234 | 3/2000 |
| WO | WO 2001/005427 | 1/2001 |
| WO | WO 01/009303 | 2/2001 |
| WO | WO 2001/009303 | 2/2001 |
| WO | WO 01/68708 | 9/2001 |
| WO | WO 2001/082963 | 11/2001 |
| WO | WO 2002/022680 | 3/2002 |
| WO | WO 2003/038098 | 5/2003 |
| WO | WO 2005/026334 | 3/2005 |
| WO | WO 2005/043165 | 5/2005 |
| WO | WO 2005/061547 | 7/2005 |
| WO | WO 2005/068616 | 7/2005 |
| WO | WO 2005/094882 | 10/2005 |
| WO | WO 2007/064345 | 6/2007 |
| WO | WO 2007/109321 | 9/2007 |
| WO | WO 2007/137117 | 11/2007 |
| WO | WO 2009/017823 | 2/2009 |
| WO | WO 2009/032949 | 3/2009 |
| WO | WO 2009/076099 | 6/2009 |
| WO | WO 2009/082443 | 7/2009 |
| WO | WO 2009/097128 | 8/2009 |
| WO | WO 2009/130575 | 10/2009 |
| WO | WO 2010/037397 | 4/2010 |
| WO | WO 2010/042904 | 4/2010 |
| WO | WO 2010/102195 | 9/2010 |
| WO | WO 2011/000054 | 1/2011 |
| WO | WO 2011/056983 | 5/2011 |
| WO | WO 2011/069019 | 6/2011 |
| WO | WO 2011/075786 | 6/2011 |
| WO | WO 2011/090762 | 7/2011 |
| WO | WO 2011/107480 A1 | 9/2011 |
| WO | WO 2011/109440 | 9/2011 |

OTHER PUBLICATIONS

Casset et al. Jul. 18, 2003, A peptide mimetic of an anti-CD4 monoclonal antibody by rational design, Biochem. Biophys. Res. Commun., 307(1):198-205.

Holm et al., Feb. 2007, Functional mapping and single chain construction of the anti-cytokeratin 8 monoclonal antibody TS1, Mol. Immunol. 44(6):1075-1084.

Li et al., 2002, Reduction of kidney uptake in radiometal labeled peptide linkers conjugated to recombinant antibody fragments, site-specific conjugation of DOTA-peptides to a Cys-diabody, Bioconjugate Chem., 13(5):985-995.

MacCallum et al., Oct. 11, 1996, Antibody-antigen interactions: Contact Analysis and Binding Site Topography, Journal of Molecular Biology, 262(5):732-745.

Verhaar et al., May 1996, Technetium-99m radiolabeling using a phage-derived single-chain Fv with a C-terminal cysteine, The Journal of Nuclear Medicine, 37(5):671-680.

Wu et al., Jan. 2009, Antibodies and antimatter: The Resurgence of Immuno-PET, The Journal of Nuclear Medicine, 50(1):2-5.

Wu et al., Sep. 2005, Arming antibodies: prospects and challenges for immunoconjugates, Nature Biotechnology, 23(9): 1137-1146.

Office Action dated Mar. 4, 2016 in U.S. Appl. No. 14/266,391.

Office Action dated Sep. 28, 2016 in U.S. Appl. No. 14/266,391.

Office Action dated Jun. 27, 2017 in U.S. Appl. No. 14/266,391.

(56) References Cited

OTHER PUBLICATIONS

Office Action dated Feb. 16, 2018 in U.S. Appl. No. 14/266,391.
Office Action dated Sep. 12, 2018 in U.S. Appl. No. 14/266,391.
Summons to attend oral proceedings dated Sep. 25, 2018 in European Patent Application No. 16191132.6.
U.S. Appl. No. 09/147,142 (also published as 2002/0018749), filed Mar. 5, 1999, Hudson et al.
U.S. Appl. No. 10/367,956 (also published as 2004/0071690), filed Feb. 19, 2003, Hudson et al.
U.S. Appl. No. 10/690,990, Wu et al.
U.S. Appl. No. 11/692,643 (also published as 2008/0152586), filed Mar. 28, 2007, Hudson et al.
U.S. Appl. No. 11/939,422 (also published as 2009/0238755), filed Sep. 24, 2009, Bander.
U.S. Appl. No. 12/293,860 (also published as 2009/0311181), filed Sep. 22, 2008, Wu.
U.S. Appl. No. 12/363,678 (also published as 2009/0275081), filed Jan. 30, 2009, Barat et al.
U.S. Appl. No. 12/413,435 (also published as 2009/0202548), filed Mar. 27, 2009, Gudas.
U.S. Appl. No. 12/537,145 (also published as 2010/0069616), filed Aug. 6, 2009, Wu et al.
U.S. Appl. No. 12/676,348 (also published as 2010/0297004), filed Aug. 5, 2010, Wu.
U.S. Appl. No. 12/788,477, filed May 27, 2010, Wu et al.
U.S. Appl. No. 12/959,230 (also published as 2012/0144110), filed Dec. 2, 2010, Smith.
U.S. Appl. No. 12/959,340 (also published as 2011/0268656), filed Dec. 2, 2010, Ho.
U.S. Appl. No. 13/094,730 (also published as 2011/0262968), filed Apr. 26, 2011, Gudas.
U.S. Appl. No. 13/554,306 (also published as 2012/0283418), filed Jul. 20, 2012, Wu et al.
Adams et al., "Highly specific in vivo tumor targeting by monovalent and divalent forms of 741F8 anti-c-erbB-2 single-chain Fv," Cancer Res., Sep. 1, 1993, pp. 4026-4034, vol. 53, No. 17.
Albrecht et al., "Development of anti-MUC1 di-scFvs for molecular targeting of epithelial cancers, such as breast and prostate cancers," Dec. 2007, pp. 304-313, vol. 51, No. 4.
Atwell et al., "scFv multimers of the anti-neuranminidase antibody NC10: length of the linker between VH and VL domains dictates precisely the transition between diabodies and triabodies," Protein Engineering, Jul. 1999, vol. 12, No. 7, pp. 597-604.
Bander et al., "Targeting Metastatic Prostate Cancer with Radiolabeled Monoclonal Antibody J591 to the Extracellular Domain of Prostate Specific Membrane Antigen", The Journal of Urology, Nov. 2003, vol. 170, pp. 1717-1721.
Bander et al., "Phase I trial of 177 Lutetium-labeled J591, a monoclonal antibody to prostate-specific membrane antigen, in patients with androgen-independent prostate cancer," Journal of Clinical Oncology, Jul. 20, 2005, pp. 4591-4601, vol. 23, No. 21.
Barat et al., "Cys-Diabody Quantum Dot Conjugates (ImmunoQdots) for Cancer Marker Detection," Bioconjug. Chem., Aug. 19, 2009, pp. 1474-1481, vol. 20(8).
Caldas et al., "Humanization of the Anti-CD18 Antibody 6.7: an unexpected effect of a framework residue in binding to antigen," Mol. Immunol. May 2003; 39 (15): 941-952.
Carmichael et al., "The crystal structure of an anti-CEA scFv diabody assembled from T84.66 scFvs in V(L)-to-V(H) orientation: Implications for diabody flexibility," J. Mol. Biol., Feb. 14, 2003, pp. 341-351, vol. 326, No. 2.
Carter et al., "Engineering antibodies for imaging and therapy", Curr. Opin. Biotechnol., Aug. 1997, vol. 8, No. 4, pp. 449-454.
Chang et al., "Prostate-Specific Membrane Antigen is Produced in Tumor-Associated Neovasculature1," Clin. Cancer Res., Oct. 1999, pp. 2674-2681, vol. 5.
Chien et al., "Significant Structural and Functional Change of an Antigen-Bidning Site by a Distant Amino Acid Substitution: Proposal of a Structural Mechanism," Proc. Natl. Acad. Sci. USA. Jul. 1989; 86 (14): 5532-5536.
Chothia et al., "Canonical structures for the hypervariable regions of immunoglobulins", Journal of Molecular Biology, vol. 196, Issue 4, Aug. 20, 1987, pp. 901-917.
City of Hope National Medical Center, "Anti-CEA antibody T84.66 humanized," Medical Imaging Law Weekly, copyright 2004, http://www.newsrx.com/newsletters/Medical-Imaging-Law-Weekly ; dated for online publication Nov. 27, 2004.
Communication pursuant to Rules 70(2) and 70a(2) EPC dated Dec. 28, 2010, received in EP Appl. No. 08799192.3, 11 pages.
Communication pursuant to Article 94(3) EPC dated Aug. 26, 2014 in European Application No. 10835159.4.
Communication pursuant to Article 94(3) EPC dated Nov. 10, 2014 in European Application No. 10835159.4.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol, 2002; 169 (6): 3076-3084.
Desplancq et al., "Multimerization behaviour of single chain Fv variants for the tumour-binding antibody B72.3," Protein Engineering, Aug. 1994, vol. 7, No. 8, pp. 1027-1033.
Extended European Search Report dated Jan. 18, 2017 in Application No. 16191132.6.
Fitzgerald et al., "Improved tumour targeting by disulphide stabilized diabodies expressed in Pichia pastoris," Protein Engineering, 1997, pp. 1221-1225, vol. 10, No. 10.
George et al., "Radiometal labeling of recombinant proteins by a genetically engineered minimal chelation site: technetium-99m coordination by single-chain Fv antibody fusion proteins through a C-terminal cysteinyl peptide," Proc. Natl. Acad. Sci. USA, Aug. 1995, vol. 92, No. 18, pp. 8358-8362.
Giusti et al., "Somatic Diversification of S107 from an Antiphosphocholine to an anti-DNA Autoantibody is due to a Single Base Changes in its Heavy Chain Variable Region," Proc. Natl. Acad. Sci. USA. May 1987; 84 (9): 2926-2930).
Glockshuber et al., "A comparison of strategies to stabilize immunoglobulin Fv-fragments," Biochemistry, 1990, pp. 1362-1367, vol. 29, No. 6.
Gu et al., "Biological activity and microPET imaging properties of chimeric and humanized anit-prostate stem cell antigen (PSCA) antibodies," Proc Amer Assoc Cancer Res., 2005, vol. 46, Abstract #696 [Retrieved on May 14, 2012], URL: http://aacrmeetingabstracts.org/cgi/content/abstract/2005/1/164-b.
Gussow et al. (Methods in Enzymology. 1991; 203: 99-121).
Hollinger et al., ""Diabodies": Small bivalent and bispecific antibody fragments," Proc. Natl. Acad. Sci. USA, Jul. 1993, pp. 6444-6448, vol. 90.
Hopp et al., "A Computer Program for Predicting Protein Antigenic Determinants," Molecular Immunology, 1983, pp. 483-489, vol. 20 (4).
Hu et al., "Minibody: A Novel engineered anti-carcinoembryonic antigen antibody fragment (Single-Chain Fv-CH3) which exhibits rapid, high-level targeting of xenografts1", Cancer Research, vol. 56, pp. 3055-3061 (Jul. 1, 1996).
Johnson et al., "Effector cell recruitment with novel Fv-based dual-affinity re-targeting protein leads to potent tumor cytolysis and in vivo B-cell depletion," J. Mol. Biol., Jun. 11, 2010, pp. 436-449, vol. 399, No. 3.
Kabat et al., "Sequences of Proteins of Immunological Interest", 5th ed., NIH Publication No. 91-3242, 1991.
Kim et al., "Anti-CD30 diabody-drug conjugates with potent antitumor activity," Mol. Cancer Ther., Aug. 2008, pp. 2486-2497, vol. 7, No. 8.
Kukis et al., "Effect of the extent of chelate substitution on the immunoreactivity and biodistribution of 2IT-BAT-Lym-1 immunoconjugates", Cancer Research, vol. 55, pp. 878-884 (Feb. 1, 1995).
Leung, S., "Engineering a unique glycosylation site for site-specific conjugation of haptens to antibody fragments," The Journal of Immunology, 1995, pp. 5919-5926, vol. 154.
Lewis et al., "An improved method for conjugating monoclonal antibodies with N-Hydroxysulfosuccinimidyl DOTA", Bioconjugate Chem, vol. 12, pp. 320-324 (2001).

(56) References Cited

OTHER PUBLICATIONS

Leyton et al., "Humanized radioiodinated minibody for imaging of prostate stem cell antigen-expressing tumors", Clinical Cancer Research, vol. 14 No. 22, pp. 7488-7496 (Nov. 15, 2008).
Li et al., "Improved biodistribution and radioimmunoimaging with poly(ethylene glycol)-DOTA-conjugated anti-CEA diabody," Bioconjug. Chem., Jan.-Feb. 2006, pp. 68-76, vol. 17, No. 1.
Li et al., "Mammalian Cell Expression of Dimeric Small Immune Proteins (SIP)," Protein Engineering vol. 10, No. 6 pp. 731-736, 1997.
Liu et al., "Constitutive and antibody-induced internalization of prostate-specific membrane antigen", Cancer Research, vol. 58, pp. 4055-4060 (Sep. 1, 1998).
Liu et al., "Monoclonal antibodies to the extracellular domain of prostate-specific membrane antigen also react with tumor vascular endothelium", Cancer Research, vol. 57, pp. 3629-3634 (Sep. 1, 1997).
Liu et al., "Prostate-Specific Membrane Antigen Retargeted Measles Virotherapy for the Treatment of Prostate Cancer", Prostate, Jul. 1, 2009, vol. 69, No. 10, pp. 1128-1141.
Mariuzza et al., "The Structural Basics of Antigen-Antibody Recognition," Annu. Rev. Biophys. Biophys. Chem. 1987; 16: 139-159.
Marty et al., "Production of functionalized single-chain Fv antibody fragments binding to the ED-B domain of the B-isoform of fibronectin in Pichia pastoris," Protein Expression and Purification, Feb. 2001, vol. 21, Issue 1, pp. 156-164.
McCartney et al., "Engineering disulfide-linked single-chain Fv dimers [(sFv')2] with improved solution and targeting properties: Anti-digoxin 26-10 (sFv')2 and anti-c-erbB-2 741F8 (sFv')2 made by protein folding and bonded through C-termincal cysteinyl peptides," Protein Eng., Mar. 1995, pp. 301-314, vol. 8, No. 3.
McCartney et al., Refolding of single-chain Fv with C-terminal cysteine (sFv); formation of disulfide-bonded homodimers of antic-A£ 'r/7B-2 and anti-digoxin sFv', Miami Short Rep., 1993, vol. 3, p. 91.
McDevitt, M. et al. An Particle Emmitting Antibody For Radioimmunotherapy of Prostate Acnecer, Cancer Research, vol. 60, pp. 6095-6100, (2000).
Milowsky et al., "Phase I Trial of yttrium-90-labeled anti-prostate-specific membrane antigen monoclonal antibody J591 for androgen-independent prostate cancer", Journal of Clinical Oncology, vol. 22 No. 13, pp. 2522-2531 (Jul. 1, 2004).
Milowsky et al., "Vascular targeted therapy with anti-prostate-specific membrane antigen monoclonal antibody J591 in advanced solid tumors", Journal of Clinical Oncology, vol. 25 No. 5, pp. 540-547 (Feb. 10, 2007).
Moore et al., "Application of dual affinity retargeting molecules to achieve optimal redirected T-cell killing B-cell lymphoma," Blood, Apr. 28, 2011, pp. 4542-4551, vol. 117, No. 17.
Morris et al., "Pilot trial of unlabeled and indium-111-labeled anti-prostate-specific membrane antigen antibody J591 for castrate metastatic prostate cancer", Clinical Cancer Research, vol. 11, pp. 7454-7461 (2005).
Nanus et al., "Clinical Use of Monoclonal Antibody HuJ591 Therapy: Targeting Prostate Specific Membrane Antigen", The Journal of Urology, vol. 170, pp. S84-S89, Dec. 2003.
Neumaier et al., "Cloning of the genes for T84.66, and antibody that has a high specificity and affinity for carcinoembryonic antigen, and expression of chimeric human/mouse T84.66 genes in myeloma and Chinese hamster ovary cells," Cancer Research, 1990, vol. 50, pp. 2128-2134.
Notice of Allowance dated Jan. 30, 2014 in U.S. Appl. No. 12/959,340.
Office Action dated Jun. 24, 2013 in Chinese Application No. 201080062988.4 (with English Translation).
Office Action dated Feb. 4, 2013 in U.S. Appl. No. 12/959,340.
Office Action dated Apr. 24, 2013 in Russian Application No. 2012123550/20 (035853) (English Translation).
Office Action dated Oct. 18, 2013 in U.S. Appl. No. 12/959,340.
Office Action dated Jan. 30, 2014 in Chinese Application No. 201080062988.4 with English Translation.
Office Action dated Mar. 5, 2014 in European Application No. 10835159.4.
Office Action dated Oct. 23, 2014 in Chinese Application No. 201080062988.4 with English Translation.
Office Action dated Dec. 8, 2014 in Mexican Application No. MX/a/2012/006301 with English Translation
Office Action dated Dec. 9, 2014 in Russian Application No. 2012123550 with English Translation.
Office Action dated Jan. 8, 2015 in Australian Application No. 2010325969.
Office Action dated Feb. 23, 2015 in Japanese Application No. 2012-542204 with English translation.
Office Action dated Mar. 13, 2015 in Mexican Application No. MX/a/2012/006301 with English translation.
Office Action dated May 7, 2015 in Russian Application No. 2012123550 with English Translation.
Office Action dated Oct. 26, 2015, received in Japanese Patent Application No. 2012-542204 (with English translation).
Office Action dated Aug. 4, 2016 in Russian Application No. 2012123550 with English Translation.
Office Action dated Oct. 27, 2016 in Canadian Application No. 2,782,333.
Office Action dated Nov. 16, 2016 in Mexican Application No. MX/a/2016/003128 with summary English Translation.
Office Action dated Jan. 4, 2017 in Japanese Application No. 2016-34045 with English Translation.
Office Action dated Mar. 27, 2017 in Japanese Application No. 2012-542204 with English Translation.
Office Action dated Jun. 9, 2017 in Mexican Application No. MX/a/2016/003128 with summary English Translation.
Office Action dated Nov. 1, 2017 in Canadian Application No. 2782333.
Office Action dated Dec. 28, 2017 in Chinese App. No. 201510333807.1.
Office Action dated Dec. 20, 2017 in European Application No. 16191132.6.
Office Action dated Mar. 6, 2018 in Indian Patent App. No. 5792/DELNP/2012.
Office Action dated Aug. 24, 2012 in U.S. Appl. No. 12/788,477, filed May 27, 2012 in 22 pages.
Olafsen et al., "Characterization of engineered anti-p185 HER-2 (scFv-CH3)2 antibody fragments (minibodies) for tumor targeting", Protein Engineering, Design & Selection, vol. 17 No. 4, pp. 315-323, Oxford University Press (2004).
Olafsen et al., "Covalent disulfide-linked anti-CEA diabody allows site-specific conjugation and radiolabeling for tumor targeting applications," Protein Eng. Des. Sel., Jan. 2004, pp. 21-27, vol. 17, No. 1.
Olafsen et al., "ImmunoPET imaging of B-cell lymphoma using 124I-anti-CD20 scFv dimers (diabodies)," Protein Eng. Des. Sel., Apr. 2010, pp. 243-249, vol. 23, No. 4.
Olafsen et al., "Recombinant anti-CD20 antibody fragments for small-animal PET imaging of B-Cell lymphomas", The Journal of Nuclear Medicine, vol. 50 No. 9, pp. 1500-1508 (Sep. 2009).
Olafsen et al., "Tunable pharmacokinetics: modifying the in vivo half-life of antibodies by directed mutagenesis of the Fc fragment", Nature Protocols, vol. 1 No. 4, pp. 2048-2060 (2006).
Olson et al., "Clinical trials of cancer therapies targeting prostate-specific membrane antigen", Reviews on Recent Clinical Trials, vol. 2, pp. 182-190 (2007).
Preliminary Amendment filed on Dec. 21, 2011 in U.S. Appl. No. 12/788,477, filed May 27, 2012 in 9 pages.
Raag et al., "Single-chain Fvs." FASEB J., Jan. 1995, vol. 9, No. 1, pp. 73-80.
Restriction Requirement dated Aug. 7, 2012 in U.S. Appl. No. 12/959,340.
Rudikoff et al., "Singe Amino Acid Substitution Altering Antigen-Binding Specificity," Proc. Natl. Acad. Sci. USA, Marcy 1982, pp. 1979-1983, vol. 79.
Sirk et al., "Site-specific, thiol-mediated conjugation of fluorescent probes to cysteine-modified diabodies targeting CD20 or HER2," Dec. 2008, pp. 2527-2534, vol. 19, No. 12.

(56) References Cited

OTHER PUBLICATIONS

Slovin, "Targeting novel antigens for prostate cancer treatment: focus on prostate-specific membrane antigen", NIH Public Access: Author Manuscript, Expert Opinon TherTargets, vol. 9 No. 3, pp. 561-570 (Jun. 2005).
Stimmel et al., Site-specific conjugation on serine → Cysteine variant monoclonal antibodies, The Journal of Biological Chemistry, Sep. 29, 2000, p. 30445-30450, vol. 275, No. 39.
Summons to attend oral proceedings dated Jul. 10, 2015 in European Patent Application No. 10835159.4.
Tai et al., "Targeting c-erbB-2 expressing tumors using single-chain Fv monomers and dimers," Cancer Res., Dec. 1, 1995, p. 5983s-5989s, vol. 55, No. 23 Suppl.
Urva et al., "Physiologically based pharmacokinetic (PBPK) model for T.84.66, a monoclonal anti-CEA antibody," Am. Assoc. Pharm. Sci. 10 (Supp. 2), 2008, p. 957.
Vaidyanathan et al., "Evaluation of an anti-p 185HER2 (scFv-CH2-CH2)2 fragment following radioiodination using two different residualizing labels: SGMIB and IB-Mal-D-GEEEK*," Nuclear Medicine and Biology, 2009, pp. 671-680, vol. 36.
Vajdos et al., "Comprehensive Functional Maps of the Antigen-binding Site of an Anti-ErbB2 Antibody Obtained with Shotgun Scanning Mutagenesis", J. Mol. Biol. (2002), vol. 320, pp. 415-428.
Veri et al., "Therapeutic control of B cell activation via recruitment of Fcgamma receptor IIb (CD32B) inhibitory function with a novel bispecific antibody scaffold," Arthritis Rheum., Jul. 2010, pp. 1933-1943, vol. 62, No. 7.
Viola-Villegas et al., "Noninvasive Imaging of PSMA in Prostate Tumors with 89 Zr-Labeled huJ591 Engineered Antibody Fragments: The Faster Alternatives", Molecular Pharmaceutics, vol. 11, No. 11, pp. 3965-3973, Nov. 3, 2014.
Whitlow et al., "Multivalent Fvs: characterization of single-chain Fv oligomers and preparation of a bispecific Fv," Protein Engineering, Aug. 1994, vol. 7, No. 8, pp. 1017-1026.
Winkler et al., Changing the Antigen Binding Specificity by Single Point Mutations of an Anti-p24 (HIV-1) Antibody, J. Immunol. Oct. 15, 2000; 165 (8): 4505-4514.
Wong et al., "Pilot trial evaluating an 123I-Labeled 80-Kilodalton engineered anticaroinoembryonic antigen antibody fragment (cT84.66 minibody) in patients with colorectal cancer", Clinical Cancer Research, vol. 10, pp. 5014-5021 (Aug. 1, 2004).
International Search Report and Written Opinion dated Mar. 21, 2012 for International Application No. PCT/US2010/058803, filed Dec. 2, 2010.
Written Opinion dated Apr. 22, 2009, from Int'l Appl. No. PCT/US2008/075291 (WO 2009/032949).
Written Opinion dated Apr. 23, 2008, from Int'l Appl. No. PCT/US2007/007020 (WO 2007/109321).
Wu et al., "Antibodies for molecular imaging of cancer", The Cancer Journal, vol. 14 No. 3, pp. 191-197 (May/Jun. 2008).
Wu et al., "Anti-carcinoembryonic antigen (CEA) diabody for rapid tumor targeting and imaging," Tumor Targeting, 1999, pp. 47-58, vol. 4.
Wu et al., "High-resolution microPET imaging of carcino-embryonic antigen-positive xenografts by using a copper-64-labeled engineered antibody fragment," Proc. Natl. Acad. Sci. USA, 2000, pp. 8495-8500, vol. 97, No. 15.
Wu et al., "Humanization of a Murine Monoclonal Antibody by Simultaneous Optimization of Framework and CDR Residues," J. Mol. Biol. Nov. 19, 1999; 294 (1): 151-162.
Wu et al., "Tumor localization of anti-CEA single-chain Fvs: Improved targeting by non-convalent dimmers," Immunotechnology, 1996, pp. 21-36, vol. 2.
Yamaguchi et al., "Development of a Sensitive Screening Method for Selecting Monoclonal Antibodies to be Internalized by Cells," Biochem. Biophys. Res. Common. Nov. 1, 2014; 454 (4): 600-603.
Yazaki et al., "Mammalian expression and hollow fiber bioreactor production of recombinant anti-CEA diabody and minibody for clinical applications," Journal of Immunological Methods, 2001, pp. 195-208, vol. 253.
Yazaki et al., "Tumor targeting of radiometal labeled anti-CEA recombinant T84.66 diabody and T84.66 minibody: Comparison to radioiodinated fragments," Bioconjugate Chem., 2001, pp. 220-228, vol. 12.
You et al., "Expression, purification, and characterization of a two domain carcinoembryonic antigen minigene (N-A3) in pichia pastoris the essential role of the N-domain," Anticancer Research, 1998, pp. 3193-3202, vol. 18.
File History, U.S. Appl. No. 08/256,156, filed Jun. 24, 1994.
File History, U.S. Appl. No. 08/838,682, filed Apr. 9, 1997.
File History, U.S. Appl. No. 08/895,914, filed Jul. 17, 1997.
File History, U.S. Appl. No. 09/357,707, filed Jul. 20, 1999.
File History, U.S. Appl. No. 09/357,708, filed Jul. 20, 1999.
File History, U.S. Appl. No. 09/357,709, filed Jul. 20, 1999.
File History, U.S. Appl. No. 09/929,546, filed Aug. 13, 2001.
File History, U.S. Appl. No. 09/357,704, filed Jul. 20, 1999.
File History, U.S. Appl. No. 10/160,505, filed May 30, 2002.
File History, U.S. Appl. No. 10/449,379, filed May 30, 2003.
File History, U.S. Appl. No. 10/690,990, filed Oct. 23, 2003.
File History, U.S. Appl. No. 11/219,563, filed Sep. 2, 2005.
File History, U.S. Appl. No. 11/218,813, filed Sep. 2, 2005.
File History, U.S. Appl. No. 12/293,860, filed Sep. 22, 2008.
File History, U.S. Appl. No. 12/363,678, filed Jan. 30, 2009.
File History, U.S. Appl. No. 12/371,399, filed Feb. 13, 2009.
File History, U.S. Appl. No. 12/537,145, filed Aug. 6, 2009.
File History, U.S. Appl. No. 12/676,348, filed Aug. 5, 2010.
File History, U.S. Appl. No. 12/788,477, filed May 27, 2010.
File History, U.S. Appl. No. 12/959,340, filed Dec. 2, 2010.
File History, U.S. Appl. No. 13/554,306, filed Jul. 20, 2012.
File History, U.S. Appl. No. 14/266,391, filed Apr. 30, 2014.

VH

(SEQ ID NO:3) Line 1  EVQLQSGGELKKPGSVISCKTSGYTFTEYTIHWVKQGALEWIGNINPNNGGTT
(SEQ ID NO:4) Line 2  EVQLQSGPELKKPGTSVRISCKTSGYTFTEYTIHWVKQSHGKSLEWIGNINPNNGGTT
(SEQ ID NO:5) Line 3  EVQLQSGPELKKPGMVISCKTSGYTFTEYTIHWVKQGKSLEWIGNINPNNGGTT (SEQ ID NO:3) Line 1  YNQKFEEIATLTVDKSSTAYMELSELAVYYCAAGWNFDYWGQGTTLTVSS
(SEQ ID NO:4) Line 2  YNQKFEDKATLTVDKSSTAYMELRSLTSEDSAVYYCAAGWNFDYWGQGTTLTVSS
(SEQ ID NO:5) Line 3  YNQKFEEDKATLTVDKSTAYMELSELAVYYCAAGWNFDYWGQGTLTVSS

VL

(SEQ ID NO:17) Line 1  DIVMTQSFVGDRVIICKASQDVGTAVDWYQQKPGKLLIYWASTRHTG
(SEQ ID NO:18) Line 2  DIVMTQSHKFMSTSVGDRVSIICKASQDVGTAVDWYQQKPGQSKLLIYWASTRHTG
(SEQ ID NO:19) Line 3  DIVMTQSTSVGDRVRKASQDVGTAVDWYQQKPGKLLIYWASTRHTG (SEQ ID NO:17) Line 1  VPDRFTGSGSGTDFTLTIHADIFCQQYNSYPLTFGTGK
(SEQ ID NO:18) Line 2  VPDRFTGSGSGTDFTLTINYQSEDLADYFCQQYNSYPLTFGAGTMLDLK
(SEQ ID NO:19) Line 3  SGSGSGTDFTLTIHADIFCQQYNSYPLTFGTGK

Fig. 2

Fig. 3A
J591 HC VHVL Minibody Translated Sequence (SEQ ID NOs:1 and 10)

```
tctagagccgccacc
XbaI Kozak
    1   M   E   T   D   T   L   L   L   W   V   L   L   L   W   V   P   G   S   T   G
    1   ATGGAAACCGACACCCTGCTGCTGTGGGTGCTGCTGCTCTGGGTCCCAGGCTCCACCGGT
        Signal Peptide
   21   E   V   Q   L   V   Q   S   G   A   E   V   K   K   P   G   A   S   V   K   I
   61   GAAGTGCAGCTGGTGCAGTCTGGCGCCGAAGTGAAGAAACCTGGCGCCTCCGTGAAGATC
        VH
   41   S   C   K   T   S   G   Y   T   F   T   E   Y   T   I   H   W   V   K   Q   A
  121   TCCTGCAAGACCTCCGGCTACACCTTCACCGAGTACACCATCCACTGGGTGAAACAGGCC 61   S   G   K   G   L   E   W   I   G   N   I   N   P   N   N   G   G   T   T   Y
  181   TCCGGCAAGGGCCTGGAATGGATCGGCAACATCAACCCTAACAACGGCGGCACCACCTAC 81   N   Q   K   F   E   D   R   A   T   L   T   V   D   K   S   T   S   T   A   Y
  241   AACCAGAAGTTCGAGGACCGGGCCACCCTGACCGTGGACAAGTCCACCTCCACCGCCTAC 101   M   E   L   S   S   L   R   S   E   D   T   A   V   Y   Y   C   A   A   G   W
  301   ATGGAACTGTCCTCCCTGCGGTCTGAGGACACCGCCGTGTACTACTGCGCCGCTGGCTGG 121   N   F   D   Y   W   G   Q   G   T   T   V   T   V   S   S   G   S   T   S   G
  361   AACTTCGACTACTGGGGCCAGGGCACCACAGTGACAGTCTCGAGCGGCTCTACCTCTGGC
                                                                        Linker
  141   G   G   S   G   G   G   S   G   G   G   G   S   S   D   I   V   M   T   Q   S
  421   GGAGGCTCTGGGGGAGGAAGCGGCGGAGGCGGCTCCTCTGACATCGTGATGACCCAGTCC
                                                                VL
  161   P   S   S   L   S   A   S   V   G   D   R   V   T   I   T   C   K   A   S   Q
  481   CCCTCCTCCCTGTCTGCCTCCGTGGGCGACAGAGTGACCATCACATGCAAGGCCTCCCAG 181   D   V   G   T   A   V   D   W   Y   Q   Q   K   P   G   K   A   P   K   L   L
  541   GATGTGGGCACCGCCGTGGACTGGTATCAGCAGAAGCCTGGCAAGGCCCCTAAGCTGCTG 201   I   Y   W   A   S   T   R   H   T   G   V   P   D   R   F   T   G   S   G   S
  601   ATCTACTGGGCCTCCACCAGACACACCGGCGTGCCTGACAGATTCACCGGCTCCGGCTCT 221   G   T   D   F   T   L   T   I   S   S   L   Q   P   E   D   F   A   D   Y   F
  661   GGCACCGACTTCACCCTGACCATCTCCAGCCTGCAGCCTGAGGACTTCGCCGACTACTTC 241   C   Q   Q   Y   N   S   Y   P   L   T   F   G   G   G   T   K   L   E   I   K
  721   TGCCAGCAGTACAACTCCTACCCTCTGACCTTCGGCGGAGGCACCAAGCTGGAAATCAAA 261   E   P   K   S   C   D   K   T   H   T   C   P   P   C   G   G   G   S   S   G
  781   GAGCCCAAGTCCTGCGACAAGACCCACACCTGTCCCCCTTGTGGCGGCGGATCTAGTGGC
        Hinge
  281   G   G   S   G   G   Q   P   R   E   P   Q   V   Y   T   L   P   P   S   R   D
  841   GGAGGATCCGGTGGCCAGCCTCGGGAGCCTCAGGTGTACACCCTGCCTCCCTCCCGGGAC
                            CH3
  301   E   L   T   K   N   Q   V   S   L   T   C   L   V   K   G   F   Y   P   S   D
  901   GAGCTGACCAAGAACCAGGTGTCCCTGACCTGTCTGGTCAAGGGCTTCTACCCTTCCGAT 321   I   A   V   E   W   E   S   N   G   Q   P   E   N   N   Y   K   T   T   P   P
  961   ATCGCCGTGGAGTGGGAGTCCAACGGCCAGCCTGAGAACAACTACAAGACCACCCCTCCT 341   V   L   D   S   D   G   S   F   F   L   Y   S   K   L   T   V   D   K   S   R
```

Fig. 3B

```
1021    GTGCTGGACTCCGACGGCTCCTTCTTCCTGTACTCCAAGCTGACAGTGGATAAGTCCCGG

361      W   Q   Q   G   N   V   F   S   C   S   V   M   H   E   A   L   H   N   H   Y
1081    TGGCAGCAGGGCAACGTGTTCTCCTGTTCCGTGATGCACGAGGCCCTGCACAACCACTAT

381      T   Q   K   S   L   S   L   S   P   G   K   -
1141    ACCCAGAAGTCCCTGTCCCTGTCTCCTGGCAAGTGA
                                                                STOP
aagctt
HinDIII
```

Fig. 4A
J591 2P VHVL Minibody Translated Sequence (SEQ ID NOs:2 and 11)
<u>TCTAGA</u>GCCGCCACC
<u>XbaI</u>

```
  1   M   E   T   D   T   L   L   W   V   L   L   L   W   V   P   G   S   T   G
  1   ATGGAAACCGACACCCTGCTGCTGTGGGTGCTGCTGCTCTGGGTCCCAGGCTCCACCGGT
      Signal Peptide
 21   E   V   Q   L   V   Q   S   G   P   E   V   K   K   P   G   A   T   V   K   I
 61   GAAGTGCAGCTGGTGCAGTCCGGCCCTGAAGTGAAGAAGCCTGGCGCCACCGTCAAGATC
      VH
 41   S   C   K   T   S   G   Y   T   F   T   E   Y   T   I   H   W   V   K   Q   A
121   TCTTGCAAGACCTCCGGCTACACCTTCACCGAGTACACCATCCACTGGGTGAAACAGGCC 61   P   G   K   G   L   E   W   I   G   N   I   N   P   N   N   G   G   T   T   Y
181   CCTGGCAAGGGTCTGGAATGGATCGGCAACATCAACCCTAACAACGGCGGCACCACCTAT 81   N   Q   K   F   E   D   K   A   T   L   T   V   D   K   S   T   D   T   A   Y
241   AACCAGAAGTTCGAGGACAAGGCCACCCTGACCGTGGACAAGTCCACCGACACCGCCTAC 101   M   E   L   S   S   L   R   S   E   D   T   A   V   Y   Y   C   A   A   G   W
301   ATGGAACTGTCCTCCCTCCGGTCCGAGGACACCGCAGTGTATTACTGCGCCGCTGGCTGG 121   N   F   D   Y   W   G   Q   G   T   L   L   T   V   S   S   G   S   T   S   G
361   AACTTCGACTACTGGGGCCAGGGCACCCTGCTGACAGTCTCGAGCGGCTCCACAAGTGGC
                                                              Linker
141   G   G   S   G   G   G   S   G   G   G   G   S   S   D   I   Q   M   T   Q   S
421   GGAGGCTCTGGCGGTGGATCTGGCGGAGGCGGCTCATCCGACATCCAGATGACCCAGTCC
                                              VL
161   P   S   S   L   S   T   S   V   G   D   R   V   T   L   T   C   K   A   S   Q
481   CCCTCCTCCCTGTCCACCTCCGTGGGCGACAGAGTGACCCTGACATGCAAGGCCTCCCAG 181   D   V   G   T   A   V   D   W   Y   Q   Q   K   P   G   Q   S   P   K   L   L
541   GACGTGGGCACCGCCGTGGACTGGTATCAGCAGAAGCCAGGCCAGTCCCCTAAGCTGCTG 201   I   Y   W   A   S   T   R   H   T   G   I   P   S   R   F   S   G   S   G   S
601   ATCTACTGGGCCTCCACCCGGCACACCGGCATCCCTTCCCGGTTCTCCGGCAGTGGCTCT 221   G   T   D   F   T   L   T   I   S   S   L   Q   P   E   D   F   A   D   Y   Y
661   GGCACCGACTTCACCCTGACCATCTCCAGCCTGCAGCCTGAGGACTTCGCCGACTACTAC 241   C   Q   Q   Y   N   S   Y   P   L   T   F   G   A   G   T   K   V   D   I   K
721   TGCCAGCAGTACAACTCCTACCCTCTGACCTTCGGCGCCGGCACAAAGGTGGACATCAAA 261   E   P   K   S   C   D   K   T   H   T   C   P   P   C   G   G   G   S   S   G
781   GAGCCTAAGTCCTGCGACAAGACCCACACATGTCCCCCTTGCGGCGGAGGAAGCAGCGGA
      Hinge                                        Extension
281   G   G   S   G   G   Q   P   R   E   P   Q   V   Y   T   L   P   P   S   R   D
841   GGC<u>GGATCC</u>GGTGGCCAGCCTCGGGAGCCTCAGGTGTACACCCTGCCTCCCTCCCGGGAC
                  CH3
301   E   L   T   K   N   Q   V   S   L   T   C   L   V   K   G   F   Y   P   S   D
901   GAGCTGACCAAGAACCAGGTGTCCCTGACCTGTCTGGTCAAGGGCTTCTACCCTTCCGAT 321   I   A   V   E   W   E   S   N   G   Q   P   E   N   N   Y   K   T   T   P   P
961   ATCGCCGTGGAGTGGGAGTCCAACGGCCAGCCTGAGAACAACTACAAGACCACCCCTCCT
```

Fig. 4B

```
341   V  L  D  S  D  G  S  F  F  L  Y  S  K  L  T  V  D  K  S  R
1021  GTGCTGGACTCCGACGGCTCCTTCTTCCTGTACTCCAAGCTGACAGTGGATAAGTCCCGG

361   W  Q  Q  G  N  V  F  S  C  S  V  M  H  E  A  L  H  N  H  Y
1081  TGGCAGCAGGGCAACGTGTTCTCCTGTTCCGTGATGCACGAGGCCCTGCACAACCACTAT

381   T  Q  K  S  L  S  L  S  P  G  K  -
1141  ACCCAGAAGTCCCTGTCCCTGTCTCCTGGCAAGTGA
                                         STOP
AAGCTT
HinDIII
```

Cys Diabody (Sirk S. et al, Bioconjugate Chem, 2008)

Figure 6 (SEQ ID NOs 6 and 12)

J591 CysDB Vh-5-Vl

```
  1    M   E   T   D   T   L   L   W   V   L   L   L   W   V   P   G   S   T   G
  1    ATGGAAACCGACACCCTGCTGCTGTGGGTGCTGCTCCTGTGGGTGCCCGGATCTACCGGT
       Signal
 21    E   V   Q   L   V   Q   S   G   A   E   V   K   K   P   G   A   S   V   K   I
 61    GAAGTGCAGCTGGTGCAGTCTGGCGCCGAAGTGAAGAAACCTGGCGCCTCCGTGAAGATC
       Vh
 41    S   C   K   T   S   G   Y   T   F   T   E   Y   T   I   H   W   V   K   Q   A
121    TCCTGCAAGACCTCCGGCTACACCTTCACCGAGTACACCATCCACTGGGTGAAACAGGCC 61    S   G   K   G   L   E   W   I   G   N   I   N   P   N   N   G   G   T   T   Y
181    TCCGGCAAGGGCCTGGAATGGATCGGCAACATCAACCCTAACAACGGCGGCACCACCTAC 81    N   Q   K   F   E   D   R   A   T   L   T   V   D   K   S   T   S   T   A   Y
241    AACCAGAAGTTCGAGGACCGGGCCACCCTGACCGTGGACAAGTCCACCTCCACCGCCTAC 101    M   E   L   S   S   L   R   S   E   D   T   A   V   Y   Y   C   A   A   G   W
301    ATGGAACTGTCCTCCCTGCGGTCTGAGGACACCGCCGTGTACTACTGCGCCGCTGGCTGG 121    N   F   D   Y   W   G   Q   G   T   T   V   T   V   S   S   S   G   G   G   G
361    AACTTCGACTACTGGGGCCAGGGCACCACCGTGACAGTCTCGAGCTCCGGTGGGGGCGGC
                                                                      Linker
141    D   I   V   M   T   Q   S   P   S   S   L   S   A   S   V   G   D   R   V   T
421    GATATCGTGATGACCCAGTCCCCTTCCTCCCTGTCTGCCTCCGTGGGCGACAGAGTGACC
       Vl
161    I   T   C   K   A   S   Q   D   V   G   T   A   V   D   W   Y   Q   Q   K   P
481    ATCACATGCAAGGCCTCCCAGGATGTGGGCACCGCCGTGGACTGGTATCAGCAGAAGCCT 181    G   K   A   P   K   L   L   I   Y   W   A   S   T   R   H   T   G   V   P   D
541    GGCAAGGCCCCTAAGCTGCTGATCTACTGGGCCTCCACCAGACACACCGGCGTGCCTGAC 201    R   F   T   G   S   G   S   G   T   D   F   T   L   T   I   S   S   L   Q   P
601    AGATTCACCGGCTCCGGCTCTGGCACCGACTTCACCCTGACCATCTCCAGCCTGCAGCCT 221    E   D   F   A   D   Y   F   C   Q   Q   Y   N   S   Y   P   L   T   F   G   G
661    GAGGACTTCGCCGACTACTTCTGCCAGCAGTACAACTCCTACCCTCTGACCTTCGGCGGA 241    G   T   K   L   E   I   K   G   G   C
721    GGCACCAAGCTGGAAATCAAGGGCGGTTGC
                                    Cys
```

Figure 7 (SEQ ID NOs 7 and 13)

J591 CysDB Vh-8-Vl

```
  1   M   E   T   D   T   L   L   W   V   L   L   L   W   V   P   G   S   T   G
  1   ATGGAAACCGACACCCTGCTGCTGTGGGTGCTGCTCCTGTGGGTGCCCGGATCTACCGGT
      Signal
 21   E   V   Q   L   V   Q   S   G   A   E   V   K   K   P   G   A   S   V   K   I
 61   GAAGTGCAGCTGGTGCAGTCTGGCGCCGAAGTGAAGAAACCTGGCGCCTCCGTGAAGATC
      Vh
 41   S   C   K   T   S   G   Y   T   F   T   E   Y   T   I   H   W   V   K   Q   A
121   TCCTGCAAGACCTCCGGCTACACCTTCACCGAGTACACCATCCACTGGGTGAAACAGGCC 61   S   G   K   G   L   E   W   I   G   N   I   N   P   N   N   G   G   T   T   Y
181   TCCGGCAAGGGCCTGGAATGGATCGGCAACATCAACCCTAACAACGGCGGCACCACCTAC 81   N   Q   K   F   E   D   R   A   T   L   T   V   D   K   S   T   S   T   A   Y
241   AACCAGAAGTTCGAGGACCGGGCCACCCTGACCGTGGACAAGTCCACCTCCACCGCCTAC 101   M   E   L   S   S   L   R   S   E   D   T   A   V   Y   Y   C   A   A   G   W
301   ATGGAACTGTCCTCCCTGCGGTCTGAGGACACCGCCGTGTACTACTGCGCCGCTGGCTGG 121   N   F   D   Y   W   G   Q   G   T   T   V   T   V   S   S   G   G   G   S   G
361   AACTTCGACTACTGGGGCCAGGGCACCACCGTGACAGTCTCGAGCGGCGGAGGGAGTGGC
                                                              Linker
141   G   G   G   D   I   V   M   T   Q   S   P   S   S   L   S   A   S   V   G   D
421   GGAGGCGGCGATATCGTGATGACCCAGTCCCCTTCCTCCCTGTCTGCCTCCGTGGGCGAC
                  Vl
161   R   V   T   I   T   C   K   A   S   Q   D   V   G   T   A   V   D   W   Y   Q
481   AGAGTGACCATCACATGCAAGGCCTCCCAGGATGTGGGCACCGCCGTGGACTGGTATCAG 181   Q   K   P   G   K   A   P   K   L   L   I   Y   W   A   S   T   R   H   T   G
541   CAGAAGCCTGGCAAGGCCCCTAAGCTGCTGATCTACTGGGCCTCCACCAGACACACCGGC 201   V   P   D   R   F   T   G   S   G   S   G   T   D   F   T   L   T   I   S   S
601   GTGCCTGACAGATTCACCGGCTCCGGCTCTGGCACCGACTTCACCCTGACCATCTCCAGC 221   L   Q   P   E   D   F   A   D   Y   F   C   Q   Q   Y   N   S   Y   P   L   T
661   CTGCAGCCTGAGGACTTCGCCGACTACTTCTGCCAGCAGTACAACTCCTACCCTCTGACC 241   F   G   G   G   T   K   L   E   I   K   G   G   C
721   TTCGGCGGAGGCACCAAGCTGGAAATCAAGGGCGGTTGC
                                        cys
```

Figure 8 (SEQ ID NOs 8 and 14)

J591 CysDB Vl-5-Vh

```
  1   M   E   T   D   T   L   L   W   V   L   L   L   W   V   P   G   S   T   G
  1   ATGGAAACCGACACCCTGCTGCTGTGGGTGCTGCTCCTGTGGGTGCCCGGATCTACCGGT
      Signal
 21   D   I   V   M   T   Q   S   P   S   S   L   S   A   S   V   G   D   R   V   T
 61   GATATCGTGATGACCCAGTCCCCTTCCTCCCTGTCTGCCTCCGTGGGCGACAGAGTGACC
      Vl
 41   I   T   C   K   A   S   Q   D   V   G   T   A   V   D   W   Y   Q   Q   K   P
121   ATCACATGCAAGGCCTCCCAGGATGTGGGCACCGCCGTGGACTGGTATCAGCAGAAGCCT 61   G   K   A   P   K   L   L   I   Y   W   A   S   T   R   H   T   G   V   P   D
181   GGCAAGGCCCCTAAGCTGCTGATCTACTGGGCCTCCACCAGACACACCGGCGTGCCTGAC 81   R   F   T   G   S   G   S   G   T   D   F   T   L   T   I   S   S   L   Q   P
241   AGATTCACCGGCTCCGGCTCTGGCACCGACTTCACCCTGACCATCTCCAGCCTGCAGCCT 101   E   D   F   A   D   Y   F   C   Q   Q   Y   N   S   Y   P   L   T   F   G   G
301   GAGGACTTCGCCGACTACTTCTGCCAGCAGTACAACTCCTACCCTCTGACCTTCGGCGGA 121   G   T   K   L   E   I   K   S   G   G   G   G   E   V   Q   L   V   Q   S   G
361   GGCACCAAGCTGGAAATCAAGTCCGGTGGGGGCGGCGAAGTGCAGCTGGTGCAGTCTGGC
                              Linker               Vh
141   A   E   V   K   K   P   G   A   S   V   K   I   S   C   K   T   S   G   Y   T
421   GCCGAAGTGAAGAAACCTGGCGCCTCCGTGAAGATCTCCTGCAAGACCTCCGGCTACACC 161   F   T   E   Y   T   I   H   W   V   K   Q   A   S   G   K   G   L   E   W   I
481   TTCACCGAGTACACCATCCACTGGGTGAAACAGGCCTCCGGCAAGGGCCTGGAATGGATC 181   G   N   I   N   P   N   N   G   G   T   T   Y   N   Q   K   F   E   D   R   A
541   GGCAACATCAACCCTAACAACGGCGGCACCACCTACAACCAGAAGTTCGAGGACCGGGCC 201   T   L   T   V   D   K   S   T   S   T   A   Y   M   E   L   S   S   L   R   S
601   ACCCTGACCGTGGACAAGTCCACCTCCACCGCCTACATGGAACTGTCCTCCCTGCGGTCT 221   E   D   T   A   V   Y   Y   C   A   A   G   W   N   F   D   Y   W   G   Q   G
661   GAGGACACCGCCGTGTACTACTGCGCCGCTGGCTGGAACTTCGACTACTGGGGCCAGGGC 241   T   T   V   T   V   S   S   G   G   C
721   ACCACCGTGACAGTCTCGAGCGGCGGTTGC
                                      Cys
```

Figure 9 (SEQ ID NOs 9 and 15)

J591 CysDB Vl-8-Vh

```
  1   M   E   T   D   T   L   L   W   V   L   L   L   W   V   P   G   S   T   G
  1   ATGGAAACCGACACCCTGCTGCTGTGGGTGCTGCTCCTGTGGGTGCCCGGATCTACCGGT
      Signal
 21   D   I   V   M   T   Q   S   P   S   S   L   S   A   S   V   G   D   R   V   T
 61   GATATCGTGATGACCCAGTCCCCTTCCTCCCTGTCTGCCTCCGTGGGCGACAGAGTGACC
      Vl
 41   I   T   C   K   A   S   Q   D   V   G   T   A   V   D   W   Y   Q   Q   K   P
121   ATCACATGCAAGGCCTCCCAGGATGTGGGCACCGCCGTGGACTGGTATCAGCAGAAGCCT 61   G   K   A   P   K   L   L   I   Y   W   A   S   T   R   H   T   G   V   P   D
181   GGCAAGGCCCCTAAGCTGCTGATCTACTGGGCCTCCACCAGACACACCGGCGTGCCTGAC 81   R   F   T   G   S   G   S   G   T   D   F   T   L   T   I   S   S   L   Q   P
241   AGATTCACCGGCTCCGGCTCTGGCACCGACTTCACCCTGACCATCTCCAGCCTGCAGCCT 101   E   D   F   A   D   Y   F   C   Q   Q   Y   N   S   Y   P   L   T   F   G   G
301   GAGGACTTCGCCGACTACTTCTGCCAGCAGTACAACTCCTACCCTCTGACCTTCGGCGGA 121   G   T   K   L   E   I   K   G   G   G   S   G   G   G   G   E   V   Q   L   V
361   GGCACCAAGCTGGAAATCAAGGGCGGAGGGAGTGGCGGAGGCGGCGAAGTGCAGCTGGTG
                                   Linker                     Vh
141   Q   S   G   A   E   V   K   K   P   G   A   S   V   K   I   S   C   K   T   S
421   CAGTCTGGCGCCGAAGTGAAGAAACCTGGCGCCTCCGTGAAGATCTCCTGCAAGACCTCC 161   G   Y   T   F   T   E   Y   T   I   H   W   V   K   Q   A   S   G   K   G   L
481   GGCTACACCTTCACCGAGTACACCATCCACTGGGTGAAACAGGCCTCCGGCAAGGGCCTG 181   E   W   I   G   N   I   N   P   N   N   G   G   T   T   Y   N   Q   K   F   E
541   GAATGGATCGGCAACATCAACCCTAACAACGGCGGCACCACCTACAACCAGAAGTTCGAG 201   D   R   A   T   L   T   V   D   K   S   T   S   T   A   Y   M   E   L   S   S
601   GACCGGGCCACCCTGACCGTGGACAAGTCCACCTCCACCGCCTACATGGAACTGTCCTCC 221   L   R   S   E   D   T   A   V   Y   Y   C   A   A   G   W   N   F   D   Y   W
661   CTGCGGTCTGAGGACACCGCCGTGTACTACTGCGCCGCTGGCTGGAACTTCGACTACTGG 241   G   Q   G   T   T   V   T   V   S   S   G   G   C
721   GGCCAGGGCACCACCGTGACAGTCTCGAGCGGCGGTTGC
                                           Cys
```

| Lane | Sample description | Reducing Agent (µl) | Sample (µl) | 4X LDS | Amount loaded on gel (µl) |
|---|---|---|---|---|---|
| 1 | Final product, 1:5 dilution | 0 | 22.5 | 7.5 | 25 |
| 2 | Final product, 1:5 dilution | 3 | 22.5 | 7.5 | 25 |
| 3 | Protein standards | 0 | 10 | 0 | 10 |

Fig. 23A 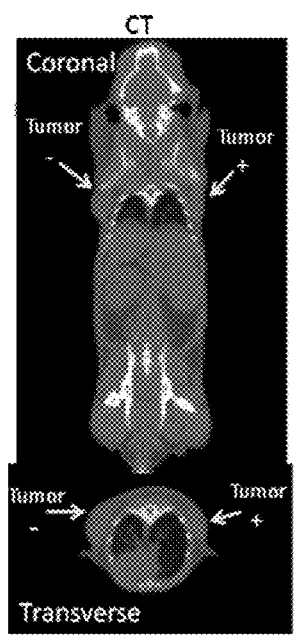 Fig. 23B 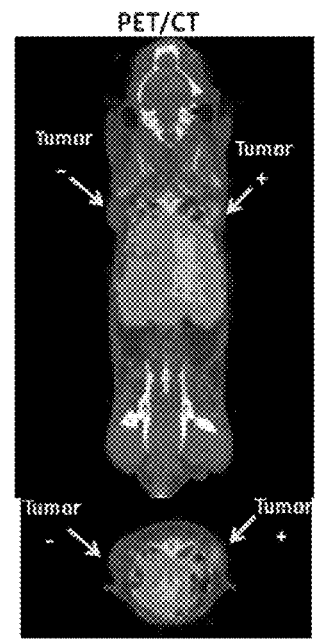
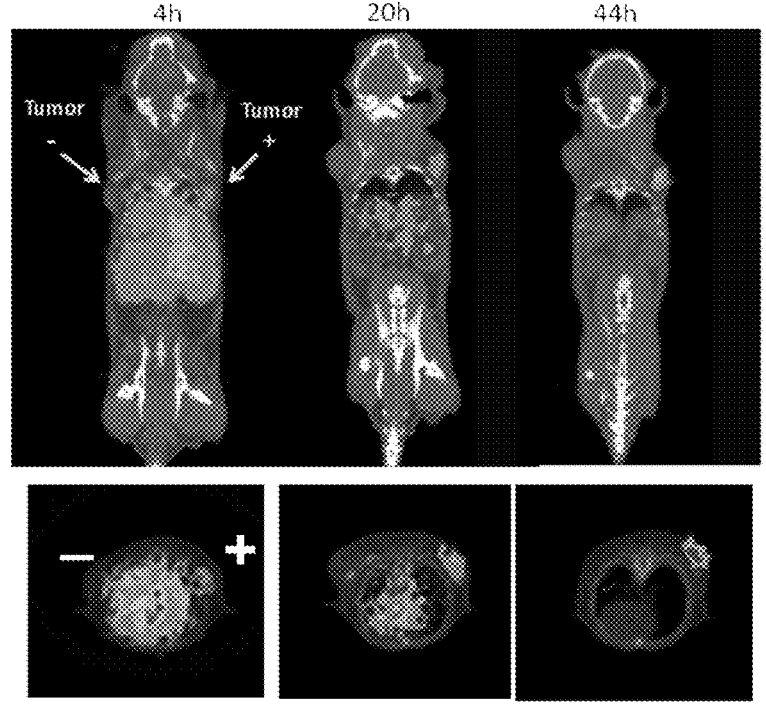
Fig. 23C

SEQUENCE LISTING

<160> NUMBER OF SEQ ID NOS: 19

<210> SEQ ID NO 1
<211> LENGTH: 1176
<212> TYPE: DNA
<213> ORGANISM: Artificial Sequence
<220> FEATURE:
<223> OTHER INFORMATION: J591 Human Composite VHVL Minibody nucleotide sequence

<400> SEQUENCE: 1

| | | |
|---|---|---|
| atggaaaccg acaccctgct gctgtgggtg ctgctgctct gggtcccagg ctccaccggt | 60 |
| gaagtgcagc tggtgcagtc tggcgccgaa gtgaagaaac ctggcgcctc cgtgaagatc | 120 |
| tcctgcaaga cctccggcta caccttcacc gagtacacca tccactgggt gaaacaggcc | 180 |
| tccggcaagg gcctggaatg gatcggcaac atcaaccctaa caacggcgg caccacctac | 240 |
| aaccagaagt tcgaggaccg ggccaccctg accgtggaca gtccacctc accgcctac | 300 |
| atggaactgt cctccctgcg gtctgaggac accgccgtgt actactgcgc cgctggctgg | 360 |
| aacttcgact actggggcca gggcaccaca gtgacagtct cgagcggctc tacctctggc | 420 |
| ggaggctctg ggggaggaag cggcggaggc ggctcctctg acatcgtgat gacccagtcc | 480 |
| ccctcctccc tgtctgcctc cgtgggcgac agagtgacca tcacatgcaa ggcctcccag | 540 |
| gatgtgggca ccgccgtgga ctggtatcag cagaagcctg gcaaggcccc taagctgctg | 600 |
| atctactggg cctccaccag acacaccggc gtgcctgaca gattcaccgg ctccggctct | 660 |
| ggcaccgact tcaccctgac catctccagc ctgcagcctg aggacttcgc cgactacttc | 720 |
| tgccagcagt acaactccta ccctctgacc ttcggcggag caccaagct ggaaatcaaa | 780 |
| gagcccaagt cctgcgacaa gacccacacc tgtcccccctt gtggcggcgg atctagtggc | 840 |
| ggaggatccg gtggccagcc tcgggagcct caggtgtaca ccctgcctcc ctcccgggac | 900 |
| gagctgacca gaaccaggt gtccctgacc tgtctggtca agggcttcta cccttccgat | 960 |
| atcgccgtgg agtgggagtc caacggccag cctgagaaca actacaagac caccectcct | 1020 |
| gtgctggact ccgacggctc cttcttcctg tactccaagc tgacagtgga taagtcccgg | 1080 |
| tggcagcagg gcaacgtgtt ctcctgttcc gtgatgcacg aggccctgca caaccactat | 1140 |
| acccagaagt ccctgtccct gtctcctggc aagtga | 1176 |

<210> SEQ ID NO 2
<211> LENGTH: 1176
<212> TYPE: DNA
<213> ORGANISM: Artificial Sequence
<220> FEATURE:
<223> OTHER INFORMATION: J591 2P VHVL Minibody nucleotide sequence

<400> SEQUENCE: 2

| | | |
|---|---|---|
| atggaaaccg acaccctgct gctgtgggtg ctgctgctct gggtcccagg ctccaccggt | 60 |
| gaagtgcagc tggtgcagtc cggccctgaa gtgaagaagc ctggcgccac cgtcaagatc | 120 |
| tcttgcaaga cctccggcta caccttcacc gagtacacca tccactgggt gaaacaggcc | 180 |
| cctggcaagg gtctggaatg gatcggcaac atcaaccctaa caacggcgg caccacctat | 240 |
| aaccagaagt tcgaggacaa ggccaccctg accgtggaca gtccaccga caccgcctac | 300 |
| atggaactgt cctccctccg gtccgaggac accgcagtgt attactgcgc cgctggctgg | 360 |
| aacttcgact actggggcca gggcaccctg ctgacagtct cgagcggctc cacaagtggc | 420 |
| ggaggctctg gcggtggatc tggcggaggc ggctcatccg acatccagat gacccagtcc | 480 |

```
cctcctccc tgtccacctc cgtgggcgac agagtgaccc tgacatgcaa ggcctcccag      540
gacgtgggca ccgccgtgga ctggtatcag cagaagccag gccagtcccc taagctgctg      600
atctactggg cctccacccg gcacaccggc atcccttccc ggttctccgg cagtggctct      660
ggcaccgact tcaccctgac catctccagc ctgcagcctg aggacttcgc cgactactac      720
tgccagcagt acaactccta ccctctgacc ttcggcgccg gcacaaaggt ggacatcaaa      780
gagcctaagt cctgcgacaa gacccacaca tgtcccccctt gcggcggagg aagcagcgga      840
ggcggatccg gtggccagcc tcgggagcct caggtgtaca ccctgcctcc ctcccgggac      900
gagctgacca agaaccaggt gtccctgacc tgtctggtca agggcttcta cccttccgat      960
atcgccgtgg agtgggagtc caacggccag cctgagaaca actacaagac caccccctcct    1020 gtgctggact ccgacggctc cttcttcctg tactccaagc tgacagtgga taagtcccgg    1080
tggcagcagg gcaacgtgtt ctcctgttcc gtgatgcacg aggccctgca caaccactat    1140
acccagaagt ccctgtccct gtctcctggc aagtga                              1176
```

<210> SEQ ID NO 3
<211> LENGTH: 115
<212> TYPE: PRT
<213> ORGANISM: Artificial Sequence
<220> FEATURE:
<223> OTHER INFORMATION: amino acid sequences of Human Composite J591
      V-regions (VH)

<400> SEQUENCE: 3

```
Glu Val Gln Leu Val Gln Ser Gly Ala Glu Val Lys Lys Pro Gly Ala
1               5                   10                  15

Ser Val Lys Ile Ser Cys Lys Thr Ser Gly Tyr Thr Phe Thr Glu Tyr
                20                  25                  30

Thr Ile His Trp Val Lys Gln Ala Ser Gly Lys Gly Leu Glu Trp Ile
            35                  40                  45

Gly Asn Ile Asn Pro Asn Asn Gly Gly Thr Thr Tyr Asn Gln Lys Phe
        50                  55                  60

Glu Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
                100                 105                 110

Val Ser Ser
        115
```

<210> SEQ ID NO 4
<211> LENGTH: 115
<212> TYPE: PRT
<213> ORGANISM: Mus musculus

<400> SEQUENCE: 4

```
Glu Val Gln Leu Gln Gln Ser Gly Pro Glu Leu Lys Lys Pro Gly Thr
1               5                   10                  15

Ser Val Arg Ile Ser Cys Lys Thr Ser Gly Tyr Thr Phe Thr Glu Tyr
                20                  25                  30

Thr Ile His Trp Val Lys Gln Ser His Gly Lys Ser Leu Glu Trp Ile
            35                  40                  45

Gly Asn Ile Asn Pro Asn Asn Gly Gly Thr Thr Tyr Asn Gln Lys Phe
        50                  55                  60
```

Glu Asp Lys Ala Thr Leu Thr Val Asp Lys Ser Ser Thr Ala Tyr
65                  70                  75                  80

Met Glu Leu Arg Ser Leu Thr Trp Glu Asp Ser Ala Val Tyr Tyr Cys
                85                  90                  95

Ala Ala Gly Trp Asn Phe Asp Tyr Trp Gly Gln Gly Thr Thr Leu Thr
            100                 105                 110

Val Ser Ser
        115

<210> SEQ ID NO 5
<211> LENGTH: 115
<212> TYPE: PRT
<213> ORGANISM: Artificial Sequence
<220> FEATURE:
<223> OTHER INFORMATION: amino acid sequences of deimmunized J591
      V-regions (VH)

<400> SEQUENCE: 5

Glu Val Gly Leu Val Gln Ser Gly Pro Glu Val Lys Lys Pro Gly Ala
1               5                   10                  15

Thr Val Lys Ile Ser Cys Lys Thr Ser Gly Tyr Thr Phe Thr Glu Tyr
            20                  25                  30

Thr Ile His Trp Val Lys Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Leu Thr
            100                 105                 110

Val Ser Ser
        115

<210> SEQ ID NO 6
<211> LENGTH: 750
<212> TYPE: DNA
<213> ORGANISM: Artificial Sequence
<220> FEATURE:
<223> OTHER INFORMATION: J591 cys-diabody (CysDB) VH-5-VL nucleotide
      sequence

<400> SEQUENCE: 6
atggaaaccg acaccctgct gctgtgggtg ctgctcctgt gggtgcccgg atctaccggt      60
gaagtgcagc tggtgcagtc tggcgccgaa gtgaagaaac ctggcgcctc cgtgaagatc     120
tcctgcaaga cctccggcta caccttcacc gagtacacca tccactgggt gaaacaggcc     180
tccggcaagg gcctggaatg gatcggcaac atcaacccta caacggcgg caccacctac      240 aaccagaagt tcgaggaccg ggccaccctg accgtggaca gtccacctc caccgcctac      300 atggaactgt cctccctgcg gtctgaggac accgccgtgt actactgcgc cgctggctgg     360
aacttcgact actggggcca gggcaccacc gtgacagtct cgagctccgg tggggcggc      420 gatatcgtga tgacccagtc cccttcctcc ctgtctgcct ccgtgggcga cagagtgacc     480
atcacatgca aggcctccca ggatgtgggc accgccgtgg actggtatca gcagaagcct     540
ggcaaggccc ctaagctgct gatctactgg gcctccacca gacacaccgg cgtgcctgac     600
agattcaccg gctccggctc tggcaccgac ttcaccctga ccatctccag cctgcagcct     660

```
gaggacttcg ccgactactt ctgccagcag tacaactcct accctctgac cttcggcgga      720
ggcaccaagc tggaaatcaa gggcggttgc                                        750

<210> SEQ ID NO 7
<211> LENGTH: 759
<212> TYPE: DNA
<213> ORGANISM: Artificial Sequence
<220> FEATURE:
<223> OTHER INFORMATION: J591 cys-diabody (CysDB) VH-8-VL nucleotide
      sequence

<400> SEQUENCE: 7
atggaaaccg acaccctgct gctgtgggtg ctgctcctgt gggtgcccgg atctaccggt       60
gaagtgcagc tggtgcagtc tggcgccgaa gtgaagaaac tggcgcctc cgtgaagatc       120 tcctgcaaga cctccggcta caccttcacc gagtacacca tccactgggt gaaacaggcc      180
tccggcaagg gcctggaatg gatcggcaac atcaaccta caacggcgg caccacctac        240 aaccagaagt tcgaggaccg gccaccctg accgtgaca agtccaccte caccgcctac        300 atggaactgt cctccctgcg gtctgaggac accgccgtgt actactgcgc cgctggctgg      360
aacttcgact actggggcca gggcaccacc gtgacagtct cgagcggcgg agggagtggc      420
ggaggcggcg atatcgtgat gacccagtcc ccttcctccc tgtctgcctc cgtgggcgac      480
agagtgacca tcacatgcaa ggcctccag gatgtgggca ccgccgtgga ctggtatcag       540
cagaagcctg gcaaggcccc taagctgctg atctactggg cctccaccag acacaccggc      600
gtgcctgaca gattcaccgg ctccggctct ggcaccgact tcaccctgac catctccagc      660
ctgcagcctg aggacttcgc cgactacttc tgccagcagt acaactccta ccctctgacc      720
ttcggcggag gcaccaagct ggaaatcaag ggcggttgc                             759

<210> SEQ ID NO 8
<211> LENGTH: 750
<212> TYPE: DNA
<213> ORGANISM: Artificial Sequence
<220> FEATURE:
<223> OTHER INFORMATION: J591 cys-diabody (CysDB) VL-5-VH nucleotide
      sequence

<400> SEQUENCE: 8
atggaaaccg acaccctgct gctgtgggtg ctgctcctgt gggtgcccgg atctaccggt       60
gatatcgtga tgacccagtc cccttcctcc ctgtctgcct ccgtgggcga cagagtgacc      120
atcacatgca aggcctccca ggatgtgggc accgccgtgg actggtatca gcagaagcct      180
ggcaaggccc ctaagctgct gatctactgg gcctccacca gacacaccgg cgtgcctgac      240
agattcaccg gctccggctc tggcaccgac ttcaccctga ccatctccag cctgcagcct      300
gaggacttcg ccgactactt ctgccagcag tacaactcct accctctgac cttcggcgga      360
ggcaccaagc tggaaatcaa gtccgtgggg ggcggcgaag tgcagctggt gcagtctggc      420
gccgaagtga agaaacctgg cgcctccgtg aagatctcct gcaagacctc cggctacacc      480
ttcaccgagt acaccatcca ctgggtgaaa caggcctccg gcaagggcct ggaatggatc      540
ggcaacatca accctaacaa cggcggcacc acctacaacc agaagttcga ggaccgggcc      600
accctgaccg tggacaagtc cacctccacc gcctacatgg aactgtcctc cctgcggtct      660
gaggacaccg ccgtgtacta ctgcgccgct ggctggaact tcgactactg gggccagggc      720
accaccgtga cagtctcgag cggcggttgc                                        750
```

<210> SEQ ID NO 9
<211> LENGTH: 759
<212> TYPE: DNA
<213> ORGANISM: Artificial Sequence
<220> FEATURE:
<223> OTHER INFORMATION: J591 cys-diabody (CysDB) VL-8-VH nucleotide sequence

<400> SEQUENCE: 9

```
atggaaaccg acaccctgct gctgtgggtg ctgctcctgt gggtgcccgg atctaccggt      60
gatatcgtga tgacccagtc cccttcctcc ctgtctgcct ccgtgggcga cagagtgacc     120
atcacatgca aggcctccca ggatgtgggc accgccgtgg actggtatca gcagaagcct     180
ggcaaggccc ctaagctgct gatctactgg gcctccacca gacacaccgg cgtgcctgac     240
agattcaccg gctccggctc tggcaccgac ttcaccctga ccatctccag cctgcagcct     300
gaggacttcg ccgactactt ctgccagcag tacaactcct accctctgac cttcggcgga     360
ggcaccaagc tggaaatcaa gggcggaggg agtggcggag cggcgaagt gcagctggtg      420
cagtctggcg ccgaagtgaa gaaacctggc gcctccgtga agatctcctg caagacctcc     480
ggctacacct tcaccgagta caccatccac tgggtgaaac aggcctccgg caagggcctg     540
gaatggatcg gcaacatcaa ccctaacaac ggcggcacca cctacaacca gaagttcgag     600
gaccgggcca ccctgaccgt ggacaagtcc acctccaccg cctacatgga actgtcctcc     660
ctgcggtctg aggacaccgc cgtgtactac tgcgccgctg gctggaactt cgactactgg     720
ggccagggca ccaccgtgac agtctcgagc ggcggttgc                            759
```

<210> SEQ ID NO 10
<211> LENGTH: 391
<212> TYPE: PRT
<213> ORGANISM: Artificial Sequence
<220> FEATURE:
<223> OTHER INFORMATION: J591 Human Composite VHVL Minibody amino acid sequence

<400> SEQUENCE: 10

```
Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Val Lys
            20                  25                  30

Lys Pro Gly Ala Ser Val Lys Ile Ser Cys Lys Thr Ser Gly Tyr Thr
        35                  40                  45

Phe Thr Glu Tyr Thr Ile His Trp Val Lys Gln Ala Ser Gly Lys Gly
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Arg Ala Thr Leu Thr Val Asp Lys Ser Thr
                85                  90                  95

Ser Thr Ala Tyr Met Glu Leu Ser Leu Arg Ser Glu Asp Thr Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Ser Thr Ser Gly Gly Gly Ser Gly
    130                 135                 140

Gly Gly Ser Gly Gly Gly Ser Ser Asp Ile Val Met Thr Gln Ser
145                 150                 155                 160

Pro Ser Ser Leu Ser Ala Ser Val Gly Asp Arg Val Thr Ile Thr Cys
```

```
                    165                 170                 175
Lys Ala Ser Gln Asp Val Gly Thr Ala Val Asp Trp Tyr Gln Gln Lys
            180                 185                 190

Pro Gly Lys Ala Pro Lys Leu Leu Ile Tyr Trp Ala Ser Thr Arg His
        195                 200                 205

Thr Gly Val Pro Asp Arg Phe Thr Gly Ser Gly Ser Gly Thr Asp Phe
    210                 215                 220

Thr Leu Thr Ile Ser Ser Leu Gln Pro Glu Asp Phe Ala Asp Tyr Phe
225                 230                 235                 240

Cys Gln Gln Tyr Asn Ser Tyr Pro Leu Thr Phe Gly Gly Gly Thr Lys
                245                 250                 255

Leu Glu Ile Lys Glu Pro Lys Ser Cys Asp Lys Thr His Thr Cys Pro
            260                 265                 270

Pro Cys Gly Gly Gly Ser Gly Gly Gly Ser Gly Gly Gly Ser Gln Pro Arg
        275                 280                 285

Glu Pro Gln Val Tyr Thr Leu Pro Pro Ser Arg Asp Glu Leu Thr Lys
    290                 295                 300

Asn Gln Val Ser Leu Thr Cys Leu Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Asp Ser Asp Gly Ser Phe Phe Leu Tyr Ser
            340                 345                 350

Lys Leu Thr Val Asp Lys Ser Arg Trp Gln Gln Gly Asn Val Phe Ser
        355                 360                 365

Cys Ser Val Met His Glu Ala Leu His Asn His Tyr Thr Gln Lys Ser
    370                 375                 380

Leu Ser Leu Ser Pro Gly Lys
385                 390

<210> SEQ ID NO 11
<211> LENGTH: 391
<212> TYPE: PRT
<213> ORGANISM: Artificial Sequence
<220> FEATURE:
<223> OTHER INFORMATION: J591 2P VHVL Minibody amino acid sequence

<400> SEQUENCE: 11

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Pro Glu Val Lys
            20                  25                  30

Lys Pro Gly Ala Thr Val Lys Ile Ser Cys Lys Thr Ser Gly Tyr Thr
        35                  40                  45

Phe Thr Glu Tyr Thr Ile His Trp Val Lys Gln Ala Pro Gly Lys Gly
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Lys Ala Thr Leu Thr Val Asp Lys Ser Thr
                85                  90                  95

Asp Thr Ala Tyr Met Glu Leu Ser Ser Leu Arg Ser Glu Asp Thr Ala
            100                 105                 110

Val Tyr Tyr Cys Ala Ala Gly Trp Asn Phe Asp Tyr Trp Gly Gln Gly
        115                 120                 125

Thr Leu Leu Thr Val Ser Ser Gly Ser Thr Ser Gly Gly Gly Ser Gly
```

```
                130              135              140
Gly Gly Ser Gly Gly Gly Ser Ser Asp Ile Gln Met Thr Gln Ser
145                 150              155              160

Pro Ser Ser Leu Ser Thr Ser Val Gly Asp Arg Val Thr Leu Thr Cys
                165              170              175

Lys Ala Ser Gln Asp Val Gly Thr Ala Val Asp Trp Tyr Gln Gln Lys
            180              185              190

Pro Gly Gln Ser Pro Lys Leu Leu Ile Tyr Trp Ala Ser Thr Arg His
        195              200              205

Thr Gly Ile Pro Ser Arg Phe Ser Gly Ser Gly Ser Gly Thr Asp Phe
210              215              220

Thr Leu Thr Ile Ser Ser Leu Gln Pro Glu Asp Phe Ala Asp Tyr Tyr
225              230              235              240

Cys Gln Gln Tyr Asn Ser Tyr Pro Leu Thr Phe Gly Ala Gly Thr Lys
                245              250              255

Val Asp Ile Lys Glu Pro Lys Ser Cys Asp Lys Thr His Thr Cys Pro
            260              265              270

Pro Cys Gly Gly Gly Ser Ser Gly Gly Gly Ser Gly Gly Gln Pro Arg
        275              280              285

Glu Pro Gln Val Tyr Thr Leu Pro Pro Ser Arg Asp Glu Leu Thr Lys
290              295              300

Asn Gln Val Ser Leu Thr Cys Leu Val Lys Gly Phe Tyr Pro Ser Asp
305              310              315              320

Ile Ala Val Glu Trp Glu Ser Asn Gly Gln Pro Glu Asn Asn Tyr Lys
                325              330              335

Thr Thr Pro Pro Val Leu Asp Ser Asp Gly Ser Phe Phe Leu Tyr Ser
            340              345              350

Lys Leu Thr Val Asp Lys Ser Arg Trp Gln Gln Gly Asn Val Phe Ser
        355              360              365

Cys Ser Val Met His Glu Ala Leu His Asn His Tyr Thr Gln Lys Ser
370              375              380

Leu Ser Leu Ser Pro Gly Lys
385              390

<210> SEQ ID NO 12
<211> LENGTH: 250
<212> TYPE: PRT
<213> ORGANISM: Artificial Sequence
<220> FEATURE:
<223> OTHER INFORMATION: J591 cys-diabody (CysDB) VH-5-VL amino acid
      sequence

<400> SEQUENCE: 12

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Val Lys
            20                  25                  30

Lys Pro Gly Ala Ser Val Lys Ile Ser Cys Lys Thr Ser Gly Tyr Thr
        35                  40                  45

Phe Thr Glu Tyr Thr Ile His Trp Val Lys Gln Ala Ser Gly Lys Gly
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Arg Ala Thr Leu Thr Val Asp Lys Ser Thr
                85                  90                  95
```

```
Ser Thr Ala Tyr Met Glu Leu Ser Ser Leu Arg Ser Glu Asp Thr Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Gly Asp Ile Val Met
    130                 135                 140

Thr Gln Ser Pro Ser Ser Leu Ser Ala Ser Val Gly Asp Arg Val Thr
145                 150                 155                 160

Ile Thr Cys Lys Ala Ser Gln Asp Val Gly Thr Ala Val Asp Trp Tyr
                165                 170                 175

Gln Gln Lys Pro Gly Lys Ala Pro Lys Leu Leu Ile Tyr Trp Ala Ser
            180                 185                 190

Thr Arg His Thr Gly Val Pro Asp Arg Phe Thr Gly Ser Gly Ser Gly
        195                 200                 205

Thr Asp Phe Thr Leu Thr Ile Ser Ser Leu Gln Pro Glu Asp Phe Ala
    210                 215                 220

Asp Tyr Phe Cys Gln Gln Tyr Asn Ser Tyr Pro Leu Thr Phe Gly Gly
225                 230                 235                 240

Gly Thr Lys Leu Glu Ile Lys Gly Gly Cys
                245                 250

<210> SEQ ID NO 13
<211> LENGTH: 253
<212> TYPE: PRT
<213> ORGANISM: Artificial Sequence
<220> FEATURE:
<223> OTHER INFORMATION: J591 cys-diabody (CysDB) VH-8-VL amino acid
      sequence

<400> SEQUENCE: 13

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Ala Glu Val Lys
            20                  25                  30

Lys Pro Gly Ala Ser Val Lys Ile Ser Cys Lys Thr Ser Gly Tyr Thr
        35                  40                  45

Phe Thr Glu Tyr Thr Ile His Trp Val Lys Gln Ala Ser Gly Lys Gly
    50                  55                  60

Leu Glu Trp Ile Gly Asn Ile Asn Pro Asn Asn Gly Gly Thr Thr Tyr
65                  70                  75                  80

Asn Gln Lys Phe Glu Asp Arg Ala Thr Leu Thr Val Asp Lys Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Ala Gly Trp Asn Phe Asp Tyr Trp Gly Gln Gly
        115                 120                 125

Thr Thr Val Thr Val Ser Ser Gly Gly Gly Ser Gly Gly Gly Asp
    130                 135                 140

Ile Val Met Thr Gln Ser Pro Ser Ser Leu Ser Ala Ser Val Gly Asp
145                 150                 155                 160

Arg Val Thr Ile Thr Cys Lys Ala Ser Gln Asp Val Gly Thr Ala Val
                165                 170                 175

Asp Trp Tyr Gln Gln Lys Pro Gly Lys Ala Pro Lys Leu Leu Ile Tyr
            180                 185                 190

Trp Ala Ser Thr Arg His Thr Gly Val Pro Asp Arg Phe Thr Gly Ser
        195                 200                 205
```

```
Gly Ser Gly Thr Asp Phe Thr Leu Thr Ile Ser Ser Leu Gln Pro Glu
        210                 215                 220

Asp Phe Ala Asp Tyr Phe Cys Gln Gln Tyr Asn Ser Tyr Pro Leu Thr
225                 230                 235                 240

Phe Gly Gly Gly Thr Lys Leu Glu Ile Lys Gly Gly Cys
                245                 250

<210> SEQ ID NO 14
<211> LENGTH: 250
<212> TYPE: PRT
<213> ORGANISM: Artificial Sequence
<220> FEATURE:
<223> OTHER INFORMATION: J591 cys-diabody (CysDB) VL-5-VH amino acid
      sequence

<400> SEQUENCE: 14

Met Glu Thr Asp Thr Leu Leu Leu Trp Val Leu Leu Leu Trp Val Pro
1               5                   10                  15

Gly Ser Thr Gly Asp Ile Val Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Gly Thr Ala Val Asp Trp Tyr Gln Gln Lys Pro Gly Lys Ala Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Ser Leu Gln Pro Glu Asp Phe Ala Asp Tyr Phe Cys Gln Gln Tyr Asn
            100                 105                 110

Ser Tyr Pro Leu Thr Phe Gly Gly Gly Thr Lys Leu Glu Ile Lys Ser
        115                 120                 125

Gly Gly Gly Gly Glu Val Gln Leu Val Gln Ser Gly Ala Glu Val Lys
    130                 135                 140

Lys Pro Gly Ala Ser Val Lys Ile Ser Cys Lys Thr Ser Gly Tyr Thr
145                 150                 155                 160

Phe Thr Glu Tyr Thr Ile His Trp Val Lys Gln Ala Ser Gly Lys Gly
                165                 170                 175

Leu Glu Trp Ile Gly Asn Ile Asn Pro Asn Asn Gly Gly Thr Thr Tyr
            180                 185                 190

Asn Gln Lys Phe Glu Asp Arg Ala Thr Leu Thr Val Asp Lys Ser Thr
        195                 200                 205

Ser Thr Ala Tyr Met Glu Leu Ser Ser Leu Arg Ser Glu Asp Thr Ala
    210                 215                 220

Val Tyr Tyr Cys Ala Ala Gly Trp Asn Phe Asp Tyr Trp Gly Gln Gly
225                 230                 235                 240

Thr Thr Val Thr Val Ser Ser Gly Gly Cys
                245                 250

<210> SEQ ID NO 15
<211> LENGTH: 253
<212> TYPE: PRT
<213> ORGANISM: Artificial Sequence
<220> FEATURE:
<223> OTHER INFORMATION: J591 cys-diabody (CysDB) VL-8-VH amino acid
      sequence

<400> SEQUENCE: 15
```

```
Met Glu Thr Asp Thr Leu Leu Leu Trp Val Leu Leu Leu Trp Val Pro
1               5                   10                  15

Gly Ser Thr Gly Asp Ile Val Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Gly Thr Ala Val Asp Trp Tyr Gln Gln Lys Pro Gly Lys Ala Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Ser Leu Gln Pro Glu Asp Phe Ala Asp Tyr Phe Cys Gln Gln Tyr Asn
            100                 105                 110

Ser Tyr Pro Leu Thr Phe Gly Gly Gly Thr Lys Leu Glu Ile Lys Gly
        115                 120                 125

Gly Gly Ser Gly Gly Gly Glu Val Gln Leu Val Gln Ser Gly Ala
    130                 135                 140

Glu Val Lys Lys Pro Gly Ala Ser Val Lys Ile Ser Cys Lys Thr Ser
145                 150                 155                 160

Gly Tyr Thr Phe Thr Glu Tyr Thr Ile His Trp Val Lys Gln Ala Ser
                165                 170                 175

Gly Lys Gly Leu Glu Trp Ile Gly Asn Ile Asn Pro Asn Asn Gly Gly
            180                 185                 190

Thr Thr Tyr Asn Gln Lys Phe Glu Asp Arg Ala Thr Leu Thr Val Asp
        195                 200                 205

Lys Ser Thr Ser Thr Ala Tyr Met Glu Leu Ser Ser Leu Arg Ser Glu
210                 215                 220

Asp Thr Ala Val Tyr Tyr Cys Ala Ala Gly Trp Asn Phe Asp Tyr Trp
225                 230                 235                 240

Gly Gln Gly Thr Thr Val Thr Val Ser Ser Gly Gly Cys
                245                 250

<210> SEQ ID NO 16
<211> LENGTH: 23
<212> TYPE: PRT
<213> ORGANISM: Homo sapiens

<400> SEQUENCE: 16

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 17
<211> LENGTH: 107
<212> TYPE: PRT
<213> ORGANISM: Artificial Sequence
<220> FEATURE:
<223> OTHER INFORMATION: amino acid sequences of Human Composite J591
      V-regions (VL)

<400> SEQUENCE: 17

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30
```

Val Asp Trp Tyr Gln Gln Lys Pro Gly Lys Ala Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Leu
                85                  90                  95

Thr Phe Gly Gly Gly Thr Lys Leu Glu Ile Lys
            100                 105

<210> SEQ ID NO 18
<211> LENGTH: 107
<212> TYPE: PRT
<213> ORGANISM: Mus musculus

<400> SEQUENCE: 18

Asp Ile Val Met Thr Gln Ser His Lys Phe Met Ser Thr Ser Val Gly
1               5                   10                  15

Asp Arg Val Ser Ile Ile Cys Lys Ala Ser Gln Asp Val Gly Thr Ala
            20                  25                  30

Val Asp Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Ala Gly Thr Met Leu Asp Leu Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: amino acid sequences of deimmunized J591
      V-regions (VL)

<400> SEQUENCE: 19

Asp Ile Gln Met Thr Gln Ser Pro Ser Ser Leu Ser Ser Val Gly
1               5                   10                  15

Asp Arg Val Thr Leu Thr Cys Lys Ala Ser Gln Asp Val Gly Thr Ala
            20                  25                  30

Val Asp Trp Tyr Gln Gln Lys Pro Gly Pro Ser Pro Lys Leu Leu Ile
            35                  40                  45

Tyr Trp Ala Ser Thr Arg His Thr Gly Ile Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Tyr Asn Ser Tyr Pro Leu
                85                  90                  95

Thr Phe Gly Pro Gly Thr Lys Val Asp Ile Lys
            100                 105

J591 MINIBODIES AND CYS-DIABODIES FOR TARGETING HUMAN PROSTATE SPECIFIC MEMBRANE ANTIGEN (PSMA) AND METHODS FOR THEIR USE

PRIORITY CLAIM

This application is a divisional of U.S. application Ser. No. 14/266,391, filed Apr. 30, 2014, now abandoned, which is a divisional of U.S. application Ser. No. 12/959,340, filed Dec. 2, 2010, now U.S. Pat. No. 8,772,459, which claims the benefit of U.S. Provisional Application No. 61/266,134, filed Dec. 2, 2009, each of which is hereby incorporated by reference as if fully set forth herein.

STATEMENT REGARDING FEDERALLY SPONSORED RESEARCH

This invention was made with government support under Contract No. HHSN261200900051C, awarded by the National Cancer Institute (NCI). The government has certain rights in the invention.

The present application is being filed along with a Sequence Listing in electronic format. The Sequence Listing is provided as a file entitled IGNAB007D2.TXT, created and last modified Feb. 12, 2019, which is 31,295 bytes in size. The information in the electronic format of the Sequence Listing is incorporated herein by reference in its entirety.

BACKGROUND

Advances in antibody engineering have enabled the development of various antibody fragments featuring different pharmacokinetic and binding properties (Wu et al 2005, Wu et al 2008, Wu et al 2009). A minibody is an antibody format which features a smaller molecular weight (.about.80 kD) than the full-length antibody while maintaining the bivalent binding property against an antigen (Hu et al 1996). Because of its smaller size, the minibody features faster clearance from the system and enhanced penetration when targeting tumor tissue. With the ability for strong targeting combined with rapid clearance, the minibody is an optimized antibody format that may be used for diagnostic imaging (Wu et al 2005). Since the discovery of the first minibody against the tumor-associated target CEA, many minibodies have been developed against different cancer targets for preclinical diagnostic imaging including human epidermal growth factor receptor-2 (HER2) in breast cancer, B-lymphocyte antigen CD20 in non-Hodgkins' lymphoma, and prostate stem cell antigen (PSCA) in prostate cancer (Hu et al 1996, Leyton et al 2008, Olafsen et al 2004, Olafsen et al 2009). For example, an $^{123}$I-labeled CEA minibody has been evaluated in the clinic for imaging patients with colorectal cancer by SPECT and similar studies have been performed with an $^{111}$In-DOTA labeled minibody (Wong et al 2004). The development of novel imaging agents is particularly critical for the diagnosis, management, and treatment of specific cancers which are poorly imaged with current technology such as prostate cancer.

The development of imaging agents for all types of cancer is needed to enable the targeting, staging, and monitoring of the disease. Current methods for diagnostic imaging of prostate cancer remain relatively inaccurate. With an estimated 234,460 new cases and 27,350 deaths in 2006, an imaging agent capable of accurately diagnosing, staging, and monitoring prostate cancer is needed (Olson et al 2007).

Prostate Specific Membrane Antigen (PSMA), a cell-surface biomarker that is associated with prostate cancer (Slovin 2005), is a single-pass Type II transmembrane protein possessing glutamate carboxypeptidase activity, although the functional role of PSMA is not well understood (Olson et al 2007). Expression of PSMA is relatively limited in normal tissues outside of the prostate including the brain, small intestines, liver, proximal kidney tubules, and salivary gland (Olson et al 2007).

PSMA expression in prostate cancer increases with tumor aggressiveness and is the highest in high-grade tumors, metastatic lesions, and androgen-independent disease (Olson et al 2007). Therefore, PSMA is a cancer biomarker that is a good candidate for targeting by an imaging agent. PSMA expression is also upregulated in the neovasculature of many non-prostatic solid tumors including lung, colon, breast, renal, liver and pancreatic carcinomas as well as sarcomas and melanoma (Olson et al 2007).

Full-length antibodies that target PSMA have been developed, some of which are in various stages of preclinical and clinical development (Olson et al 2007). PSMA was originally defined by a murine antibody (mAb), 7E11, which recognized an intracellular epitope of PSMA (Olson et al 2007). The 7E11 mAb was later developed into a FDA-approved SPECT imaging agent called Prostascint for the detection and imaging of prostate cancer in soft tissue (Olson et al 2007). However, since 7E11 recognizes an intracellular epitope, Prostascint is a relatively poor imaging agent which is limited to detecting necrotic tumor tissue (Olson et al 2007). Having the pharmacokinetic properties of a full-length antibody, Prostascint also requires a long period of time between injection and imaging (Olson et al 2007). Furthermore, Prostascint is a murine antibody which elicits strong immune responses that prevent multiple dosing (Olson et al 2007).

Another full-length antibody that targets PSMA, J591, was discovered and subsequently deimmunized, the deimmunized version known as huJ591 (Liu et al 1997, Bander et al 2003). The deimmunized huJ591 is an anti-human PSMA antibody that recognizes and binds an extracellular epitope on PSMA (Bander et al 2003). The huJ591 antibody is being developed as a potential radioimmunotherapy agent against prostate cancer. In Phase I trials, DOTA-conjugated huJ591 antibody labeled with gamma emitting isotopes Indium 111 and Lutetium 177 demonstrated excellent targeting to metastatic sites, no immunogenicity, and multiple doses were well tolerated (Bander et al 2003, Milowsky et al 2004, Bander et al 2005, Olson et al 2007). Beyond prostate cancer, Phase I studies with $^{111}$In-DOTA huJ591 demonstrated specific targeting of tumor neovasculature of advanced solid tumors (Milowsky et al 2007).

SUMMARY

In one embodiment, a minibody that binds PSMA is provided. According to this embodiment, the minibody is encoded by a nucleotide sequence comprising, from N-terminus to C-terminus, an scFv sequence that can bind prostate specific membrane antigen (PSMA), an artificial hinge sequence, and a human IgG1 CH3 sequence. The minibody monomer may also include an N-terminus signal sequence to enable secretion of the minibody when expressed in a cell.

The minibody scFv as described herein comprises a variable heavy domain (VH) linked to a variable light domain (VL) by a linker sequence. In one aspect, the scFv is in a VHVL orientation such that the VH is upstream of the VL. A minibody monomer having such an scFv may have a nucleotide sequence comprising SEQ ID NO:1 or SEQ ID NO:2. In another aspect, the scFv is in a VLVH orientation such that the VL is upstream of the VH.

The minibody monomer may be expressed by a cell. In such embodiments, a CysDB monomer expressed by a cell may include the amino acid sequence of SEQ ID NO:10 or SEQ ID NO:11.

In another embodiment, a cys-diabody (CysDB) that binds PSMA is provided. According to this embodiment, the CysDB monomer is encoded by a nucleotide sequence comprising, from N-terminus to C-terminus, an scFv sequence that can bind PSMA and a cysteine tail. The CysDB may also include an N-terminus signal sequence to enable secretion of the minibody when expressed in a cell.

The CysDB scFv as described herein comprises a variable heavy domain (VH) linked to a variable light domain (VL) by a linker sequence. In one aspect, the scFv is in a VHVL orientation such that the VH is upstream of the VL. A CysDB monomer having such an scFv may have a nucleotide sequence comprising SEQ ID NO:6 or SEQ ID NO:7. In another aspect, the scFv is in a VLVH orientation such that the VL is upstream of the VH. A CysDB monomer having such an scFv may have a nucleotide sequence comprising SEQ ID NO:8 or SEQ ID NO:9.

The CysDB may be expressed by a cell. In some embodiments, a CysDB expressed by a cell may include the amino acid sequence SEQ ID NO:12, SEQ ID NO:13, SEQ ID NO:14 or SEQ ID NO:15.

In another embodiment, a method for diagnosing a cancer associated with PSMA expression in a subject is provided. Such a method includes administering an anti-PSMA minibody or a cys-diabody conjugated to a diagnostic agent to a subject having or suspected of having a cancer associated with PSMA expression; exposing the subject to an imaging method to visualize the labeled minibody or cys-diabody in vivo; and determining that the subject has a cancer associated with PSMA expression when the labeled minibody or cys-diabody localizes to a tumor site.

In another embodiment, a method for treating a cancer associated with PSMA expression in a subject is provided. Such a method includes administering a therapeutically effective amount of a pharmaceutical composition to the subject, the composition comprising an anti-PSMA minibody or an anti-PSMA cys-diabody. In one aspect, the anti-PSMA minibody or anti-PSMA cys-diabody is conjugated to a therapeutic agent.

The cancer associated with PSMA expression in a subject may be lung cancer, colorectal cancer, breast cancer, renal cancer, liver cancer, bladder cancer, pancreatic cancer or melanoma.

A minibody that may be used in the methods as described above may be any suitable minibody as described herein, or may comprise SEQ ID NO:10 or SEQ ID NO:11. A cys-diabody that may be used in methods as described above may be any suitable minibody as described herein, or may comprise SEQ ID NO:12, SEQ ID NO:13, SEQ ID NO:14 or SEQ ID NO:15.

BRIEF DESCRIPTION OF THE DRAWINGS

FIG. 2 is a comparison between the amino acid sequences of deimmunized (Line 3; SEQ ID NO:5; SEQ ID NO:19), Murine (Line 2; SEQ ID NO:4; SEQ ID NO:18), and Human Composite (Line 1; SEQ ID NO:3; SEQ ID NO:17) J591 V-regions. Highlighted residues along the HC line (Line 1) designate differences between the HC and murine V-regions. Highlighted residues along the deimmunized line (Line 3) designate differences between the deimmunized and the murine V-regions as a result of the original deimmunization process. The two stars designate the two Prolines introduced by the deimmunization.

FIGS. 3A-3B are the J591 Human Composite VHVL Minibody nucleotide sequence (SEQ ID NO:1) and corresponding translated amino acid sequence (SEQ ID NO:10).

FIGS. 4A-4B are the J591 2P VHVL Minibody nucleotide sequence (SEQ ID NO:2) and corresponding translated amino acid sequence (SEQ ID NO:11).

FIG. 6 is the J591 cys-diabody (CysDB) VH-5-VL nucleotide sequence (SEQ ID NO:6) and corresponding translated amino acid sequence (SEQ ID NO:12).

FIG. 7 is the J591 cys-diabody (CysDB) VH-8-VL nucleotide sequence (SEQ ID NO:7) and corresponding translated amino acid sequence (SEQ ID NO:13).

FIG. 8 is the J591 cys-diabody (CysDB) VL-5-VH nucleotide sequence (SEQ ID NO:8) and corresponding translated amino acid sequence (SEQ ID NO:14).

FIG. 9 is the J591 cys-diabody (CysDB) VL-8-VH nucleotide sequence (SEQ ID NO:9) and corresponding translated amino acid sequence (SEQ ID NO:15).

FIG. 12A shows a graph representing the flow cytometry analysis for the J591 HO VLVH minibody, FIG. 12B shows a graph representing the flow cytometry analysis for the J591 HC VHVL minibody, FIG. 12C shows a graph representing the flow cytometry analysis for the J591 2P VLVH minibody, and FIG. 12D shows a graph representing the flow cytometry analysis for the J591 2P VHVL minibody.

FIGS. 23A-C illustrate representative serial microPET images of a mouse bearing CWR22rv1 and PC3 xenografts injected with $^{124}$I-J591 minibody. A representative mouse was serially scanned at multiple times postinjection. The CWR22rv1 tumor is depicted as the (+) tumor and the PC3 tumor as the (−) tumor. (A) CT scan at 4 hours post injection. Coronal and transverse planes are shown. (B) PET/CT overlay image at 4 hours postinjection. Coronal and transverse planes are shown. (C) Coronal PET/CT overlay images at 4, 20, and 44 hours postinjection.

DETAILED DESCRIPTION

Figure 1A:
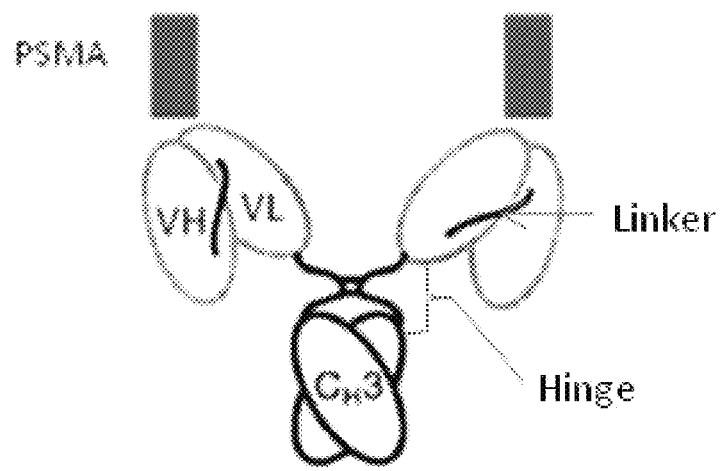
FIG. 1A is a schematic diagram of the J591 Minibody. This diagram depicts the minibody in the VHVL orientation binding the target PSMA.

The disclosure is directed to an antibody or functional antibody fragment that targets prostate specific membrane antigen (PSMA). The PSMA antibody or functional antibody fragment thereof may be conjugated to a substance such as a diagnostic agent, a therapeutic agent or a nanoparticle to form an anti-PSMA conjugate. Also disclosed are methods that include the use of the PSMA antibody, the functional PSMA antibody fragment or the anti-PSMA conjugate for diagnosing, visualizing, monitoring, or treating cancer or other conditions associated with overexpression of PSMA.

PSMA Antibodies and Functional Fragments Thereof

PSMA antibodies or a functional PSMA antibody fragments are provided herein according to the embodiments described herein. A PSMA antibody or functional antibody fragment is a molecule that includes one or more portions of an immunoglobulin or immunoglobulin-related molecule that specifically binds to, or is immunologically reactive with a PSMA. The term modified antibody includes, but is not limited to genetically engineered or otherwise modified forms of immunoglobulins, such as intrabodies, chimeric antibodies, fully human antibodies, humanized antibodies, and heteroconjugate antibodies (e.g., bispecific antibodies, diabodies, triabodies, and tetrabodies). The term functional antibody fragment includes one or more antigen binding fragments of antibodies alone or in combination with other molecules, including, but not limited to Fab', F(ab')$_2$, Fab, Fv, rIgG, scFv fragments, single domain fragments, peptibodies, minibodies and cys-diabodies. The term scFv refers to a single chain Fv antibody in which the variable domains of the heavy chain and of the light chain of a traditional two chain antibody have been joined to form one chain.

In one embodiment, the modified antibody or functional antibody fragment is an anti-PSMA minibody. In one embodiment, the anti-PSMA antibody is a J591 minibody. The anti-PSMA minibody has an anti-PSMA antibody fragment with optimized pharmacodynamic properties for in vivo imaging and biodistribution as described below. A "minibody" is a homodimer, wherein each monomer is a single-chain variable fragment (scFv) linked to a human IgG1 CH3 domain by a linker, such as ana hinge sequence. In one embodiment, the hinge sequence is a human IgG1 hinge sequence (EPKSCDKTHTCPPCPAPELLGGP; SEQ ID NO:16). In another embodiment, the hinge sequence is an artificial hinge sequence. The artificial hinge sequence may include a portion of a human IgG1 hinge and a GlySer linker sequence. In one embodiment, the artificial hinge sequence includes approximately the first 14 or 15 residues of the human IgG1 hinge followed by a GlySer linker sequence that is 8, 9 or 10 amino acids in length. In another embodiment, the artificial hinge sequence includes approximately the first 15 residues of the IgG1 hinge followed by a GlySer linker sequence that is 10 amino acids in length.

The scFv may have a VHVL or a VLVH orientation, wherein a VHVL orientation means that the variable heavy domain (VH) of the scFv is upstream from the variable light region (VL) and a VLVH orientation means that the VL of the scFv is upstream from the VH. As used herein, "upstream" means toward the N-terminus of an amino acid or toward the 5' end of a nucleotide sequence. The VH and VL are linked to each other by an amino acid linker sequence. The amino acid linker may be any suitable length. In one embodiment, the linker is Gly-Ser-rich and approximately 15-20 amino acids in length. In another embodiment, the linker is Cly-Ser rich and is 18 amino acids in length.

According to the embodiments described herein, each monomer of the anti-PSMA minibody may be encoded by a nucleotide sequence that includes the following elements, from N-terminus to C-terminus: (a) an scFv sequence that can bind PSMA, (b) an artificial hinge sequence, and (c) a human IgG CH3 sequence. The minibodies may be expressed by a cell, a cell line or other suitable expression system as described herein. Thus, a signal sequence may be fused to the N-terminus of the scFv to enable secretion of the minibody when expressed in the cell or cell line. In some embodiments, the nucleotide sequence is SEQ ID NO:1 or SEQ ID NO:2. When expressed by a cell or cell line, the nucleotide is transcribed and translated into an amino acid sequence. In some embodiments, the expressed amino acid sequence is SEQ ID NO:10 or SEQ ID NO:11.

In another embodiment, the modified antibody or functional antibody fragment is an anti-PSMA cys-diabody (CysDB) is provided. A "diabody" comprises a first polypeptide chain which comprises a heavy (VH) chain variable domain connected to a light chain variable domain (VL) on the first polypeptide chain (VH-VL) connected by a peptide linker that is too short to allow pairing between the two domains on the first polypeptide chain and a second polypeptide chain comprising a light chain variable domain (VL) linked to a heavy chain variable domain VH on the second polypeptide chain (VL-VH) connected by a peptide linker that is too short to allow pairing between the two domains on the second polypeptide chain. The short linkages force chain pairing between the complementary domains of the first and the second polypeptide chains and promotes the assembly of a dimeric molecule with two functional antigen binding sites. Therefore, a peptide linker may be any suitable length that promotes such assembly, for example, between 5 and 10 amino acids in length. As described further below, some cys-diabodies may include a peptide linker that is 5 or 8 amino acids in length. The anti-PSMA CysDB is a homodimer antibody format formed with two identical monomers that include single chain Fv (scFv) fragments with an approximate molecular weight of 55 kDa. In one embodiment, the anti-PSMA is a J591 CysDB. Like the anti-PSMA minibodies described above, the anti-PSMA CysDBs described herein have an anti-PSMA antibody fragment with optimized pharmacodynamic properties that may be used for in vivo imaging and biodistribution.

According to the embodiments described herein, each monomer of a CysDB may be encoded by a nucleotide sequence that includes the following elements, from N-terminus to C-terminus: (a) an scFv sequence that can bind PSMA and (b) a cysteine tail. The CysDBs may be expressed by a cell or a cell line as described herein. Thus, a signal sequence may be fused to the N-terminus of the scFv to enable secretion of the minibody when expressed in the cell or cell line. In some embodiments, the nucleotide sequence is SEQ ID NO:6, SEQ ID NO:7, SEQ ID NO:8 or SEQ ID NO:9. When expressed by a cell or cell line, the nucleotide is transcribed and translated into an amino acid sequence. In some embodiments, the expressed amino acid sequence is SEQ ID NO:12, SEQ ID NO:13, SEQ ID NO:14 or SEQ ID NO:15.

According to some embodiments, the CysDB scFv sequence is similar to the minibody scFv sequences described above scFv. Thus, the scFv may have a VHVL or a VLVH orientation, wherein a VHVL orientation means that the variable heavy domain (VH) of the scFv is upstream from the variable light region (VL) and a VLVH orientation means that the VL of the scFv is upstream from the VH. The antibody variable regions are linked together by a GlySer linker as described above. A Cysteine tail (Gly-Gly-Cys), is added at the C-terminus. This Cysteine tail allows the diabody complex to form covalent Cysteine bonds and provides the option for available sulfur residues for site-specific conjugation of functional moieties such as radiolabels.

Multiple CysDBs have been successfully engineered from various parental antibodies against different targets including CEA, Her2 (trastuzumab/Herceptin®), PSCA, and CD20 (rituximab/Rituxan®). Different variations of the CysDB format have been evaluated with four particular versions demonstrating the most promise with respect to binding and expression level. For each individual antibody, the heavy and light chain variable domains associate in different ways. For this reason, the use of different linker lengths allows for conformational flexibility and range-of-motion to ensure formation of the disulfide bonds. In some embodiments, the two linker length variants have either a 5 amino acid linker or an 8 amino acid linker. Each linker length variant may be developed using both orientations (VL-linker-VH-Cys tail and VH-linker-VL-Cys tail) to ensure the proper folding and stability is achieved. According to some embodiments, four CysDB variants that may be used in methods described herein have been constructed: VH5VL, VH8VL, VL5VH, and VL8VH (see FIGS. 6-9). Although each of the CysDB variants has been successfully expressed, results may vary depending on the parental antibody used. Producing and testing the expression and binding of all four variants ensures identification of an optimal format for protein production for each new CysDB. Evaluating the set of variants is important to ensure that a high-quality, stable protein is produced where the disulfide bridge is available. Therefore, engineering a CysDB actually involves using two distinct linker lengths, not one—as in the minibody, as well as both orientations of the variable regions, VH/VL and In some embodiments, a mammalian cell line (e.g., CHO-K1 cell line) may used as an expression system to produce the minibodies, cys-diabodies or other antibody fragments described herein. However, because the minibodies, cys-diabodies and other antibody fragments described herein are non-glycosylated, the cell line or expression, a mammalian expression system is not required, as such post-translational modifications are not needed. As such, a wide variety of mammalian and non-mammalian expression systems may be used to produce the PSMA antibody fragments (e.g., anti-PSMA minibodies and cys-diabodies) according to the embodiments of the disclosure including, but not limited to mammalian expression systems (e.g., CHO-K1 cells), bacterial expression systems (e.g., E. coli, B. subtilis) yeast expression systems (e.g., Pichia, S. cerevisiae) or any other known expression system.

As described in detail in the Examples below, four minibody variants that differ in the svFv region were made and expressed in CHO-K1 cells. Specific binding to PSMA was demonstrated by ELISA and flow cytometry. One of the variants with high expression and PSMA binding (J591 HC VHVL) was selected for protein production, purification and further evaluation. Protein production of the J591 HC VHVL minibody was successfully scaled-up to produce sufficient amounts for the internalization and microPET imaging experiments described below.

Confocal microscopy studies of the J591 minibody showed increased intracellular staining in CWR22rv1 and LNCaP cells over time, similar to that of the intact huJ591 mAb, suggesting that the J591 minibodies undergo rapid internalization. To further evaluate internalization of the J591 minibody, two radiolabeling strategies were employed: radioiodination with I-131 and DOTA conjugation for radiometal labeling with In-111. The $^{111}$In-DOTA J591 minibody showed a 260% increase in cell-associated radioactivity over a 3 hour time period In contrast, initial cell binding of $^{131}$I-J591 minibody was followed by a significant loss to 80% of the initial activity.

The J591 minibody is rapidly internalized upon binding to PSMA+ cell lines CWR22rv1 and LNCaP. For $^{131}$I-labeled J591 minibody, the total cell-associated radioactivity decreased over time suggesting loss of label likely attributed to dehalogenation and/or rapid metabolism and release from the cells of the $^{131}$I-J591 minibody. In contrast, the total cell-associated radioactivity of the $^{111}$In-DOTA-J591 minibody increased significantly over time (~2.5 fold) which is consistent with the residualizing label being trapped in the lysosomes. Based on the persistence of total cell-associated radioactivity over time, the residualizing In-DOTA radiolabeling strategy appeared to be the appropriate approach for in vivo imaging of the internalizing PSMA antigen.

Anti-PSMA Derivatives and Conjugates

In some embodiments, the PSMA antibodies or functional antibody fragments may include antibody derivatives that are modified. For example, the antibody derivatives include, but are not limited to, antibodies that have been modified by glycosylation, acetylation, pegylation, phosphorylation, amidation, derivatization by known protecting/blocking groups, proteolytic cleavage, and linkage to a cellular ligand or other protein. Any of numerous chemical modifications may be carried out by known techniques, including, but not limited to, specific chemical cleavage, acetylation, gormylation and metabolic synthesis of tunicamycin. Additionally, the derivative may contain one or more non-natural amino acids.

In other embodiments, the PSMA antibody or functional antibody fragment may be conjugated to another substance to form an anti-PSMA conjugate. The anti-PSMA conjugates described herein can be prepared by known methods of linking antibodies with lipids, carbohydrates, protein or other atoms and molecules. In one aspect, the anti-PSMA conjugate is formed by site-specific conjugation using a suitable linkage or bond. Site-specific conjugation is more likely to preserve the binding activity of an antibody or functional antibody fragment. The substance may be conjugated or attached at the hinge region of a reduced antibody component or antibody fragment via disulfide bond formation. For example, introduction of cysteine residues at the C-terminus of an scFv fragment, such as those introduce in the cys-diabodies described above, allows site-specific thiol-reactive coupling at a site away from the antigen binding site to a wide variety of agents. Alternatively, other linkages or bonds used to form the anti-PSMA conjugate may include, but is not limited to, a covalent bond, a non-covalent bond, a sulfide linkage, a hydrazone linkage, a hydrazine linkage, an ester linkage, an amido linkage, and amino linkage, an imino linkage, a thiosemicarbazone linkage, a semicarbazone linkage, an oxime linkage and a carbon-carbon linkage.

In one embodiment, the anti-PSMA conjugate may include a PSMA antibody or functional PSMA antibody fragment conjugated to a diagnostic agent. A "diagnostic agent" is an atom, molecule, or compound that is useful in diagnosing, detecting or visualizing a disease. According to the embodiments described herein, diagnostic agents may include, but are not limited to, radioactive substances (e.g., radioisotopes, radionuclides, radiolabels or radiotracers), dyes, contrast agents, fluorescent compounds or molecules, bioluminescent compounds or molecules, enzymes and enhancing agents (e.g., paramagnetic ions). In addition, it should be noted that some nanoparticles, for example quantum dots and metal nanoparticles (described below) may also be suitable for use as a detection agent.

Radioactive substances that may be used as diagnostic agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Sc, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as diagnostic agents in accordance with the embodiments of the disclosure include, but are not limited to, ions of transition and lanthanide metals (e.g. metals having atomic numbers of 6 to 9, 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

When the diagnostic agent is a radioactive metal or paramagnetic ion, the agent may be reacted with a reagent having a long tail with one or more chelating groups attached to the long tail for binding these ions. The long tail may be a polymer such as a polylysine, polysaccharide, or other derivatized or derivatizable chain having pendant groups to which may be bound to a chelating group for binding the ions. Examples of chelating groups that may be used according to the disclosure include, but are not limited to, ethylenediaminetetraacetic acid (EDTA), diethylenetriaminepentaacetic acid (DTPA), DOTA, NOTA, NETA, porphyrins, polyamines, crown ethers, bis-thiosemicarbazones, polyoximes, and like groups. The chelate is normally linked to the PSMA antibody or functional antibody fragment by a group which enables formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with the antibodies and carriers described herein. Macrocyclic chelates such as NOTA, DOTA, and TETA are of use with a variety of metals and radiometals including, but not limited to, radionuclides of gallium, yttrium and copper, respectively. Other ring-type chelates such as macrocyclic polyethers, which are of interest for stably binding nuclides, such as $^{223}$Ra for RAIT may be used. In certain embodiments, chelating moieties may be used to attach a PET imaging agent, such as an Al-$^{18}$F complex, to a targeting molecule for use in PET analysis.

Contrast agents that may be used as diagnostic agents in accordance with the embodiments of the disclosure include, but are not limited to, barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

Bioluminescent and fluorescent compounds or molecules and dyes that may be used as diagnostic agents in accordance with the embodiments of the disclosure include, but are not limited to, fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin or combination thereof.

Enzymes that may be used as diagnostic agents in accordance with the embodiments of the disclosure include, but are not limited to, horseradish peroxidase, alkaline phosphatase, acid phosphatase, glucose oxidase, β-galactosidase, β-glucuronidase or β-lactamase. Such enzymes may be used in combination with a chromogen, a fluorogenic compound or a luminogenic compound to generate a detectable signal.

In another embodiment, the anti-PSMA conjugate may include a PSMA antibody or functional PSMA antibody fragment conjugated to a therapeutic agent. A "therapeutic agent" as used herein is an atom, molecule, or compound that is useful in the treatment of cancer or other conditions associated with PSMA. Examples of therapeutic agents include, but are not limited to, drugs, chemotherapeutic agents, therapeutic antibodies and antibody fragments, toxins, radioisotopes, enzymes (e.g., enzymes to cleave prodrugs to a cytotoxic agent at the site of the tumor), nucleases, hormones, immunomodulators, antisense oligonucleotides, chelators, boron compounds, photoactive agents and dyes.

Chemotherapeutic agents are often cytotoxic or cytostatic in nature and may include alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that may be used as diagnostic agents in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, bacillus calmette-guerin (BOG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid.

Therapeutic antibodies and functional fragments thereof, that may be used as diagnostic agents in accordance with the embodiments of the disclosure include, but are not limited to, alemtuzumab, bevacizumab, cetuximab, edrecolomab, gemtuzumab, ibritumomab tiuxetan, panitumumab, rituximab, tositumomab, and trastuzumab Toxins that may be used as diagnostic agents in accordance with the embodiments of the disclosure include, but are not limited to, ricin, abrin, ribonuclease (RNase), DNase I, Staphylococcal enterotoxin-A, pokeweed antiviral protein, gelonin, diphtheria toxin, Pseudomonas exotoxin, and Pseudomonas endotoxin.

Radioisotopes that may be used as diagnostic agents in accordance with the embodiments of the disclosure include, but are not limited to, $^{32}P$, $^{89}Sr$, $^{90}Y$, $^{99m}Tc$, $^{99}Mo$, $^{131}I$, $^{153}Sm$, $^{177}Lu$, $^{186}Re$, $^{213}Bi$, $^{223}Ra$ and $^{225}Ac$.

In another embodiment, the anti-PSMA conjugate may include a PSMA antibody or functional PSMA antibody fragment conjugated to a nanoparticle. The term "nanoparticle" refers to a microscopic particle whose size is measured in nanometers, e.g., a particle with at least one dimension less than about 100 nm. Nanoparticles are particularly useful as detectable substances because they are small enough to scatter visible light rather than absorb it. For example, gold nanoparticles possess significant visible light extinction properties and appear deep red to black in solution. As a result, compositions comprising PSCA-specific antibody or fragments conjugated to nanoparticles can be used for the in vivo imaging of tumors or cancerous cells in a subject. At the small end of the size range, nanoparticles are often referred to as clusters. Metal, dielectric, and semiconductor nanoparticles have been formed, as well as hybrid structures (e.g. core-shell nanoparticles). Nanospheres, nanorods, and nanocups are just a few of the shapes that have been grown. Semiconductor quantum dots and nanocrystals are examples of additional types of nanoparticles. Such nanoscale particles, when conjugated to a PSMA antibody or functional antibody fragment, can be used as imaging agents for the in vivo detection of tumor cells as described above. Alternatively, nanoparticles can be used in therapeutic applications as drug carriers that, when conjugated to a PSCA-specific antibody or fragment of the present invention, deliver chemotherapeutic agents, hormonal therapeutic agents, radiotherapeutic agents, toxins, or any other cytotoxic or anticancer agent known in the art to cancerous cells that overexpress PSCA on the cell surface.

Any of the anti-PSMA conjugates described above may be further conjugated with one or more additional therapeutic agents, diagnostic agents, nanoparticles, carriers or a combination thereof. For example, a PSMA antibody or functional PSMA antibody fragment may be radiolabeled with $^{131}I$ and conjugated to a lipid carrier, such that the anti-PSMA-lipid conjugate forms a micelle. The micelle may incorporate one or more therapeutic or diagnostic agents. Alternatively, in addition to the carrier, the PSMA antibody or functional PSMA antibody fragment may be conjugated to $^{131}I$ (e.g., at a tyrosine residue) and a drug (e.g., at the epsilon amino group of a lysine residue), and the carrier may incorporate an additional therapeutic or diagnostic agent.

Methods for Diagnosing, Staging and Monitoring Cancer

The PSMA antibody, functional PSMA antibody fragment or anti-PSMA conjugate may be used to target a PSMA positive cell, such as cancer cells that overexpress PSMA. Therefore, methods for diagnosing, detecting, visualizing, monitoring or treating a cancer or other condition associated with PSMA expression may include administering the PSMA antibody, functional PSMA antibody fragment or anti-PSMA conjugate to a subject having or suspected of having a cancer or other condition associated with PSMA expression. As used herein, the term "subject" refers to any animal (e.g., a mammal), including but not limited to humans, non-human primates, rodents, dogs, pigs, and the like.

Cancers that are associated with PSMA expression may include those having cancer tumor tissue that overexpresses PSMA (e.g., prostate cancer) or those having solid tumor neovasculature that overexpresses PSMA (e.g., prostate cancer, lung cancer, colon (or colorectal) cancer, breast cancer, renal cancer, liver cancer, bladder cancer and pancreatic cancer as well as sarcomas and melanoma). Most solid tumor neovasculature expresses PSMA, making PSMA a neovasculature biomarker. Thus, in addition to cancer cells that expresses PSMA, a cancer that is associated with PSMA expression may include any cancer tissue with neovasculature including, but not limited to, carcinomas such as prostate cancer, lung cancer, colon (or colorectal) cancer, breast cancer, renal cancer, liver cancer, bladder cancer and pancreatic cancer as well as sarcomas and melanoma.

In one embodiment, a method for diagnosing, detecting, visualizing or monitoring a cancer associated with PSMA expression includes administering a diagnostic anti-PSMA conjugate to a subject having or suspected of having a cancer. The diagnostic anti-PSMA conjugate includes a PSMA antibody or a functional PSMA antibody fragment conjugated to one or more diagnostic agents as described above. In one embodiment, the PSMA antibody, or a functional PSMA antibody fragment is a minibody or a CysDB, derived from a J591 antibody such as those J591 minibodies and J591 CysDBs described herein. The diagnostic anti-PSMA conjugate may be conjugated to or associated with one or more additional substances described herein, such as a therapeutic anti-PSMA conjugate (as described below), unconjugated therapeutic agents, contrast solutions, carrier lipids or nanoparticles.

The diagnostic anti-PSMA conjugate used in the method described above is suitable for in vivo or in vitro detection or visualization methods. In one embodiment, an in vitro diagnostic or prognostic assay will be performed to determine the expression level of PSMA in a tissue sample taken from a subject having or suspected of having a cancer associated with PSMA as compared to a normal (i.e., non cancerous) or control tissue sample (i.e., known cancerous or benign tissue sample). Various assays for determining such express ion levels are contemplated and include immunohistochemistry, fluorescent in situ hybridization (FISH) and shed antigen assays, southern blotting, or FOR techniques.

In another embodiment, the diagnostic anti-PSMA conjugate may be used with an in vivo imaging modality to visualize the target cells within the topography of the subject's body. According to the method described herein, determining that the subject has a cancer associated with PSMA expression is accomplished by visualizing the labelled minibody or CysDB, wherein the visualized labeled minibody or CysDB localizes to a tumor site. In addition to diagnosing a cancer associated with PSMA expression, the PSMA minibody may also be used to stage, and monitor cancer progression according to method that are similar to those described above.

Suitable methods of in vivo imaging that may be used in accordance with the methods described herein include, but are not limited to, magnetic resonance imaging (MRI), positron emission tomography (PET) or microPET, computed tomography (CT), PET/CT combination imager, cooled charged coupled device (CCD), camera optical imaging, optical imaging (e.g., bioluminescent optical imaging, fluorescent optical imaging, or absorption of reflectance) and single photon emission computed tomography (SPECT), As described in the examples below, a minibody or CysDB as described herein that is labeled with an appropriate radioisotope (e.g., residualizing $^{124}$I, $^{64}$Cu-DOTA or $^{89}$Zr-DOTA), may be used as a clinical imaging agent to target PSMA in vivo according to the methods described herein. These J591 minibodies and CysDBs may also be developed as a potential single photon emission computed tomography (SPECT) imaging agent according to embodiments described herein. The J591 minibody may be used as a SPECT imaging agent by changing the radiolabel, for example, $^{111}$In-DOTA-J591.

The J591 minibodies described herein were evaluated for tumor targeting by small-animal PET (microPET) and biodistribution experiments following radiolabeling with the positron emitters I-124 ($t_{1/2}$=4.2 d) and Cu-64 ($t_{1/2}$=12.7 h) to compare retention of cell-associated radioactivity in vivo.

Both $^{124}$I and $^{64}$Cu-DOTA labelled J591 minibodies rapidly targeted the CWR22rv1 tumor with high uptake and specificity. Serial imaging of mice carrying PSMA positive CWR22rv1 and negative PC-3 xenografts resulted in high contrast images and excellent tumor uptakes with both labels. At 19 hours p.i., 8.2(±1.2) % ID/g and 8.8(±2.0) % ID/g were achieved with $^{64}$Cu-DOTA- and $^{124}$I-J591 minibodies, respectively. At 43 hours post injection (p.i.), tumor uptake increased to 13.3(±8.3) % ID/g with the $^{64}$Cu-DOTA-J591 minibodies, which declined to 3.25(±0.9) % ID/g with the $^{124}$I-J591 minibodies. Positive to negative tumor ratios were 3.1 and 4.9 at 19 hours and 5.4 and 7.3 at 43 hours for $^{64}$Cu-DOTA- and $^{124}$I-J591 minibodies, respectively. Persistent high liver uptake [21.4(±3.1) % ID/g at 19 hr and 14.4(±2.1) % ID/g at 43 hr] was seen with $^{64}$Cu-DOTA-J591 minibodies, whereas the $^{124}$I-J591 minibodies exhibited rapid background clearance resulting in higher contrast images. The similar tumor uptakes of both radiolabeled minibodies at 19 hours were unexpected, and suggestive of slower in vivo internalization. Thus, the J591 minibodies radiolabeled with I-124 is an efficient tracer for detecting PSMA positive cells.

Methods for Treating Cancer

In some embodiments, methods for treating cancer or other condition associated with overexpression of PSMA are provided. Such methods include administering to a subject a therapeutically effective amount of a pharmaceutical composition that includes a PSMA antibody, or a functional PSMA antibody fragment as described above. In one embodiment, the PSMA antibody, or a functional PSMA antibody fragment is a minibody or a CysDB, derived from a J591 antibody such as those J591 minibodies and J591 CysDBs described herein.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

A "therapeutically effective amount" or a: "therapeutically effective dose is an amount of a compound that produces a desired therapeutic effect in a subject, such as preventing or treating a target condition or alleviating symptoms associated with the condition. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

In one embodiment, the pharmaceutical composition may include a therapeutic anti-PSMA conjugate, wherein the conjugate includes a PSMA antibody or a functional PSMA antibody fragment conjugated to one or more therapeutic agent as described above. In one embodiment, the PSMA antibody, or a functional PSMA antibody fragment is a minibody or a CysDB, derived from a J591 antibody such as those J591 minibodies and J591 CysDBs described herein. For example, the J591 minibodies or cys-diabodies described herein may be used in a radioimmunotherapy approach, wherein one or more of the 3B J591 minibodies is radiolabeled with an appropriate beta-emitting radiolabel such as Yttrium-90. The radiolabeled 3B J591 minibody or minibodies may be used to deliver cell damage and death to local cancerous tissue that expresses PSMA. Further, the use of radiolabeled J591 minibodies and cys-diabodies would likely exhibit improved tumor penetration as compared to radiolabeled full-length parental huJ591 antibody.

The therapeutic anti-PSMA conjugate may be conjugated to or associated with one or more additional substances described herein, such as diagnostic anti-PSMA conjugates (described above), unconjugated diagnostic agents, contrast solutions, carrier lipids or nanoparticles.

In some embodiments, the pharmaceutical composition may also include a pharmaceutically acceptable carrier. A pharmaceutically acceptable carrier may be a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The pharmaceutical compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

Example 1: Generation of the J591 Minibodies

J591 Minibody Construct.

Figure 1B:
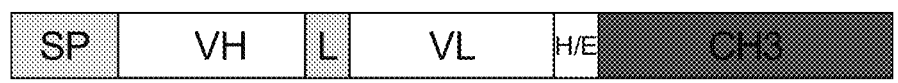
FIG. 1B is a schematic diagram of an expression construct for the J591 minibody in VHVL orientation. SP=signal peptide, VH—variable heavy domain, VL—variable light domain, L—18 amino acid linker, H./E—artificial hinge/extension, CH3 from human IgG1.
Figure 5A:
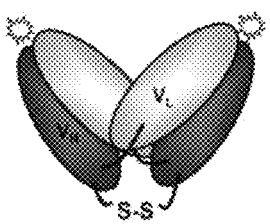
FIGS. 5A-5C are a schematic diagram of the cys-diabody (CysDB) (A), a schematic diagram of an expression construct for a CysDB in VLVH orientation (B), and a schematic diagram of an expression construct for a CysDB in VHVL orientation (C). SS=signal sequence, VH=variable heavy domain, VL=variable light domain, L linker (may be 5 or 8 amino acids), GGS=cysteine tail (Gly-Gly-Cys).
Figure 5B:
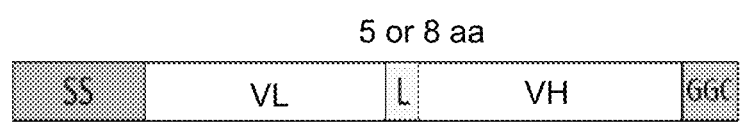
Figure 5C:
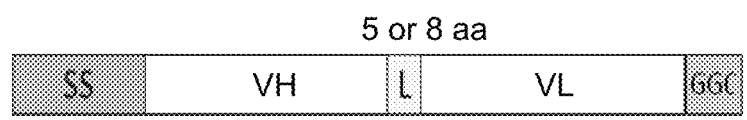

Third generation J591 minibodies are engineered antibody fragments that incorporate modified variable regions of the full-length parental huJ591 antibody. The minibody format is a homodimer wherein each monomer is a single-chain variable fragment (scFv) linked to a human IgG1 CH3 domain (FIG. 1A). The scFv can have a VHVL or a VLVH orientation. As shown in FIG. 1B, the J591 minibody expression construct for a an scFv having a VHVL orientation has a variable heavy (VH) domain that is linked to a variable light (VL) region by an 18 amino acid linker (L) sequence. In a VLVH orientation, the VL and VH would be switched in FIG. 1B such that the VL region is upstream of the VH domain.

Four J591 minibody sequences were synthesized for use in the expression studies described below: The minibody sequences that were constructed as follows:
1) J591 Human Composite (HC) with a VHVL orientation (J591 HC VHVL; SEQ ID NO:1);
2) J591 Human Composite (HC) with a VLVH orientation (J591 HC VLVH);
3) J591 with the 2 Proline substitutions (2P) with a VHLV orientation (J591 2P VHVL; SEQ ID NO:2); and
4) J591 with the 2 Praline substitutions (2P) with a VLVH orientation (J591 2P VLVH).

FIG. 3 shows the sequence of the J591 HC VHVL minibody (SEQ ID NO:1) and FIG. 4 shows the sequence of the J591 2P VHVL minibody (SEQ ID NO:2). The 18 amino acid linker (L) has a specific sequence of GlySer-rich residues (see FIG. 1, for sequence see FIGS. 3 and 4). The scFv is tethered to the human IgG1 CH3 domain by an artificial hinge sequence wherein the first 15 residues are that of the human IgG1 hinge followed by a 10 amino acid GlySer linker sequence (see FIG. 1, for sequence see FIGS. 3 and 4). This specific hinge sequence has also been successfully incorporated into previous minibodies. The minibody (either VH-VL-CH3 or VL-VH-CH3 orientation) exists as a stable dimer due to the association between the CH3 domains as well as the formation of disulfide bonds within the hinge regions. To enable secretion of the minibody, a kappa light chain signal sequence leads the expression construct and fused at the N-terminus of the variable heavy domain (see FIG. 1B, for sequence see FIGS. 3 and 4).

A set of J591 minibodies were engineered by making amino acid substitutions in the parental huJ591 variable heavy and light domains. Sequence analysis of the full length parental huJ591 variable regions identified an unusually high number of conformationally restrictive Proline residues, which are recognized to decrease the flexibility of protein structure. A comparison of sequence alignment between the deimmunized J591 (SEQ ID NO:5; SEQ ID NO:19) and the original murine J591 (SEQ ID NO:4; SEQ ID NO:18) revealed that the deimmunization process introduced additional Praline residues (see FIG. 2). After sequence and protein modeling analysis, two changes to the protein were made to improve the flexibility and folding ability. First, two Proline residues were changed in the variable light domain (P42Q and P100A) to the residues found in the murine sequence (see FIG. 2, here forth referred to as 2P). Second, substitutions were calculated for both variable regions using Human Composite (HC) Antibody technology (Antitope) that deimmunizes the sequence by avoiding potential epitopes instead of destroying epitopes (see FIG. 2, here forth referred to as HC).

Expression of the J591 Minibodies.

Figure 10:
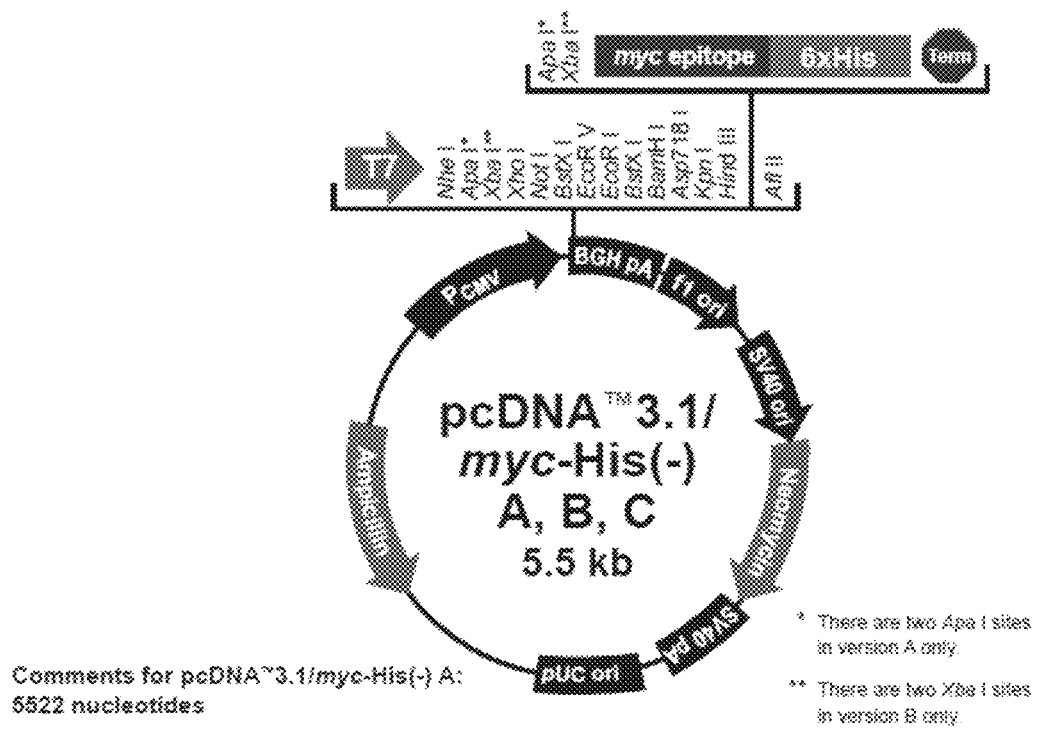
FIG. 10 is a Vector Map for pcDNA 3.1/myc-His (−) Versions A, B, C. This expression vector from Invitrogen Corp. features the CMV promoter for mammalian expression and Neomycin resistance for selection.

Expression vectors for each of the four minibody sequences above were generated. Each of the four minibody sequences was cloned into the pcDNA3.1/myc-His (−) Version A vector for mammalian expression (Invitrogen, Inc.) at the corresponding XbaI/HindIII sites. The pcDNA3.1 expression vector features a CMV promoter for mammalian expression and both mammalian (Neomycin) and bacterial (Ampicillin) selection markers (see FIG. 10).

The four J591 minibody expression vectors were transiently transfected into CHO-K1 cells to validate expression of the J591 minibodies. The transfections were performed using the Lipofectamine reagent in a 6-well plate format. Following a 72 hour transfection, the supernatants were harvested and filtered to remove any cells.

Figure 11:
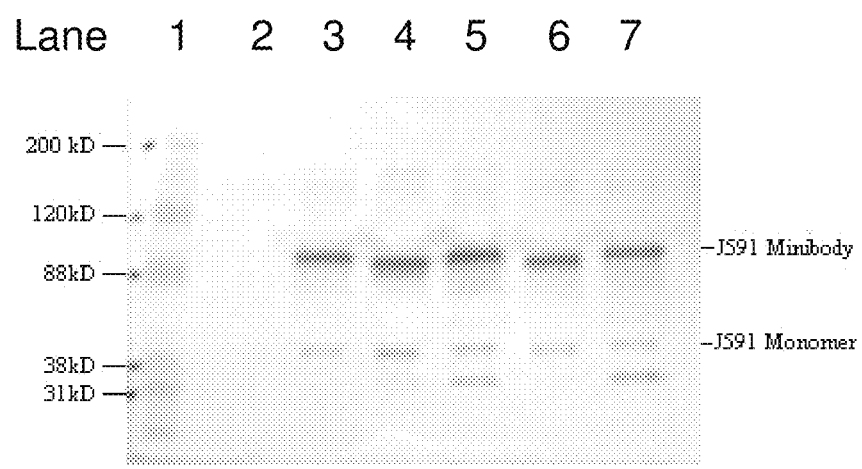
FIG. 11 is a representative Western blot analysis confirming the expression of the J591 minibodies by CHO-K1 cells. Lane 1 corresponds to a Molecular weight marker sample, Lane 2 corresponds to an Empty Vector sample, Lane 3 corresponds to a positive control minibody sample, Lane 4 corresponds to the J591 HO VLVH sample, Lane 5 corresponds to the J591 HC VHVL sample, Lane 6 corresponds to the J591 2P VLVH sample, and Lane 7 corresponds to the J591 2P VHVL sample.
Figures 12A, 12B:
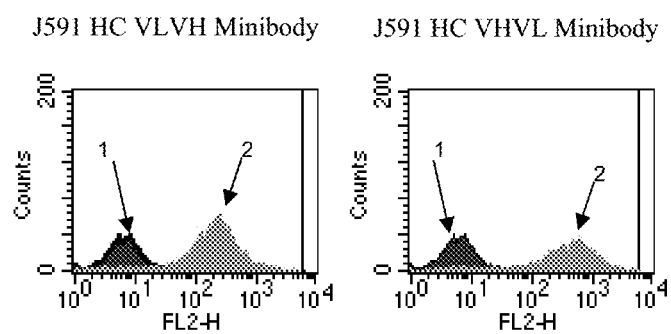
FIGS. 12A-D are graphs that represent flow cytometry analysis of the J591 minibodies. Histograms plot cell count versus PE signal (FL2-H).
Figures 12C, 12D:
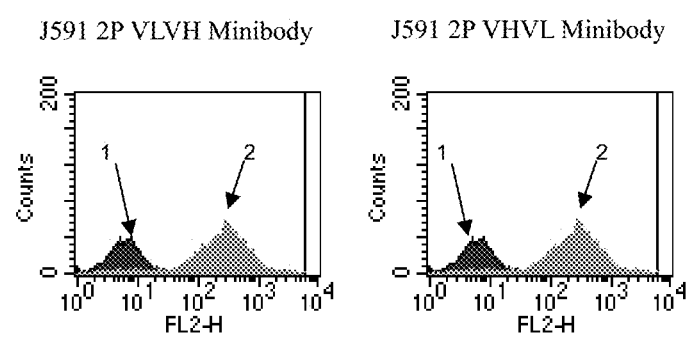

To confirm the expression of the J591 minibodies by the CHO-K1 cells, Western blot analyses were performed using sample of supernatant taken from the transient transfections. Supernatant from an empty vector transfection was included as a negative control, and supernatant from the transfection of a different minibody was used as a positive control. Transfection supernatants were run out by SDS-PAGE and transferred to PVDF membrane. The membrane was probed with an anti-human IgG (Fc-specific) antibody conjugated with Alkaline Phosphatase (AP) and developed by incubating with the AP substrate BCIP/NBT. FIG. 11 is a representative blot of multiple experiments that confirmed the expression of the J591 minibodies. Under non-reducing conditions, the J591 minibodies run at the expected molecular weight of approximately 90 kD (FIG. 11). A minor band representing the monomeric form was also detected at approximately 40 kD.

Quantitative ELISAs were performed to analyze J591 minibody expression from transient transfection. ELISA is a sandwich assay which uses a goat anti-human IgG (Fc specific) as the capture antibody and an AP-conjugated goat anti-human IgG (Fc specific) as the detection antibody. Purified protein for a previously produced minibody was used as a standard. J591 minibody supernatants were serially diluted to find dilution points which fit in the linear range of the standard curve. The program SoftMax Pro was used to interpolate the concentration of the unknowns according to the standard curve.

Figure 25:
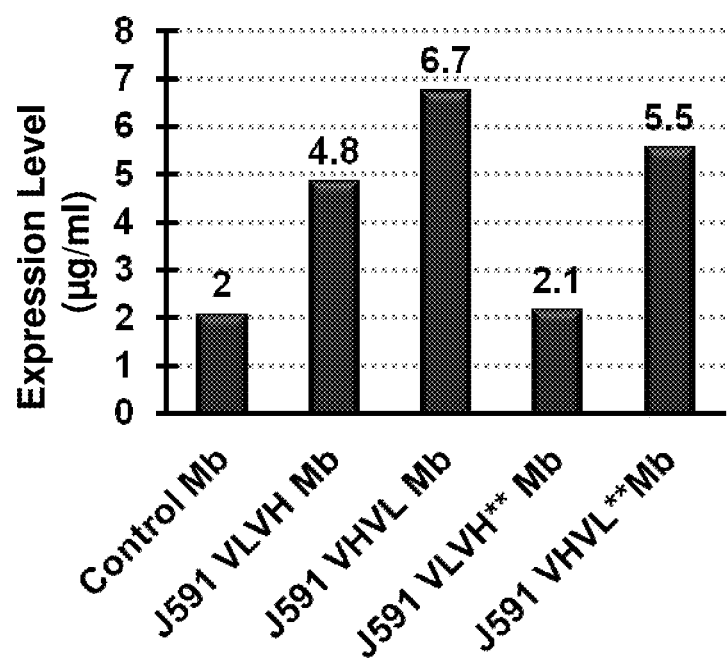
FIG. 25 is a bar graph illustrating the expression level of the following minibody variants in transient transfected CHO-K1 cells: (1) J591 HC VLVH minibody (J591 VLVH Mb), (2) J591 HC VHVL minibody (J591VHVL Mb), (3) J591 2P VLVH minibody (J591 VLVHMb) and (4) J591 2P VHVL minibody (J591 VHVLMb). The huJ591 HC VHVL exhibited the highest expression (6.7 .mu.g/mL) from transient transfection.

Supernatants from multiple transfections were assayed, and the averages are displayed in FIG. 25. The J591 HC VHVL minibody exhibited the highest expression (6.7 ug/ml) of the third generation minibodies.

Binding Ability of the J591 Minibodies.

To confirm the ability of the J591 minibodies to bind cellular PSMA, supernatant from the transient transfections described above were analyzed by flow cytometry. As illustrated in FIGS. 12A-12D, supernatants from the transient transfection for each of the J591 minibodies were tested for binding to LNCaP cells that are PSMA positive (PSMA+)(2) and compared to negative control cells that are PSMA negative. All supernatants were normalized to a concentration of 2.1 ug/ml of J591 minibody. Cells were subsequently stained with a secondary anti-human IgG (Fc specific)-PE conjugated antibody. Negative control cells were stained with the secondary alone (1). $1\times10^5$ cells/point and analysis was performed with 10,000 events/point.

Each of the cell populations stained with the J591 minibodies demonstrated a significant increase in signal relative to the negative control cells (see FIG. 12). The J591 minibody supernatants did not significantly stain negative control PC3 cells (PSMA negative) (data not shown). All four minibodies exhibited comparable binding affinity to the LNCaP cells (see FIG. 12).

Example 2: Stable Cell Line Production

Based on the expression and binding data described above, the J591 Human Composite VHVL (HC VHVL) minibody was selected as a lead candidate to move forward into larger scale (~low milligram quantity) protein production for subsequent in vivo imaging studies described below. Although the Examples described below are specific to the J591 HC VHVL minibody, however, it is noted that any of the J591 minibodies or cys-diabodies described herein may be purified and used in similar studies.

The J591 HC VHVL minibody was stably transfected into GHQ-K1 cells using Neomycin as the selection marker. Following selection for high-expressing clones, a clone expressing the J591 minibody at approximately 36 mg/L (over a 4 day culture) was chosen for scale-up production.

Protein Production Run.

To produce at least 10 mg of final purified protein, the stable cell line was expanded to a 400 ml production run (in 2% FBS media). Cells were seeded into eight T175 flasks, and the production run lasted for 7 days.

Protein Purification.

At the end of the production run, the supernatant was harvested, spun down to remove any cells, and filtered using 0.2 um filter units. The J591 minibody was purified from the supernatant using Protein L affinity chromatography. After loading, the column was washed with PBS (pH=7.2) and the minibody was eluted from the column using IgG Elution Buffer (Pierce, Thermo Scientific). Eluted fractions were immediately neutralized using 1M Tris buffer (pH=8). The final elution fractions were concentrated and buffer exchanged into the final formulation of PBS (pH=7.2).

Purified Protein Analysis.

After purification, the final concentration of J591 minibody protein was calculated using UV absorbance at 280 A. The absorbance coefficient was 1.76 (absorbance Units at A280 per mg/ml). The final concentration of the protein was 1.06 mg/ml.

Figure 13:
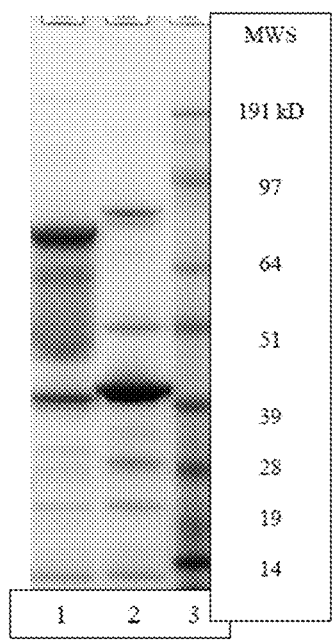
FIG. 13 is an SDS-PAGE analysis of the purified J591 minibody. The purified J591 minibody protein was loaded onto the SDS-PAGE gel under non-reducing conditions (lane 1) and reducing conditions (lane 2). The gel was stained with GelCode Blue (Pierce, Thermo Scientific). The minibody was diluted 1/5 for loading on the gel.

To analyze the purity of the J591 minibody, the protein was run under non-reducing and reducing conditions by SDS-PAGE. Under non-reducing conditions, the minibody was detected at approximately 85 kDa (FIG. 13). A relatively minor smear was present under the 85 kDa band which may represent a small amount of degradation. The minor band at approximately 40 kDa represents the minibody monomer. Under reducing conditions, the minibody was detected as the monomeric form at around 40 kDa (FIG. 13).

Figure 14:
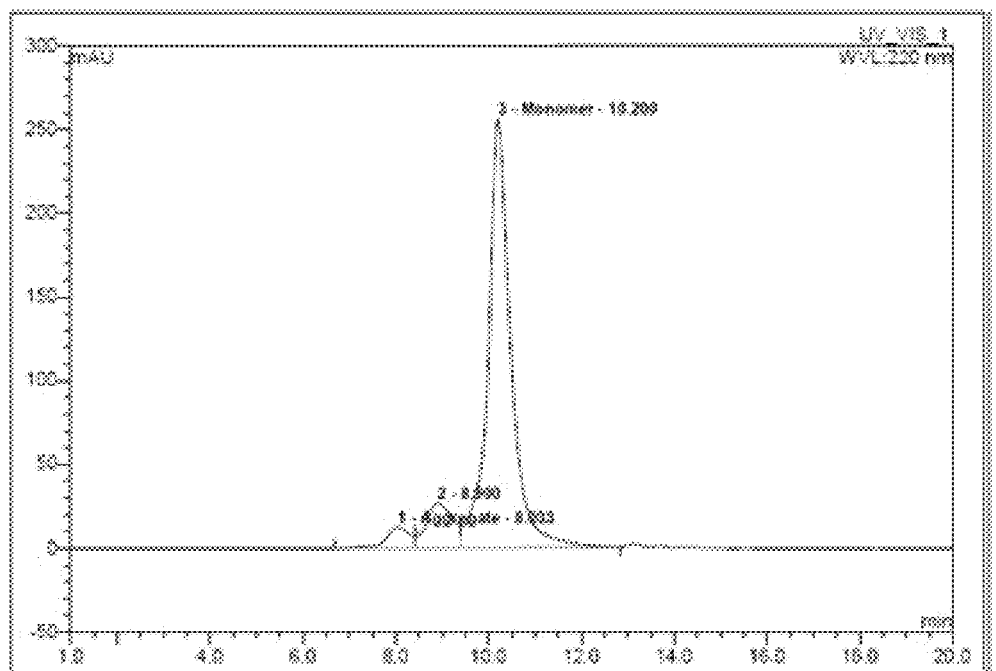
FIG. 14 is a size exclusion chromatography (SEC) analysis of purified J591 minibody. The graph plots the 220 nm UV absorbance (mAU) vs. time (min). 4 μg of the J591 minibody was loaded onto a TSK-GEL Super SW3000 column. A protein molecular weight standard was also run separately on the column to provide reference. The percentage of the aggregate versus the minibody protein (labeled here as monomer) was determined by calculating the area under the curve.

To examine the purity of the assembled minibody complex, the protein was analyzed by size exclusion chromatography. 4 micrograms of the purified protein was analyzed by SEC (FIG. 14). The major peak corresponds with minibody homodimer. The two minor peaks which eluted at earlier time points represent larger aggregate protein. Analysis of the area under the peaks showed that 85% of the protein product exists as the proper minibody homodimer vs 15% aggregate.

Example 3: J591 Minibodies Binds and is Internalized by PSMA+ Cells

High-expressing stable cell pools were generated with Catalent's proprietary GPEx technology using lentiviral transductions of serum-free CHO-S cells. Using ion exchange chromatography, the J591 minibody was purified from the cell supernatant with sufficiently high purity for downstream experiments. High purity of the product was confirmed by SDS-PAGE and SEC analysis (>85% purity). The purified protein does not have any significant bioburden (0 cfu/ml) and relatively low endotoxin levels (between 8 and 16 EU/mg). The total yield from this production run batch was 65 mg of J591 minibody protein.

Functional ELISA.

Figure 15:
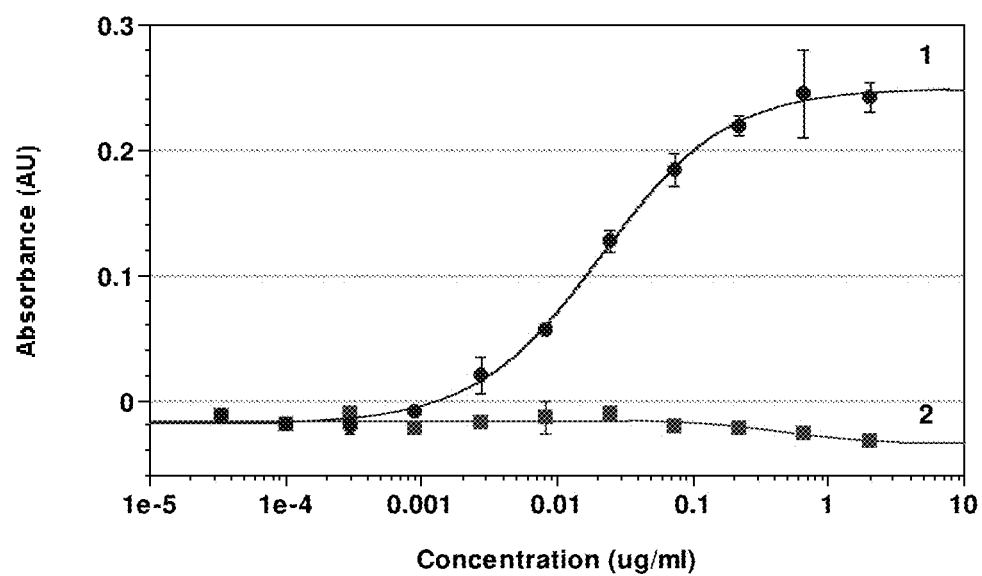
FIG. 15 illustrates that the J591 minibody protein binds PSMA by ELISA. 96-well ELISA plates were coated with purified recombinant PSMA protein at 1 μg/ml. Purified J591 minibody protein (1, •) was introduced at a starting concentration of 2 μg/ml and serially diluted ten times by third dilutions. Identical dilutions were performed for the negative control minibody (2, □). Samples were performed in triplicate at each dilution, and the error bars represent standard deviation. Following the primary incubation, bound minibodies were detected using a goat anti-human IgG (Fc specific) antibody conjugated to alkaline phosphatase and developed with a pNPP solution. Absorbance was detected at 405 nm.

To confirm the ability of the J591 minibody protein to bind purified PSMA, an indirect ELISA using purified recombinant PSMA was performed. A negative control minibody was included in the experiment. At the starting concentration of 2 µg/ml, the J591 minibody bound the recombinant PSMA at saturation (see FIG. 15). Subsequent serial dilutions of the J591 minibody showed concentration-dependent binding (see FIG. 15). As expected, the negative control minibody did not bind PSMA (see FIG. 15).

Flow Cytometry.

Figure 16A:
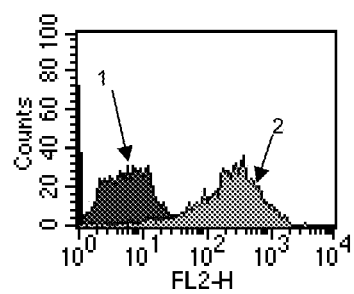
FIGS. 16A-D are graphs that represent flow cytometry analysis, illustrating that the J591 minibody binds PSMA+ cell lines. All histograms plot cell count vs. PE signal (FL2-H). The J591 minibody protein and the negative control minibody (1), both at 20 μg/ml, were tested for binding to the PSMA+ cell line LNCaP (A and B) and CWR22rv1 (C and D). Cells were subsequently stained with a secondary anti-human IgG (Fc specific)-PE conjugated antibody. $1 \times 10^5$ cells/point and analysis was performed with 5,000 events/point. (A) J591 minibody (2) binding LNCaP cells (B) J591-DOTA minibody (2) binding LNCaP cells (C) J591 minibody (2) binding CWR cells (D) J591-DOTA minibody (2) binding CWR cells.
Figure 16B:
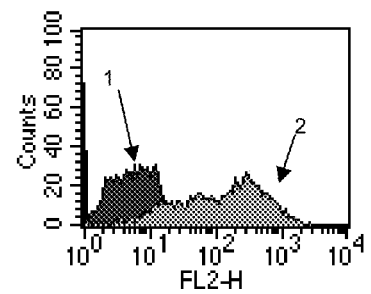
Figure 16C:
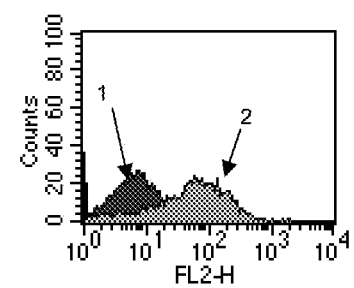
Figure 16D:
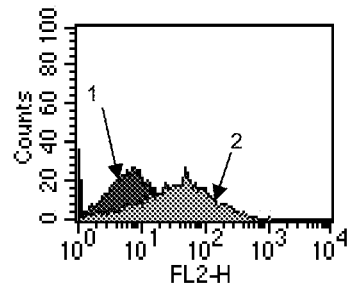

Following successful binding to recombinant PSMA in the ELISA, the J591 minibody protein was tested for the ability to bind PSMA+ cells by flow cytometry. Full-length hJ591 antibody was included in the experiment as a positive control (data not shown) and the negative control minibody was also included. The PSMA+ cells in this experiment were the LNCaP and CWR22rv1 cells and the PSMA-cell line was the PC3. The J591 minibody clearly binds both the LNCaP (see FIG. 16A) and the CWR22rv1 (see FIG. 16C) compared to an equivalent concentration of the negative control minibody. LNCaP cells are known to have a higher expression of PSMA than the CWRs which may explain the higher PE signal of the cell population (see FIG. 16, top row vs. bottom row). As anticipated, the J591 minibody did not significantly bind the P03 cells (data not shown).

Prior to this flow cytometry analysis, J591 minibody protein was conjugated with the bifunctional chelator 1,4,7,10-tetraazacyclododecane-N,N',N'',N'''-tetraacetic acid (DOTA) in preparation for downstream radiometal labeling. Conjugation was performed using the water-soluble N-hydroxysuccinimide method (Lewis et al 2001). Following DOTA conjugation, the protein conjugate was dialyzed to change buffer and remove excess DOTA.

To verify binding ability after conjugation, the J591-DOTA minibody was tested for binding to PSMA by flow cytometry. Compared to the unconjugated J591 minibody, the J591-DOTA minibody exhibited a slight decrease in immunoreactivity as shown in the slight shift in the PE signal of the cell population (see FIGS. 16B and 16D). Excessive conjugation of bifunctional chelators to antibodies has been known to be a cause for decrease in immunoreactivity (Kukis et al 1995). Conjugation conditions can be optimized to prevent excessive conjugation and the resulting loss of binding. However, the slight shift in binding for the J591-DOTA minibody was considered acceptable and the protein moved forward into radiolabeling.

Internalization of Unlabeled Minibody.

Internalization of the J591 minibody into PSMA+ cells was examined using immunofluorescence confocal microscopy. The two PSMA+ cell lines used in this experiment, the LNCaP and CWR22rv1 cell lines, have been previously used in cell-binding studies and also served in the subsequent radiolabeled internalization study. PC3 cells were used as the PSMA- negative control cell line. Full-length, parental J591 antibody was included in the experiment as a positive control. A negative control minibody was also included to further demonstrate the specificity of the J591 minibody uptake in PSMA+ cells.

Since previous internalization studies with the original full-length J591 antibody on LNCaP cells showed strong internalization by 180 minutes (Liu et al 1998), cells were stained at t=0 and t=0.180 minutes after primary antibody incubation to measure internalization. Localization of the antibody and minibody were detected by a secondary anti-human IgG antibody conjugated with the Alexa 488 fluorophore. Cells were counterstained with DAPI for staining of the nucleus.

Figure 17:
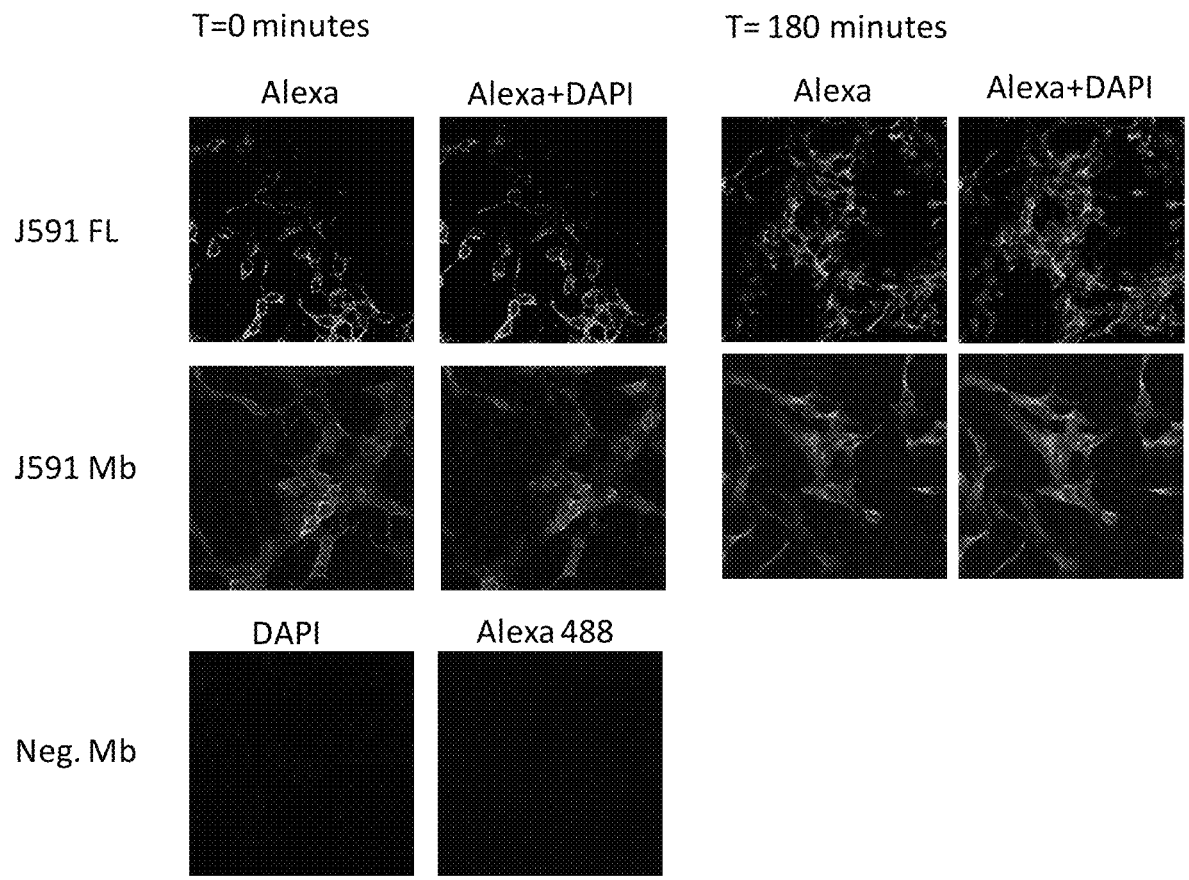
FIG. 17 are representative images that show the internalization of J591 minibody in LNCaP cells. LNCaP cells were plated on poly-d-lysine-coated coverslips in 12-well plates. Following 2 days of growth, the cells were pre-chilled for 30 minutes at 4C before incubation with the primary antibody or minibody for 30 minutes at 4C. At the indicated time points after primary incubation, the cells were fixed, permeabilized, and stained with secondary anti-human IgG-Alexa 488. The coverslips were simultaneously mounted on to slides and counterstained with DAPI within the mounting media. Slides were viewed using a 63× oil-immersion lens on a Leica SP2-1P-FCS confocal microscope.

The J591 full-length antibody showed very sharp and distinct staining of the plasma membrane at t=0 (see FIG. 17). After incubating 180 minutes at 37C, the J591 full-length antibody internalized into the LNCaP cells as shown by the dispersion of the of the Alexa 488 staining throughout the cell. The J591 minibody also showed distinct plasma membrane staining at t=0 and strong internalization by t=180 minutes (FIG. 17). Staining of the J591 minibody at t=0 was notably less distinct than the J591 full-length, perhaps suggesting a more rapid internalization for the smaller-sized minibody within LNCaP cells. The negative control minibody could not bind the LNCaP cells at t=0. The J591 full-length antibody and minibody could not bind the PSMA- PC3 cells (data not shown).

Figure 18:
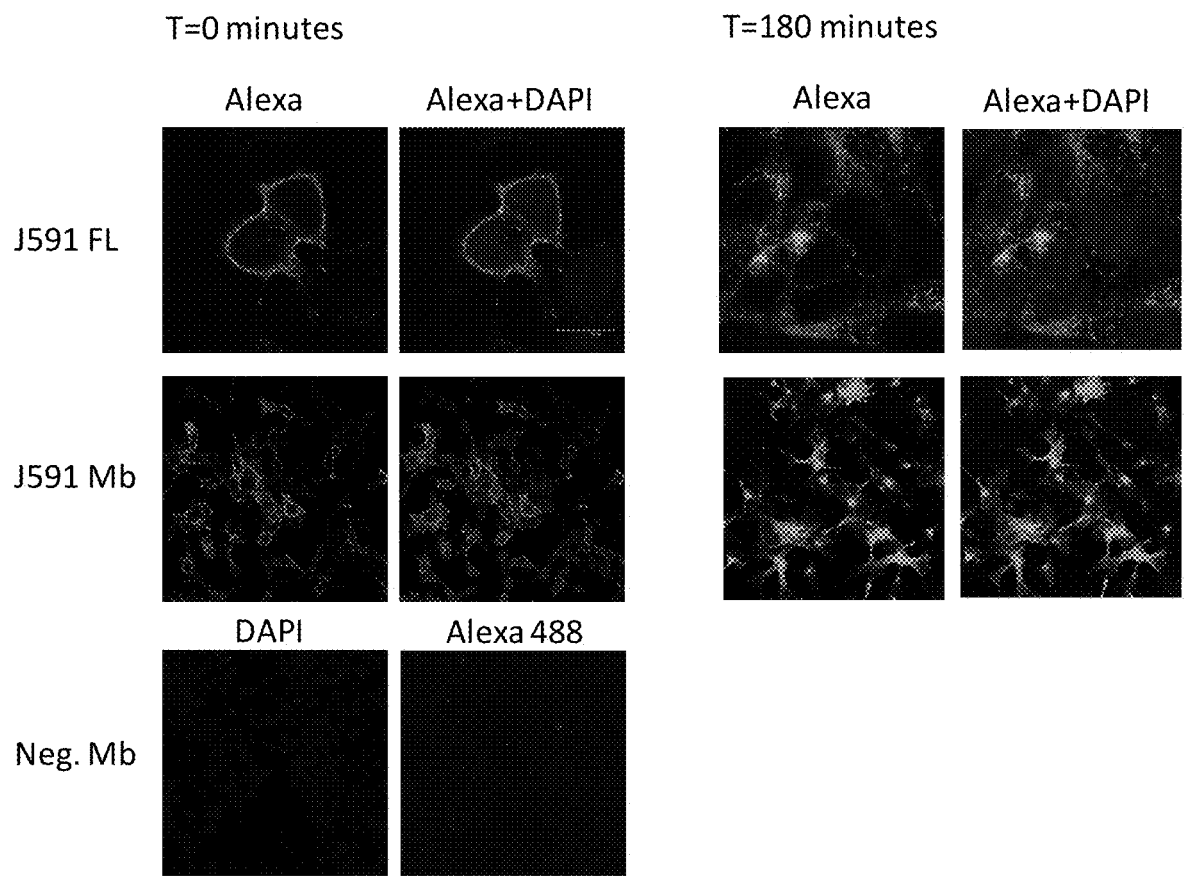
FIG. 18 are representative images that show the internalization of J591 minibody in CWR22rv1 cells. CWR22rv1 cells were plated on poly-d-lysine-coated coverslips in 12-well plates. Following 2 days of growth, the cells were pre-chilled for 30 minutes at 4C before incubation with the primary antibody or minibody for 30 minutes at 4C. At the indicated time points post-primary incubation, the cells were fixed, permeabilized, and stained with secondary anti-human IgG-Alexa 488. The coverslips were simultaneously mounted on to slides and counterstained with DAPI within the mounting media. Slides were viewed using a 63× oil-immersion lens on a Leica SP2-1P-FCS confocal microscope.

Internalization of the full-length J591 antibody into CWR22rv1 cells showed very similar staining pattern as seen for the LNCaP cells. Staining was very sharp and distinct on the plasma membrane at t=0 and became very dispersed by t=180 minutes (see FIG. 18). The J591 minibody was also internalized in the CWR22rv1 Staining at t=0 was distinctively plasma membrane and became much more dispersed by t=180 minutes (FIG. 18). As expected, the negative control minibody did not bind the CWR22rv1 cells (FIG. 18).

Example 4: Radiolabeled PSMA-Specific Minibodies

Radiolabeling J591 minibody with Iodine-131. Purified J591 minibody protein (50 µg) was radiolabeled with approximately 50 µCi of $^{131}$I using the Iodogen method from Pierce Thermo Scientific (as described in Olafsen et al 2006). This reagent enables the chemical oxidation reaction to attach $^{131}$I to available Tyrosine residues of the J591 minibody. Table 2 is a summary of the J591 minibody radiolabeling results, including radiolabeling efficiency, percentage of bound radioactivity after purification, and specific activity. The radiolabeling efficiency was determined to be approximately 51% using instant thin layer chromatography (ITLC) to measure the percentage of radioactivity bound to the protein versus unbound. (see Table 2 below). The specific activity was determined to be 0.46 µCi/µg by measuring the total activity of the radiolabeled protein using a dose calibrator and calculating the specific activity based on the labeling efficiency (Table 2). To remove excess unbound $^{131}$I, the radiolabeled protein was further purified using spin columns. The percentage of radioactivity bound to the J591 minibody following purification was dramatically increased to approximately 96% following purification (Table 2).

DOTA-Conjugating and Radiometal Labeling the J591 with Indium-111.

J591 minibody, previously conjugated with the bifunctional metal chelator DOTA, was radiolabeled with $^{111}$In. 100 µg of the DOTA-J591 minibody was incubated with 200 µCi $^{111}$In-chloride in 0.1 M metal-free ammonium acetate (pH 6.0) at 43C for 50 minutes. The reaction was stopped by the addition of 10 mM DTPA to a final concentration of 1 mM. Radiolabeling efficiency was determined to be approximately 60% and the specific activity was 1.1 µCi/µg (see Table 2). The radiolabeled protein was further purified to remove excess unbound $^{111}$In using spin columns. Similar to the $^{131}$I-J591 minibody, the percentage of radioactivity bound to the J591 minibody following purification was dramatically increased to approximately 94% (Table 2).

TABLE 2

Radiolabeling of the J591 Minibody with $^{131}$I and $^{111}$In.

| | Radiolabeling Efficiency (%) | % Bound Radioactivity Post-Purification | Specific Activity (uCi/ug) |
|---|---|---|---|
| $^{131}$I | 51% | 96.2% | 0.46 |
| $^{111}$In-DOTA | 60% | 94.2% | 1.1 |

Internalization and Retention of Radiolabeled J591 Minibody.

The $^{131}$I-labeled and $^{111}$In-DOTA labeled J591 minibody were tested for uptake and retention of cell-associated radioactivity in the PSMA+ CWR22rv1 cells. The CWR22rv1 cells were selected as the sole PSMA+ cell line for these in vitro experiments since they will be used for the microPET imaging experiment. Drawing from the literature and the experimental knowledge of colleagues, the CWR22rv1 xenograft model has a higher tumor take rate and faster in vitro and tumor growth rates than the LNCaP model.

Figure 19A:
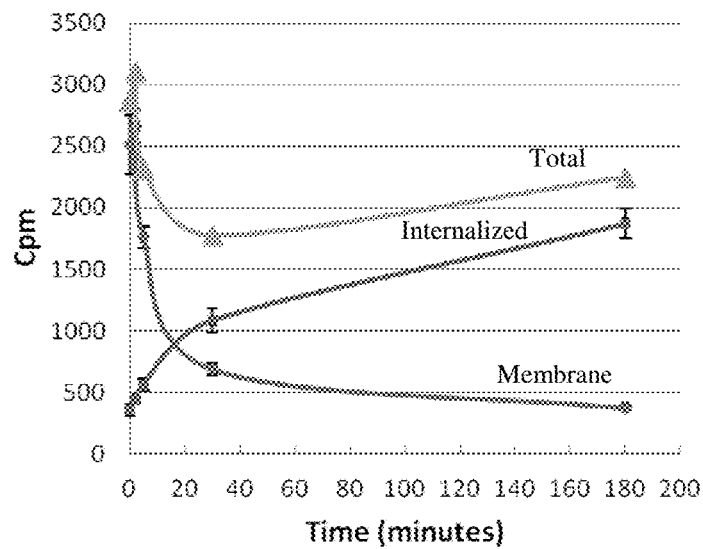
FIGS. 19A-19B are graphs illustrating uptake and retention of cell-associated radioactivity of $^{131}$I-labelled and $^{111}$In-DOTA labelled J591 minibody. The uptake and retention of cell-associated radioactivity over time upon binding to CWR22rv1 cells. The radioactivity from the cell membrane, cell lysate (internalized), and total (membrane+internalized) fractions are expressed as counts per minute (cpm). CWR22rv1 cells were seeded into 24-well plates at $5 \times 10^5$ cells/well the day before the experiment. Cells were pre-chilled at 4C before incubation with an excess of (A) $^{131}$I-labelled or (B) $^{111}$In-DOTA labelled J591 minibody. At each time point, the supernatant containing the radiolabeled minibody was removed, the cells were stripped with an acidic glycine buffer to obtain the membrane fraction, and the cells were lysed. Each time point was performed in triplicate. The Y-bars represent standard deviation.

For the uptake and retention of the $^{131}$I-labeled J591 minibody, the amount of radioactivity associated with the membrane rapidly drops within the first 30 minutes whereas the internalized radioactivity rapidly increases in this timeframe (see FIG. 19A). Together these data suggests the internalization of the $^{131}$I-J591 minibody. Although the amount of internalized $^{131}$I J591 increases over time, the total cell-associated radioactivity decreased substantially by 180 minutes relative to the initial starting point of ~2900 cpm (see FIG. 19A).

Figure 19B:
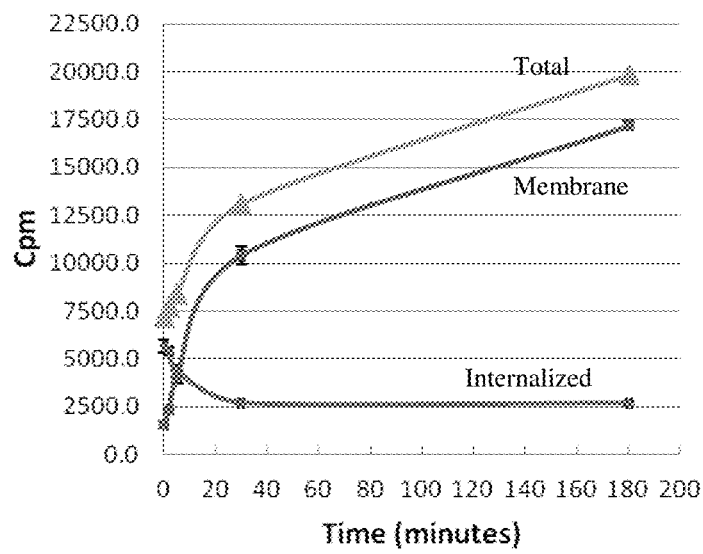

In sharp contrast, the uptake and retention of the $^{111}$In-DOTA labelled J591 minibody showed a relatively large increase in total cell-associated radioactivity over time (see FIG. 19B). Similar to the $^{131}$I labelled J591 minibody, the membrane-associated radioactivity dramatically decreases as the internalized radioactivity increases suggesting active internalization (see FIG. 19B). Attributed in large part to the increase in internalized radioactivity over time, the total cell-associated radioactivity increased to approximately 20,000 cpm by 180 minutes from a starting point of ~7,500 cpm (FIG. 19B).

Figure 20:
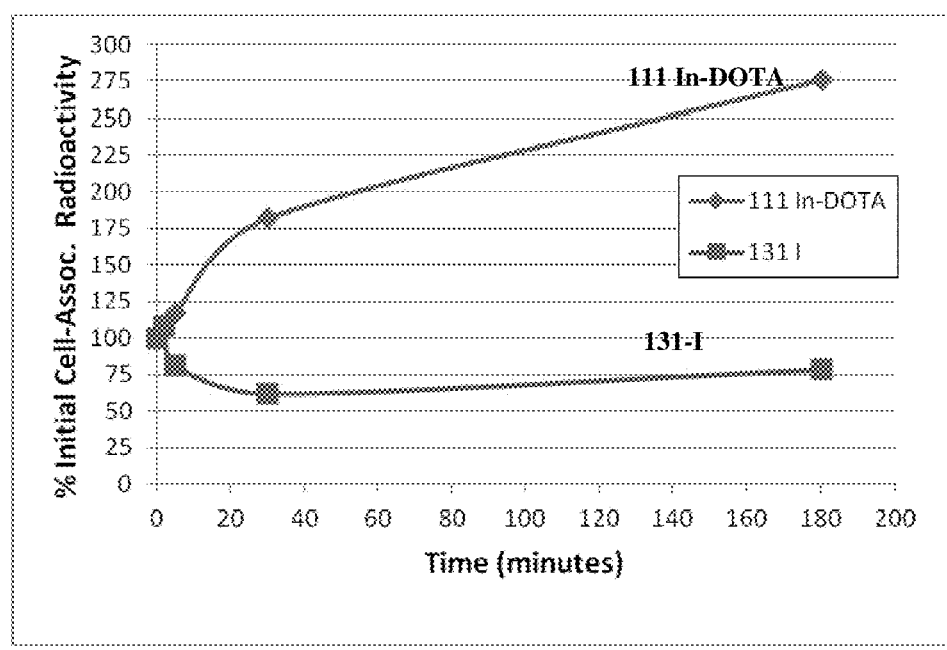
FIG. 20 is a graph comparing cell-associated radioactivity of $^{131}$I labelled versus $^{111}$In-DOTA labelled J591 minibody. The total cell-associated radioactivity (membrane+internalized) expressed as a percentage of the initial cell-associated radioactivity over time upon binding to CWR22rv1 cells. This plot shows both the $^{131}$I-labelled (bottom line) and the $^{111}$In-DOTA labelled J591 minibody (top line).

To compare the two radiolabeled J591 minibodies, the total cell-associated radioactivity was normalized by expressing the data in terms of percentage of the initial cell-associated radioactivity for each respective radiolabel at t=0 (see FIG. 20). By t=180 minutes, the $^{111}$In-DOTA labeled J591 minibody increases to ~250% of the initial cell-associated radioactivity whereas the $^{131}$I labeled J591 minibody decreases to ~80% of the initial (FIG. 20). As seen by other groups in the literature (Vaidyanathan et al 2009), a non-residualizing $^{131}$I labeling strategy resulted in an overall decrease in cell-associated radioactivity over time. These data clearly shows the retention and accumulation of cell-associated radioactivity over time for the residualizing $^{111}$In-DOTA radiolabel.

Purified J591 HC VHVL minibody (or any of the minibodies described above) may be used to demonstrate the ability to target human PSMA in vivo in microPET imaging and biodistribution studies. In one embodiment, the purified J591 HC VHVL minibody protein may first be validated again to confirm its ability to bind PSMA in vitro in preparation for the imaging studies. Upon confirmation of binding, the J591 HC VHVL minibody may then be conjugated to the bifunctional chelator DOTA and radiolabeled with an appropriate positron-emitting radiometal for micro-PET such as Copper 64. Radiolabeled minibody can be analyzed to ensure high radiolabeling efficiency and immunoreactivity before proceeding to micoPET imaging.

In some embodiments, the radiolabeled minibody can be injected intravenously into xenograft mice implanted with either PSMA positive or PSMA negative tumors. At specific time points post-injection, each animal may be serially scanned by PET. After the final scan, animals may be scanned by CT for anatomical reference. The PET and CT images for each animal may then be analyzed to evaluate tumor targeting and specificity.

Example 5: In Vivo Binding and Biodistribution of $^{124}$I-J591 and $^{64}$Cu-DOTA-Conjugated J591 Minibodies Radiolabeling J591 Minibody with Iodine-124.

Purified J591 minibody protein (total amount of 300 µg) was radiolabeled with approximately 1.3 mCi of $^{124}$I using the Iodogen method from Pierce Thermo Scientific (as described in Olafsen et al 2006). This method involves a chemical oxidation reaction to attach $^{124}$I radioisotope to available Tyrosine residues of the J591 minibody. Table 3, below, is a summary of the J591 minibody radiolabeling results including radiolabeling efficiency, percentage of bound radioactivity after purification, specific activity, and immunoreactivity. Following the labeling reaction, the radiolabeling efficiency was determined to be approximately 62% (percentage of radioactivity bound to the protein versus unbound) using instant thin layer chromatography (ITLC) (see Table 3). Radiolabeled J591 minibody was partially purified using Sephadex G-25 spin columns and re-evaluated by ITLC to determine the percentage of bound radioactivity. The specific activity of the radiolabelled protein was 2.6 µCi/µg (Table 3), as determined by measuring the total radioactivity of the protein using a dose calibrator. To remove excess unbound $^{124}$I from the reaction, the radiolabeled protein was further purified using spin columns. The percentage of radioactivity bound to the J591 minibody following purification was dramatically increased to approximately 98% (Table 3). Immunoreactivity of the $^{124}$I-J591 minibody was determined to be 48% by testing binding to CWR22rv1 vs PC3 cells (Table 3). Although this immunoreactivity was lower than anticipated, the decision was made to move the $^{124}$I J591 minibody forward into the imaging and biodistribution experiment based on the previous binding performance of the minibody. Future optimizations to the radiolabeling conditions (pH, time, temperature, etc) and obtaining higher protein purity could potentially improve the immunoreactivity.

TABLE 3

Radiolabeling of the J591 Minibody with $^{124}$I and $^{64}$Cu.

| Labelling Conditions | | Radiolabeling Efficiency (%) | % Bound Radioactivity Post-Purification | Specific Activity (uCi/ug) | Immunoreactivity (%) |
|---|---|---|---|---|---|
| $^{124}$I | Protein in PBS | 62% | 98.0% | 2.6 | 48% |
| $^{64}$Cu-DOTA | Protein in PBS | 40% | 85% * | 1 * | 29% * |
| $^{64}$Cu-DOTA | AmmOAc, increase AmmCitr buffer | 92% | 85% * | 1 * | 29% * |

* Fractions from both labelling conditions were combined

Radiometal Labeling the DOTA-J591 Minibody with Copper-64.

J591 minibody, previously conjugated with the bifunctional metal chelator DOTA, was radiolabeled with $^{64}$Cu. For the initial radiolabeling condition, 400 µg of the DOTA-J591 minibody in PBS was incubated with approximately 745 µCi $^{64}$CuCl$_2$ in 25 mM metal-free ammonium citrate [pH 5.2] at 43C for 60 minutes. The reaction was stopped by the addition of 10 mM EDTA to a final concentration of 1 mM. Using these labeling conditions, radiolabeling efficiency was determined to be lower than anticipated at approximately 40% (see Table 3).

In an attempt to improve labeling efficiency, the DOTA-J591 minibody was first dialyzed into 0.25 ammonium acetate buffer [pH 7.2] before starting the radiolabeling reaction. An additional 560 µg of the DOTA-J591 minibody, in the ammonium acetate buffer, was labeled with approximately 730 uCi of $^{64}$CuCl$_2$. Another adjustment to improve the radiolabeling involved increasing the percentage of ammonium citrate buffer used in the reaction. With these adjustments, the radiolabeling efficiency was dramatically increased to approximately 92% (Table 3).

All of the $^{64}$Cu-DOTA J591 minibody fractions from both labeling conditions were pooled together and further purified to remove excess unbound $^{64}$Cu using spin columns. The percentage of radioactivity attached to the J591 minibody following purification was approximately 85%, and the specific activity was 1 µCi/µg (Table 3). Immunoreactivity of the radiolabeled minibody was determined to be approximately 29% (Table 3) using the cell-based method described previously for $^{124}$I J591 minibody. Although the immunoreactivity was lower than expected, the decision was made to move forward into the microPET and biodistribution experiment. In addition to the protein purity and the labeling conditions, future efforts to optimize immunoreactivity could include optimizing the DOTA conjugation reaction (i.e. DOTA-molecule ratio, etc).

Example 6: Serial microPET Imaging and Biodistribution of Radiolabeled J591 Minibodies $^{64}$Cu-Data J591 Minibody.

Figure 21A:
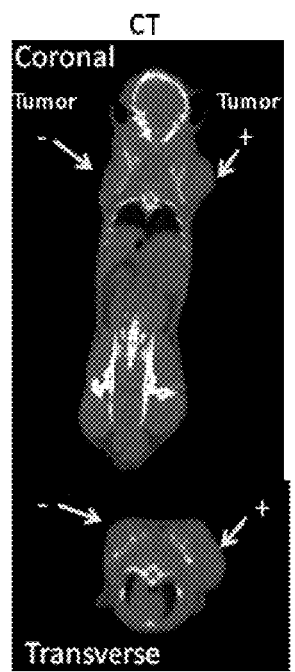
FIGS. 21A-21D illustrate representative serial microPET/CT images of a mouse bearing CWR22rv1 and PC3 xenografts injected with $^{64}$Cu-DOTA-J591 minibody. A representative mouse was serially scanned at multiple times postinjection. The CWR22rv1 tumor is depicted as the (+) tumor and the PC3 tumor as the (−) tumor. (A) CT scan at 4 hours postinjection. Coronal and transverse planes are shown. (B) PET/CT overlay image at 4 hours postinjection. Coronal and transverse planes are shown. (C) Coronal PET/CT overlay 3D projection of the representative mouse at 4 hours postinjection (D) Coronal PET/CT overlay 3D projection of the representative mouse at 43 hours postinjection.
Figure 21B:
Figure 21C:
Figure 21D:
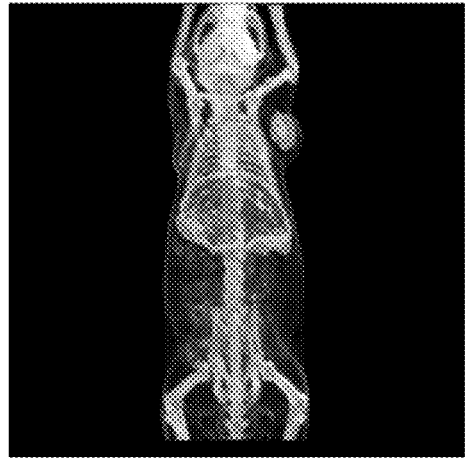

To evaluate the tumor targeting and binding specificity of the $^{64}$Cu-DOTA-J591 minibody, microPET imaging and biodistribution analysis was performed using mice implanted with both CWR22rv1 (PSMA+) and PC3 (PSMA−) xenografts. Both xenograft tumors were grown to a size between 39-223 mg before starting the imaging experiment. The CT and PET/CT images, at 4 hours post-injection, showed rapid tumor localization at the CWR22rv1 tumor compared to the PC3 tumor (FIGS. 21A and 21B show a representative mouse). As expected for a radiometal labeled minibody, prominent activity was detected in thorax and particularly localized to the liver. Localization of the radiometals such as $^{64}$Cu has been well-studied in the literature (Yazaki et al 2001). With the exception of the liver, background activity was relatively low even at 4 hours post-injection allowing for PET/CT images with remarkable contrast (FIGS. 21B and 21C). Strong tumor localization persisted at 19 hours and even 43 hours post-injection (FIG. 21D). The overall background activity decreased slightly over time but the liver remained a strong source of activity (FIG. 21D).

Figure 22:
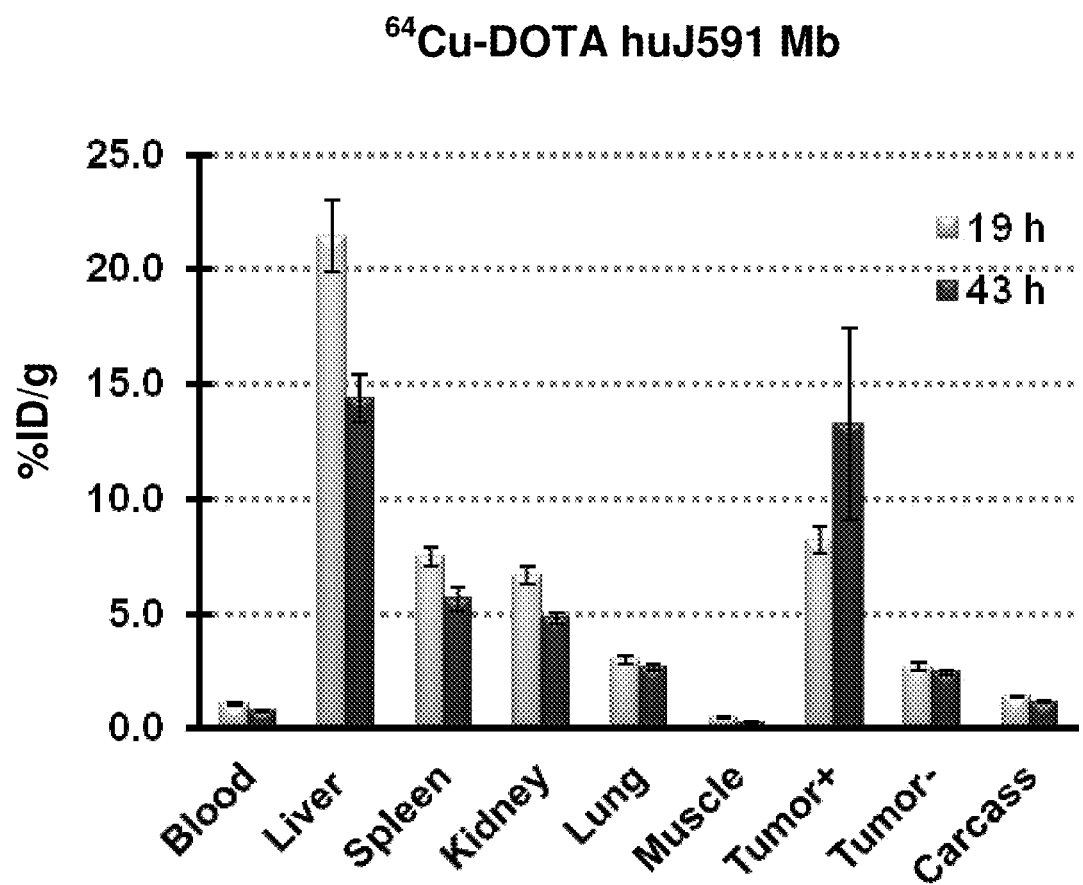
FIG. 22 is a bar graph illustrating the biodistribution of $^{64}$Cu-DOTA-J591 minibody at 19 hours and 43 hours post-injection. Graph plotting the biodistribution of the $^{64}$Cu-DOTA-J591 minibody in the xenograft tumors and selected normal tissues of interest. Biodistribution is plotted as % of the injected dose divided by weight in grams (% ID/g). Each data point represents the average % ID/g for the group of mice at 19 hrs (n=8) and 43 hrs postinjection (n=4). The error bars represent the standard deviation.

Following the final scan, all animals (n=8 at 19 hours and n=4 at 43 hours p.i.) were euthanized and selected tissues of interest (including the positive and negative tumors, blood, liver, spleen, lungs, and kidneys) were excised, weighed, and measured by a gamma counter for radioactivity. The biodistribution at 19 hours post-injection in FIG. 22 showed that CWR22rv1 tumor (Tumor+) reached an average uptake of 8.23% ID/g compared to 2.69% ID/g for the PC3 tumor (Tumor−). Localization was significantly higher at the CWR22rv1 than PC3 tumor (p<0.05). As revealed by the microPET/CT imaging, uptake in the liver at 19 hours p.i. was relatively high (21.43% ID/g) whereas the localization was much less prominent in the other tissues of interest (see FIG. 22).

At 43 hours postinjection, the biodistribution reveals an increase in the average uptake at the CWR22rv1 tumor (Tumor+; 13.25% ID/g) compared to 19 hours postinjection (FIG. 22). Background activity decreased relative to 19 hours post-injection, particularly the significant decrease in liver activity to 14.37% ID/g (FIG. 22).

Figure 26:
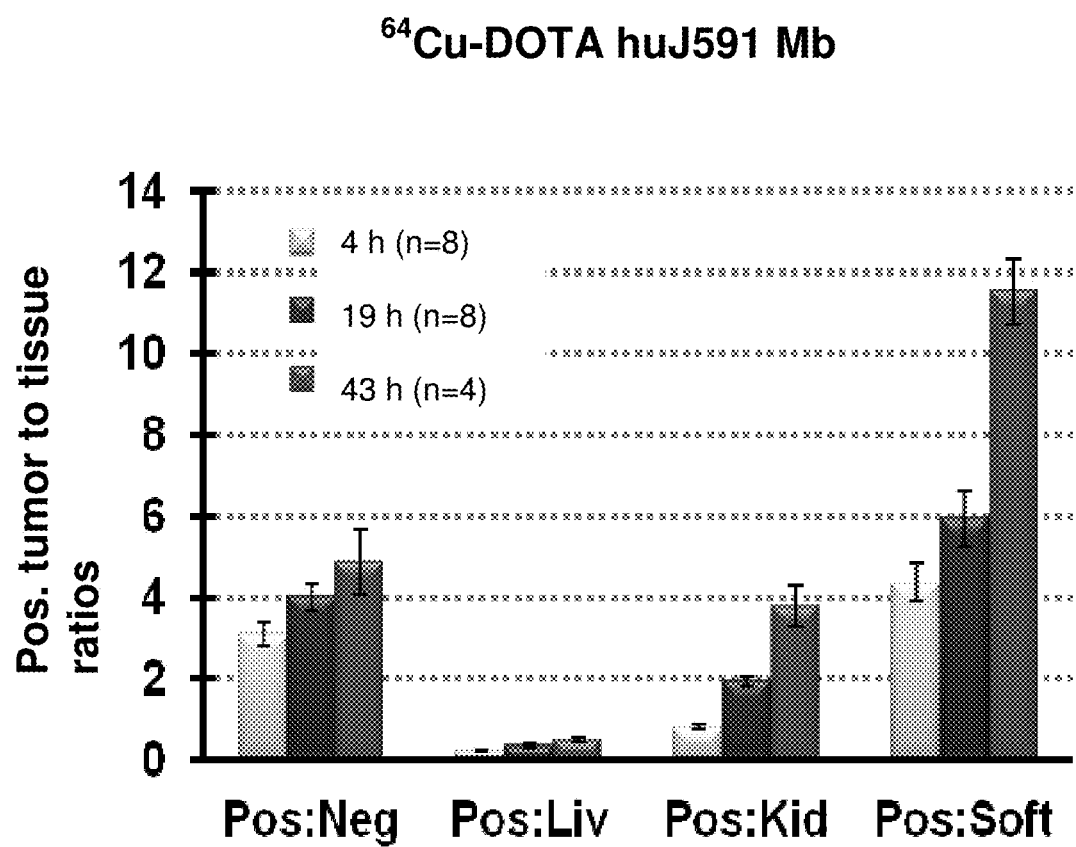
FIG. 26 is a bar graph showing the biodistribution ratios (i.e., positive tumor to tissue ratios) at 4 hours, 20 hours and 43 hours after injection of the $^{64}$Cu-DOTA-J591 minibody. The biodistribution ratios included ratios of positive tumor (Pos) compared to liver (Liv), kidneys (Kid) and soft tissue (Soft). Error bars represent mean standard errors (SEM).

With the overall decrease in background activity combined with the increasing accumulation at the CWR22rv1 tumor, the tumor to background ratios increased dramatically between 19 hours postinjection to 43 hours postinjection (FIG. 26).

$^{124}$I J591 Minibody.

As with the $^{64}$Cu-DOTA J591 minibody, microPET and biodistribution experiments were performed with the $^{124}$I J591 minibody to evaluate tumor targeting. Both xenograft tumors were grown to a range in size between 36-192 mg before starting the imaging experiment. MicroPET images at 4 hours postinjection (p.i.) showed rapid localization at the CWR22rv1 tumor but high circulating activity in the thorax, abdomen, and bladder (FIGS. 23A and 23B). Background activity cleared significantly from the system by 20 hours postinjection and was almost completely absent by 44 hours while the activity at the positive tumor remained (FIG. 23C).

Figure 24:
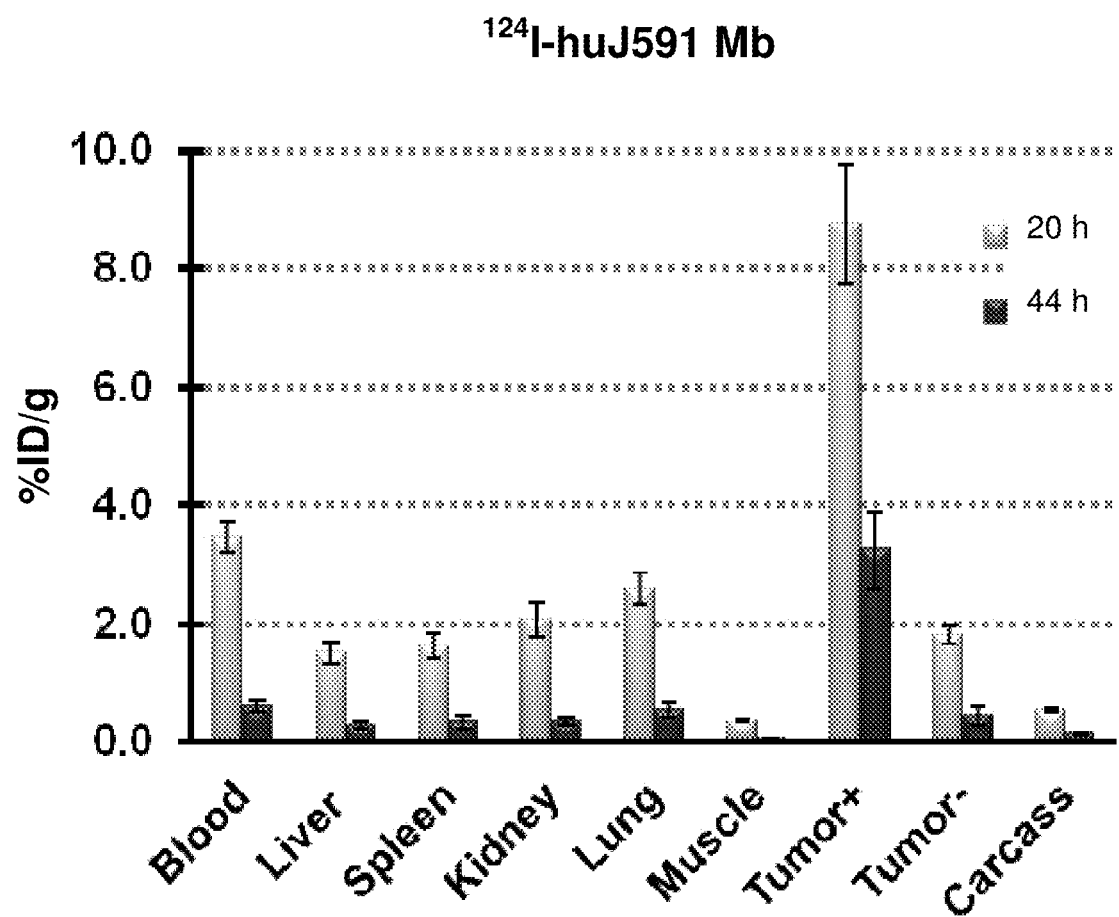
FIG. 24 is a bar graph illustrating the biodistribution of $^{124}$I-J591 minibody at 19 hours and 44 hours post-injection. Graph plotting the biodistribution of the $^{124}$I-J591 minibody in the xenograft tumors and selected normal tissues of interest. Biodistribution is expressed as % of the injected dose divided by weight in grams (% ID/g). Each data point represents the average % ID/g for the group of mice (n=4 at 19 hours, n=2 at 44 hours) at 19 hrs and 44 hrs postinjection. The error bars represent the standard deviation.

For biodistribution analysis, all animals in a group were euthanized after the final scan (n=6 at 20 hours and n=2 at 44 hours p.i.) and the selected tissues of interest were excised, weighed, and measured by a gamma counter for radioactivity. The biodistribution at 20 hours post-injection for the mouse in FIG. 24 showed that CWR22rv1 tumor (Tumor+) uptake reached 8.75% ID/g compared to 1.8% ID/g for the PC3 tumor (Tumor−). Localization was significantly higher at the CWR22rv1 than PC3 tumor (p<0.05). Background activity was relatively low by 20 hours p.i. (FIG. 24).

By 44 hours post-injection, the CWR22rv1 tumor (Tumor+) uptake decreased substantially to 3.25% ID/g (FIG. 24). Supporting the previous results from the in vitro internalization and retention experiments described above, cell-associated radioactivity decreased over time from dehalogenation and/or metabolism of the $^{124}$I-J591 minibody. Background activity was almost entirely cleared from the system by 44 hours p.i. (FIG. 24).

Figure 27:
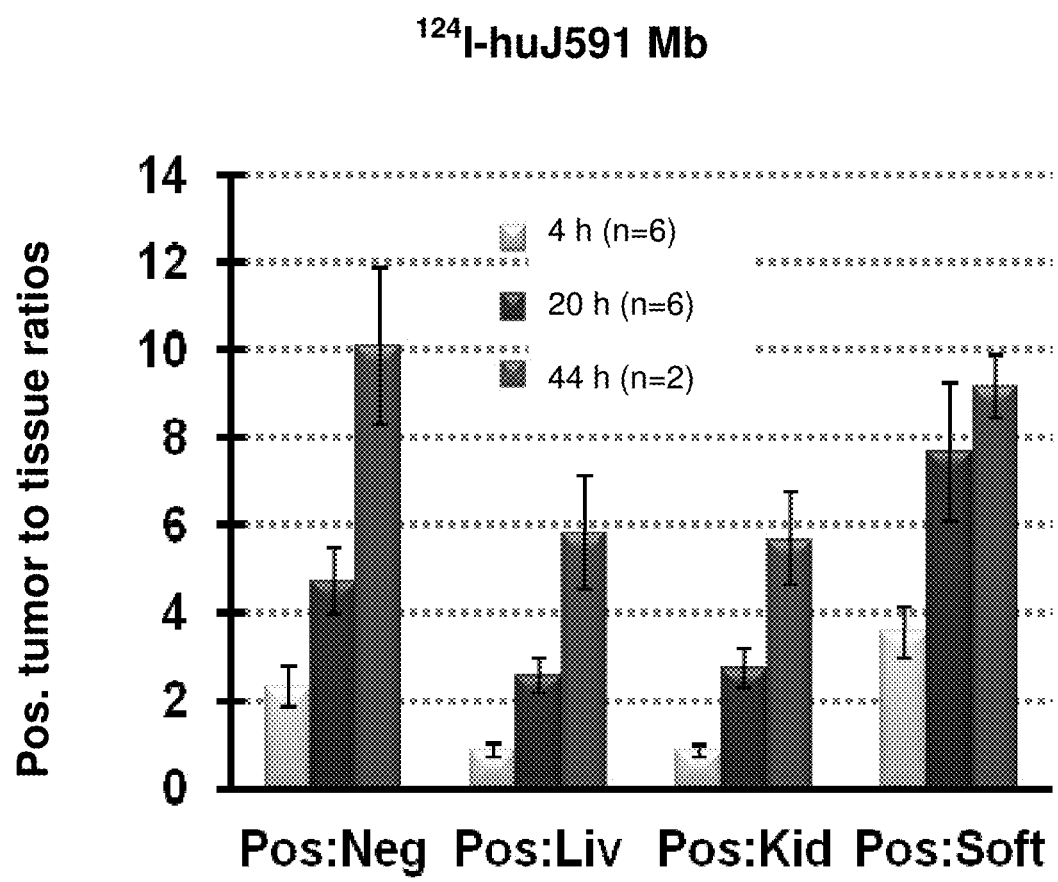
FIG. 27 is a bar graph showing the biodistribution ratios (i.e., positive tumor to tissue ratios) at 4 hours, 20 hours and 43 hours after injection of the $^{124}$I-J591 minibody. The biodistribution ratios included ratios of positive tumor (Pos) compared to liver (Liv), kidneys (Kid) and soft tissue (Soft). Error bars represent mean standard errors (SEM).

Although the uptake of activity decreased at the CWR22rv1 tumor over time (FIG. 24), the rapid decrease in background activity allowed a strong contrast for the images. The biodistribution ratios reflect this large increase in tumor to background over time (FIG. 27).

Upon successful imaging of PSMA positive tumors by the J591 minibody, the biodistribution of the minibody may be investigated according to embodiments of the disclosure. These biodistribution studies can investigate the localization of the minibody at the tumor site versus other selected tissues over time following injection. These studies may be used to demonstrate high tumor to background ratios. Use of a J591 minibody would likely produce a high tumor to background ratio when imaging a tumor that overexpresses PSMA, such as in prostate cancer. Positive results from these imaging and biodistribution experiments may lead to toxicology experiments in preparation for clinical studies.

Further, the ability of a J591 minibody to target human PSMA in vivo by PET imaging studies may be demonstrated through clinical trials in cancer patients. In one embodiment, the clinical trials may be performed in prostate cancer patients. These clinical trials in cancer patients may be performed using similar methods as described above. Briefly, radiolabeled minibody can be injected intravenously into cancer patients having a form of cancer that is known to overexpress PSMA. At specific time points post-injection, each patient may be serially scanned by PET. After the final scan, patients may be scanned by CT for anatomical reference. The PET and CT images for each patient may then be analyzed to evaluate tumor targeting and specificity.

REFERENCES

The references, patents and published patent applications listed below, and all references cited in the specification above are hereby incorporated by reference in their entirety, as if fully set forth herein.

Bander N H, Trabulsi E J, Kostakoglu L, Yao D, Vallabhajosula S, Smith-Jones P, Joyce M A, Milowsky M, Nanus D M, Goldsmith S J. Targeting metastatic prostate cancer with radiolabeled monoclonal antibody J591 to the extracellular domain of prostate specific membrane antigen. J Urol, 2003. 170 (5): 1717-1721.

Bander N H, Milowsky M I, Nanus D M, Kostakoglu L, Vallabhajosula S, Goldsmith S J. Phase I trial of 177 Lutetium-labeled J591, a monoclonal antibody to prostate-specific membrane antigen, in patients with androgen-independent prostate cancer. J Clin Oncol, 2005. 23(21): 4591-601.

Hu S, Shively L, Wu A M. Minibody: A novel engineered anti-carcinoembryonic antigen antibody fragment (single-chain Fv-CH3) which exhibits rapid, high-level targeting of xenografts. Cancer Res, 1996. 56(13):3055-61.

Kukis D L, Denardo G L, Denardo S J, Mirick G R, Miers L A, Greiner D P, Meares C F. Effect of the Extent of Chelate Substitution on the Immunoreactivity and Biodistribution of 2IT-BAT-Lym-1 Immunoconjugates, 1995. 55, 878-884.

Lewis M R, Kao J Y, Anderson A L, Shively J E, Raubitscheck A. An improved method for conjugating monoclonal antibodies with N-hydroxysulfosuccinimidyl DOTA. Bioconjug Chem, 2001. 12: 320-324.

Leyton J V, Wu A M. Humanized radioiodinated minibody for imaging of prostate stem cell antigen-expressing tumors. Clin Cancer Res, 2008. 14(22):7488-96.

Liu H, Rajasekaran A K, Moy P, Xia Y, Kim S, Navarro V, Rahmati R, Bander N H. Constitutive and Antibody-induced Internalization of Prostate-specific Membrane Antigen. Cancer Res, 1998. 58: 4055-4060.

Liu H, Moy P, Kim S, Xia Y, Rajasekaran A, Navarro V, Knudsen B, Bander N H. Monoclonal antibodies to the extracellular domain of prostate specific membrane antigen also react with tumor vasculature endothelium. Cancer Res, 1997. 57(17): 3629-34.

Milowsky M I, Nanus D M, Kostakoglu L, Vallabhajosula S, Goldsmith S J, Bander N H. Phase I trial of Yttrium-90-labeled anti-prostate specific membrane antigen monoclonal antibody J591 for androgen-independent prostate cancer. J Clin Oncol, 2004. 22(13): 2522-2531.

Milowsky M I, Nanus D M, Kostakoglu L, Sheehan C E, Vallabhajosula S, Goldsmith S J, Ross J S, Bander N H. Vascular targeted therapy with anti-prostate-specific membrane antigen monoclonal antibody J591 in advanced solid tumors. J Clin Oncol, 2007. 25(5): 540-547.

Morris M J, Divgi C R, Pandit-Taskar N, et al. Pilot trial of unlabeled and indium-111-labeled anti-prostate-specific membrane antigen antibody J591 for castrate metastatic prostate cancer. Clin Cancer Res, 2005. 11 (20): 7454-7461.

Olafsen T, Tan G J, Cheung C W, Yazaki P J, Park J M, Shively J E, Williams L E, Raubitschek A A, Press M F, Wu A M. Characterization of engineered anti-p185HER-2 (scFv-CH3)2 antibody fragments (minibodies) for tumor targeting. Protein Eng Des Sel, 2004. 17(4):315-23.

Olafsen T, Kenanova V E, Wu A M. Tunable pharmacokinetics: modifying the in vivo half-life of antibodies by directed mutagenesis of the Fc fragment. Nat Protoc, 2006. 1:2048-60.

Olafsen T, Betting D, Kenanova V E, Salazar F B, Clarke P, Said J, Raubitschek A A, Timmerman J M, Wu A M. Recombinant Anti-CD20 Antibody Fragments for Small-Animal PET Imaging of B-Cell Lymphomas. J Nuc Med, 2009. 50(9)1 500-1508.

Olson W C, Heston W D W, Rajasekaran A K. Clinical Trials of Cancer Therapies Targeting Prostate Specific Membrane Antigen. Reviews on Recent Clinical Trials, 2007. 2: 182-190.

Slovin S F. Targeting novel antigens for prostate cancer treatment: focus on prostate-specific membrane antigen. Expert Opin Ther Targets, 2005. 9(3): 561-570.

Vaidynathan G, Jestin E, Olafsen T, Wu A M, Zalutsky M R. Evaluation of an anti-p185(HER2)(scFv-C(H)2-C(H)3)2 fragment following radioiodination using two different residualizing labels: SGMIB and IB-Mal-D-GEEEK. Nucl Med Biol, 2009. 36(6): 671-80.

Wong J Y, Chu D Z, Williams L E, Yamauchi D M, Ikle D N, Kwok C S, Liu A, Wilczynski S, Colcher D, Yazaki P J, Shively J E, Wu A M, Raubitschek A A. Pilot trial evaluating an 123I-labeled 80-kilodalton engineered anti-carcinoembryonic antigen antibody fragment (cT84.66 minibody) in patients with colorectal cancer. Olin Cancer Res, 2004. 10(15):5014-21.

Wu A M and Senter P D. Arming antibodies: prospects and challenges for immunoconjugates. Nat Biotechnol, 2005. 23(9)1137-46.

Wu A M and Olafsen T. Antibodies for molecular imaging of cancer. Cancer J, 2008. 14(3)191-7.

Wu A M. Antibodies and Antimatter: The resurgence of ImmunoPET. J Nucl Med, 2009. 50(1):2-5.

Yazaki P J, Wu A M, Tsai S W, Williams L E, Ikle D N, Wong J Y C, Shively J E, and Raubitschek A A. Tumor targeting of radiometal labeled anti-CEA recombinant T84.66 diabody and T84.66 minibody: Comparison to radioiodinated fragments. Bioconj Chem, 2001. 12. 220-228.

Patents and Published Patent Applications

Wu, Anna. Antibody Construct. U.S. Pat. No. 5,837,821, filed Jun. 24, 1994, and issued Nov. 17, 1998.

Bander, Neil. Treatment and diagnosis of cancer. U.S. Pat. No. 6,649,163, filed Jul. 20, 1999, and issued Nov. 18, 2003.

Bander, Neil. Treatment and diagnosis of cancer. U.S. Pat. No. 6,770,450, filed Jul. 20, 1999, and issued Aug. 3, 2004.

Bander, Neil. Carr, Francis. Hamilton, Anita. Modified antibodies to prostate-specific membrane antigen and uses thereof. U.S. Pat. No. 7,045,605, filed May 30, 2002, and issued May 16, 2006.

Bander, Neil. Treatment and diagnosis of prostate cancer. U.S. Pat. No. 7,112,412, filed Jul. 20, 1999, and issued Sep. 26, 2006.

Bander, Neil. Treatment and diagnosis of cancer. U.S. Pat. No. 7,163,680, filed Aug. 13, 2001, and issued Jan. 16, 2007.

Bander, Neil. Treatment and diagnosis of cancer. U.S. Pat. No. 6,136,311, filed Jul. 17, 1997, and issued Oct. 24, 2000.

Bander, Neil. Treatment and diagnosis of prostate cancer with antibodies to extracellular PSMA. U.S. Pat. No. 6,107,090, filed Apr. 9, 1997, and issued Aug. 22, 2000.

Bander, Neil. Carr, Francis. Hamilton, Anita. Methods of treating prostate cancer with anti-prostate specific membrane antigen antibodies. U.S. Pat. No. 7,514,078, filed May 30, 2003, and issued Apr. 7, 2009.

What is claimed is:

1. A cys-diabody comprising:
   an scFv sequence that can bind PSMA, the scFv comprising a variable heavy domain (VH) linked to a variable light domain (VL) by a linker sequence; and a cysteine tail,
   wherein the VH comprises a heavy chain CDR1 that is a CDR1 in SEQ ID NO: 12; a heavy chain CDR2 that is a CDR2 in SEQ ID NO: 12; a heavy chain CDR3 that is a CDR3 in SEQ ID NO: 12, and wherein the VL comprises a light chain CDR1 that is a CDR1 in SEQ ID NO: 12; a light chain CDR2 that is a CDR2 in SEQ ID NO: 12; and a light chain CDR3 that is a CDR3 in SEQ ID NO: 12, or
   wherein the VH comprises a heavy chain CDR1 that is a CDR1 in SEQ ID NO: 13; a heavy chain CDR2 that is a CDR2 in SEQ ID NO: 13; a heavy chain CDR3 that is a CDR3 in SEQ ID NO: 13, and wherein the VL comprises a light chain CDR1 that is a CDR1 in SEQ ID NO: 13; a light chain CDR2 that is a CDR2 in SEQ ID NO: 13; and a light chain CDR3 that is a CDR3 in SEQ ID NO: 13, or
   wherein the VH comprises a heavy chain CDR1 that is a CDR1 in SEQ ID NO: 14; a heavy chain CDR2 that is a CDR2 in SEQ ID NO: 14; a heavy chain CDR3 that is a CDR3 in SEQ ID NO: 14, and wherein the VL comprises a light chain CDR1 that is a CDR1 in SEQ ID NO: 14; a light chain CDR2 that is a CDR2 in SEQ ID NO: 14; and a light chain CDR3 that is a CDR3 in SEQ ID NO: 14, or
   wherein the VH comprises a heavy chain CDR1 that is a CDR1 in SEQ ID NO: 15; a heavy chain CDR2 that is a CDR2 in SEQ ID NO: 15; a heavy chain CDR3 that is a CDR3 in SEQ ID NO: 15, and wherein the VL comprises a light chain CDR1 that is a CDR1 in SEQ ID NO: 15; a light chain CDR2 that is a CDR2 in SEQ ID NO: 15; and a light chain CDR3 that is a CDR3 in SEQ ID NO: 15.

2. The cys-diabody of claim 1, wherein the VH comprises a heavy chain CDR1 that is a CDR1 in SEQ ID NO: 12; a heavy chain CDR2 that is a CDR2 in SEQ ID NO: 12; a heavy chain CDR3 that is a CDR3 in SEQ ID NO: 12, and wherein the VL comprises a light chain CDR1 that is a CDR1 in SEQ ID NO: 12; a light chain CDR2 that is a CDR2 in SEQ ID NO: 12; and a light chain CDR3 that is a CDR3 in SEQ ID NO: 12.

3. The cys-diabody of claim 1,
   wherein the VH is a VH of SEQ ID NO: 12, and wherein the VL is a VL of SEQ ID NO: 12, or
   wherein the VH is a VH of SEQ ID NO: 13, and wherein the VL is a VL of SEQ ID NO: 13, or
   wherein the VH is a VH of SEQ ID NO: 14, and wherein the VL is a VL of SEQ ID NO: 14, or
   wherein the VH is a VH of SEQ ID NO: 15, and wherein the VL is a VL of SEQ ID NO: 15.

4. The cys-diabody of claim 1, wherein the VH comprises SEQ ID NO: 3, and wherein the VL comprises SEQ ID NO: 17.

5. The cys-diabody of claim 1, wherein the cys-diabody, comprises SEQ ID NO:12.

6. The cys-diabody of claim 1, wherein the cys-diabody, comprises SEQ ID NO:13.

7. The cys-diabody of claim 1, wherein the cys-diabody, comprises SEQ ID NO:14.

8. The cys-diabody of claim 1, wherein the cys-diabody, comprises SEQ ID NO:15.

9. The cys-diabody of claim 1, further comprising an N-terminus signal sequence to enable secretion of the cys-diabody when expressed in a cell.

10. The cys-diabody of claim 1, wherein the scFv is in a VHVL orientation such that the VH is upstream of the VL.

11. The cys-diabody of claim 1, wherein the scFv is in a VLVH orientation such that the VL is upstream of the VH.

12. The cys-diabody of claim 1, wherein the linker sequence is 5 or 8 amino acids in length.

13. The cys-diabody of claim 1, wherein the cys-diabody is conjugated to a diagnostic agent.

14. The cys-diabody of claim 13, wherein the diagnostic agent is selected from the group consisting of a radioactive substance, a dye, a contrast agent, a fluorescent molecule, a bioluminescent compound, a bioluminescent molecule, an enzyme, an enhancing agent, a quantum dot, and a metal nanoparticle.

15. The cys-diabody of claim 1, wherein the cys-diabody is conjugated to a therapeutic agent.

16. The cys-diabody of claim 15, wherein the therapeutic agent is selected from the group consisting of: a chemotherapeutic agent, a therapeutic antibody or antibody fragment, a toxin, a radioisotope, an enzyme, a nuclease, a hormone, an immunomodulator, an antisense oligonucleotide, a chelator, a boron compound, a photoactive agent and a dye.

17. An isolated polynucleotide that encodes a monomer of a cys-diabody, wherein the polynucleotide comprises SEQ ID NO: 6, SEQ ID NO: 7, SEQ ID NO: 8, or SEQ ID NO: 9.

18. A cys-diabody comprising:
   an scFv sequence that can bind PSMA, the scFv comprising a variable heavy domain (VH) linked to a variable light domain (VL) by a linker sequence; and a cysteine tail,
   wherein the VH comprises SEQ ID NO: 5 and the VL comprises SEQ ID NO: 19.

* * * * *